(12) United States Patent
Discenzo et al.

(10) Patent No.: US 7,581,434 B1
(45) Date of Patent: Sep. 1, 2009

(54) INTELLIGENT FLUID SENSOR FOR MACHINERY DIAGNOSTICS, PROGNOSTICS, AND CONTROL

(75) Inventors: Frederick M. Discenzo, Brecksville, OH (US); Dukki Chung, Mayfield Heights, OH (US); Martin W. Kendig, Thousand Oaks, CA (US); Kenneth A. Loparo, Chesterland, OH (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 262 days.

(21) Appl. No.: 11/395,790

(22) Filed: Mar. 31, 2006

Related U.S. Application Data

(63) Continuation-in-part of application No. 10/670,614, filed on Sep. 25, 2003, now Pat. No. 7,104,116.

(51) Int. Cl.
 *G01N 11/00* (2006.01)
(52) U.S. Cl. .................................................. 73/53.01
(58) Field of Classification Search ................. 73/53.01
 See application file for complete search history.

(56) References Cited

U.S. PATENT DOCUMENTS

| | | | |
|---|---|---|---|
| 2,837,913 A | 6/1958 | Rich et al. |
| 3,256,741 A | 6/1966 | Wise |
| 3,393,553 A | 7/1968 | Kleinschmidt |
| 3,479,863 A | 11/1969 | Kleiss |
| 3,526,127 A | 9/1970 | Sarkis |
| 3,548,637 A | 12/1970 | Wicks, III |
| 3,823,599 A | 7/1974 | Litz et al. |
| 3,977,234 A | 8/1976 | Lynch et al. |
| 3,982,422 A | 9/1976 | Harrison et al. |
| 4,072,045 A | 2/1978 | Kopito |
| 4,184,364 A | 1/1980 | Du Bae |
| 4,200,541 A | 4/1980 | Kinner et al. |
| 4,253,149 A | 2/1981 | Cunningham et al. |
| 4,269,604 A | 5/1981 | Snowden, Jr. |
| 4,457,161 A | 7/1984 | Iwanaga et al. |
| 4,542,640 A | 9/1985 | Clifford |
| 4,546,389 A | 10/1985 | Gibson et al. |
| 4,563,893 A | 1/1986 | Tanyolac et al. |

(Continued)

OTHER PUBLICATIONS

Stuebner, Partial European Search Report EP 04 02 3004. Munich, Jan. 7, 2005.

(Continued)

*Primary Examiner*—Hezron Williams
*Assistant Examiner*—Rodney T Frank
(74) *Attorney, Agent, or Firm*—Turocy & Watson LLP; R. Scott Speroff

(57) ABSTRACT

A system that facilitates device and/or machinery diagnostics, prognostics and control by way of condition sensing, such as sensing the condition of the device and/or a fluid of the device (e.g., fluid health indicators). The system can employ a plurality of sensors to determine a current state and estimate a future state of the fluid and/or device, as well as providing control of the device, e.g., in order to increase the remaining useful life of the fluid and/or operation of the device. The sensors can communicate wirelessly with each other, with the device, and/or with a central control system that provides, e.g., sensor fusion, prognostics and control integration. In addition, the sensors can be powered locally based upon the physical or chemical properties of the environment.

37 Claims, 40 Drawing Sheets

U.S. PATENT DOCUMENTS

| | | | |
|---|---|---|---|
| 4,632,758 A | 12/1986 | Whittle | |
| 4,675,662 A | 6/1987 | Kondo et al. | |
| 4,770,027 A | 9/1988 | Ehara et al. | |
| 4,782,332 A | 11/1988 | Cipris et al. | |
| 4,783,987 A | 11/1988 | Hager et al. | |
| 4,792,791 A | 12/1988 | Cipris et al. | |
| 4,798,738 A | 1/1989 | Yafuso et al. | |
| 4,818,348 A | 4/1989 | Stetter | |
| 4,869,874 A | 9/1989 | Falgt | |
| 4,922,745 A | 5/1990 | Rudkin et al. | |
| 4,926,682 A | 5/1990 | Holm-Kennedy et al. | |
| 4,935,040 A | 6/1990 | Goedert | |
| 4,941,346 A | 7/1990 | Suzuki et al. | |
| 4,979,124 A | 12/1990 | Sachse et al. | |
| 5,004,583 A | 4/1991 | Guruswamy et al. | |
| 5,038,893 A | 8/1991 | Willner et al. | |
| 5,120,421 A | 6/1992 | Glass et al. | |
| 5,151,110 A | 9/1992 | Bein et al. | |
| 5,199,298 A | 4/1993 | Ng et al. | |
| 5,200,027 A | 4/1993 | Lee et al. | |
| 5,338,442 A | 8/1994 | Siskin et al. | |
| 5,359,881 A | 11/1994 | Kalotay et al. | |
| 5,388,442 A | 2/1995 | Kumar et al. | |
| 5,389,390 A | 2/1995 | Kross | |
| 5,417,821 A | 5/1995 | Pyke | |
| 5,418,058 A | 5/1995 | Li et al. | |
| 5,469,369 A | 11/1995 | Rose-Pehrsson et al. | |
| 5,474,910 A | 12/1995 | Alfano | |
| 5,485,491 A | 1/1996 | Salnick et al. | |
| 5,487,313 A | 1/1996 | Johnson | |
| 5,512,882 A | 4/1996 | Stetter et al. | |
| 5,540,086 A | 7/1996 | Park et al. | |
| 5,572,328 A | 11/1996 | Fouckhardt et al. | |
| 5,581,028 A | 12/1996 | Barth et al. | |
| 5,614,830 A | 3/1997 | Dickert et al. | |
| 5,633,809 A | 5/1997 | Wissenbach et al. | |
| 5,640,103 A | 6/1997 | Petsche et al. | |
| 5,644,395 A | 7/1997 | Folta | |
| 5,646,039 A | 7/1997 | Northrup et al. | |
| 5,654,497 A | 8/1997 | Hoffheins et al. | |
| 5,660,728 A | 8/1997 | Saaski et al. | |
| 5,661,666 A | 8/1997 | Pawlak | |
| 5,662,165 A | 9/1997 | Tubel et al. | |
| 5,674,401 A | 10/1997 | Dickert et al. | |
| 5,777,211 A | 7/1998 | Binienda et al. | |
| 5,798,452 A | 8/1998 | Martin et al. | |
| 5,817,928 A | 10/1998 | Garvey et al. | |
| 5,818,731 A | 10/1998 | Mittal et al. | |
| 5,852,229 A | 12/1998 | Josse et al. | |
| 5,892,143 A * | 4/1999 | Namerikawa et al. | 73/54.24 |
| 5,914,247 A | 6/1999 | Casey et al. | |
| 5,957,170 A | 9/1999 | Bedi et al. | |
| 5,959,189 A | 9/1999 | Jeng et al. | |
| 5,959,191 A | 9/1999 | Lewis et al. | |
| 5,964,318 A | 10/1999 | Boyle et al. | |
| 5,968,371 A | 10/1999 | Verdegon et al. | |
| 5,969,227 A | 10/1999 | Kenney | |
| 6,023,961 A | 2/2000 | Discenzo et al. | |
| 6,043,505 A | 3/2000 | Ames et al. | |
| 6,047,590 A * | 4/2000 | Namerikawa et al. | 73/54.24 |
| 6,051,437 A | 4/2000 | Luo et al. | |
| 6,052,348 A | 4/2000 | Belser et al. | |
| 6,070,456 A | 6/2000 | Cameron et al. | |
| 6,105,415 A | 8/2000 | Kenney | |
| 6,167,709 B1 | 1/2001 | Caracciolo et al. | |
| 6,196,057 B1 * | 3/2001 | Discenzo | 73/54.01 |
| 6,229,448 B1 * | 5/2001 | Bennett et al. | 340/618 |
| 6,272,905 B1 * | 8/2001 | Drzewiecki | 73/53.01 |
| 6,286,363 B1 | 9/2001 | Discenzo | |
| 6,295,873 B1 | 10/2001 | Condreva | |
| 6,324,899 B1 * | 12/2001 | Discenzo | 73/53.05 |
| 6,434,512 B1 | 8/2002 | Discenzo | |
| 6,469,521 B1 | 10/2002 | Klun et al. | |
| 6,490,911 B1 * | 12/2002 | Namerikawa et al. | 73/54.24 |
| 6,534,010 B2 | 3/2003 | Sentmanat | |
| 6,546,785 B1 * | 4/2003 | Discenzo | 73/53.05 |
| 6,561,010 B2 | 5/2003 | Wilson et al. | |
| 6,565,749 B1 | 5/2003 | Hou et al. | |
| 6,777,009 B1 | 8/2004 | Shealy | |
| 6,805,312 B2 | 10/2004 | Capp | |
| 6,823,718 B2 | 11/2004 | Sandford et al. | |
| 6,877,360 B1 * | 4/2005 | Discenzo | 73/53.05 |
| 6,922,664 B1 | 7/2005 | Fernandez et al. | |
| 6,975,966 B2 * | 12/2005 | Scott et al. | 702/183 |
| 6,994,016 B1 | 2/2006 | Bunker et al. | |
| 7,019,638 B1 | 3/2006 | Wallace | |
| 7,024,920 B2 | 4/2006 | Discenzo | |
| 2002/0127623 A1 | 9/2002 | Minshull et al. | |
| 2003/0099754 A1 | 5/2003 | Sakai et al. | |
| 2003/0101801 A1 | 6/2003 | Wilson et al. | |
| 2004/0052702 A1 | 3/2004 | Shuman et al. | |
| 2004/0259226 A1 | 12/2004 | Robey et al. | |
| 2005/0043894 A1 | 2/2005 | Fernandez | |
| 2005/0066711 A1 | 3/2005 | Discenzo | |
| 2005/0068846 A1 | 3/2005 | Wulf et al. | |
| 2005/0106562 A1 | 5/2005 | Abbott et al. | |
| 2005/0107980 A1 | 5/2005 | Cocchis et al. | |
| 2005/0112255 A1 | 5/2005 | Tottenham et al. | |
| 2005/0112557 A1 | 5/2005 | Liu et al. | |
| 2005/0198990 A1 | 9/2005 | Kateman et al. | |
| 2005/0256774 A1 | 11/2005 | Clothier et al. | |
| 2006/0008866 A1 | 1/2006 | Flick et al. | |
| 2006/0068412 A1 | 3/2006 | Tang | |
| 2006/0115559 A1 | 6/2006 | Jones, Jr. | |
| 2006/0129327 A1 | 6/2006 | Kim et al. | |
| 2006/0272415 A1 | 12/2006 | Liu et al. | |
| 2007/0003996 A1 | 1/2007 | Hitt et al. | |
| 2007/0042505 A1 | 2/2007 | Israel et al. | |
| 2007/0116607 A1 | 5/2007 | Wang et al. | |
| 2007/0134659 A1 | 6/2007 | Plante et al. | |
| 2007/0142322 A1 | 6/2007 | Kaspar et al. | |
| 2007/0159325 A1 | 7/2007 | Oleynik | |
| 2007/0211784 A1 | 9/2007 | Simunovic et al. | |
| 2008/0213444 A1 | 9/2008 | Mixon et al. | |

OTHER PUBLICATIONS

OA Dated Jul. 1, 2008 for U.S. Appl. No. 11/348,089, 25 pages.
OA Dated Aug. 22, 2008 for U.S. Appl. No. 11/347,894, 16 pages.
Berkeley MicroInstruments, Microviscometer Model BMV100, Jan. 1998.
Karagounis, et al. "A Pd-PdO Film Potentiometric pH Sensor", IEEE Transactions on Biomedical Engineering, vol. BME-33, No. 2, Feb. 1986.
OA mailed Jan. 30, 2009 for U.S. Appl. No. 11/348,089, 31 pages.
OA mailed Mar. 17, 2009, for U.S. Appl. No. 11/347,894, 25 pages.

* cited by examiner $R_p = 2R_i$, $C_{dl} = C_i/2$

| Sample code Sensor | Hours | k (S/m) x10^-13 | Rs (Ω) x10^-4 Sensor C3 | Cc (F) x10^-11 Sensor C3 | Rp (Ω) x10^10 Sensor C3 | Cdl (F) x10^-10 Sensor C3 | OCP (Volt) Sensor E4/A8 | TAN (Mg KOH/g) | Viscosity @ 40 C (cSt) | Iron (ppm) | Water (%Vol) | Oxidation | Severity |
|---|---|---|---|---|---|---|---|---|---|---|---|---|---|
| New 23699 | 0 | 87 | 0.093 | 5.8 | 0.0050 | 6.130 | 0.47/0.35 | 0.04 | 25.4 | 0 | Nil | 0.673 | Normal |
| Degraded 23699 from gearbox – no load | | | | | | | | | | | | | |
| L0528-01 | 3.9 | 321 | | | | | | | | | | | |
| L0528-02 | 6.6 | 346 | 0.095 | 5.3 | 0.0030 | 5.77 | | | | | | | |
| L0529-01 | 9.8 | 313 | 0.100 | 5.2 | 0.0004 | 5.20 | | | | | | | |
| L0529-02 | 13.6 | 328 | 0.096 | 5.4 | 0.0037 | 7.60 | | 0.34 | 228.7* | 4 | Nil | 0.573 | Moderate |
| L0530-03 | 17.3 | 301 | | | | | | | | | | | |
| L0530-01 | 20.1 | 235 | 0.106 | 5.0 | 0.0010 | 5.07 | 0.46/N | 0.38 | 61.0* | 4 | Nil | 0.618 | Moderate |
| L0602-02 | 27.2 | | | | | | | | | | | | |
| L0602-01 | 32.9 | 360 | 0.100 | 5.8 | 0.0001 | 5.97 | | 0.29 | 58.2* | 2 | Nil | 0.616 | Moderate |
| L0603-02 | 35.9 | | | | | | | | | | | | |
| L0603-01 | 40.6 | | | | | | | | | | | | |
| L0604-01 | 49.0 | 709 | 0.097 | 5.4 | 0.0014 | 4.00 | 0.20/0.33 | 0.43 | 97.0* | 1 | Nil | 0.606 | Moderate |
| Degraded 23699 from gearbox – load rating = 1.3 time nominal rating | | | | | | | | | | | | | |
| L0613-01 | 3.2 | 722 | 0.090 | 5.3 | 0.0012 | 6.26 | | 0.08 | 25.4 | 21 | Nil | 0.677 | Observation |
| L0613-02 | 5.7 | | | | | | | | | | | | |
| L0613-03 | 8.2 | 957 | 0.103 | 5.2 | 0.0014 | 3.88 | 0.38/N | 0.08 | 25.4 | 19 | Nil | 0.673 | Observation |
| L0613-04 | 9.7 | 831 | | | | | | | | | | | |
| L0617-01 | 12.7 | 891 | 0.097 | 5.5 | 0.0018 | 5.95 | 0.39/N | 0.10 | 25.3 | 209 | Nil | 0.680 | Severe |
| L0617-02 | 33.7 | 556 | 0.096 | 5.3 | 0.0025 | 341.5 | 0.98/1.33 | | | | | | |
| Hydraulic Fluid | | | | | | | | | | | | | |
| New 83282 | 0 | 10 | 6.383 | 3.7 | 0.0015 | 19.94 | N/0.52 | 0.03 | 14.8 | 0 | Nil | 0.462 | Normal |
| Jet fuel | | | | | | | | | | | | | |
| JP-5 | 0 | 6 | 7.962 | 4.2 | 68.90 | 9894.4 | N/0.45 | | | | | | Normal |
| JP-8 | 0 | 145 | 2.114 | 3.5 | 0.1840 | 2.337 | N/0.29 | | | | | | Normal |

Note: the viscosity results may not be relevant, the sample separated into two layers during the viscosity test    N=Not available, Nil=No water

FIG. 24

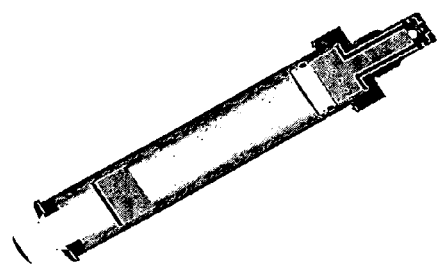
FIG. 50
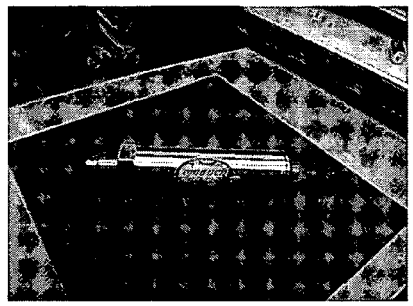 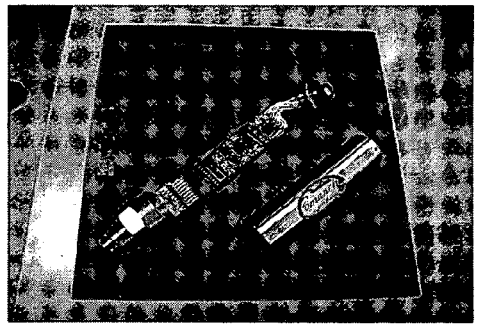
FIG. 51                FIG. 52

INTELLIGENT FLUID SENSOR FOR MACHINERY DIAGNOSTICS, PROGNOSTICS, AND CONTROL

CROSS-REFERENCE TO RELATED APPLICATIONS

This application is a Continuation-in-Part of U.S. application Ser. No. 10/670,614, filed Sep. 25, 2003, and entitled "FLUID SENSOR FIXTURE FOR DYNAMIC FLUID TESTING." The entirety of this application is incorporated herein by reference.

TECHNICAL FIELD

The subject invention generally relates to measurement of multiple parameters of fluids and machinery. More particularly, the invention relates to a system and/or methodology that facilitates real-time, in situ measurements in order to diagnose, forecast, probe and/or control the machinery, process, products, and/or fluids.

BACKGROUND OF THE INVENTION

Dynamoelectric machines such as motors and generators and other rotating machines such as gears, pumps, compressors and bearing systems including rolling element bearings and hydrodynamic bearings are widely employed in industrial, military and commercial facilities. These machines are relied upon to operate with minimal attention and provide for long, reliable operation. Many facilities operate several hundred or even thousands of such machines concurrently, several of which are integrated into a large interdependent process or system. Several machines, such as aircraft, land vehicles, and marine systems employ sensors to obtain measurements related to critical parameters of fluid that operates within the machines. Like most machinery, at least a small percentage of such equipment is prone to failure. Some of these failures can be attributed to loss of lubrication, incorrect lubrication, lubrication breakdown, or lubrication contamination.

Depending on the application, failure of a machine in service can possibly lead to system or process latency, inconvenience, material scrap, machinery damage, hazardous material cleanup, and even a dangerous situation. Thus, it is desirable to diagnose machinery for possible failure or faults early in order to take preventive action and avoid such problems. Absent special monitoring for certain lubrication problems, a problem may have an insidious effect in that although only a minor problem at the outset, the problem could become serious if not detected. For example, bearing problems due to inadequate lubrication, lubrication contamination or other causes may not become apparent until significant damage has occurred.

Proper lubrication facilitates extension of machinery life. For example, when motor lubricant is continuously exposed to high temperatures, high speeds, stress or loads, and/or an oxidizing environment, the lubricant will deteriorate and lose its lubricating effectiveness. The loss of lubricating effectiveness will affect two crucial functions of a lubrication system, namely: (1) to reduce friction; and (2) to remove heat. Continued operation of such a degraded system may result in even greater heat generation, further exacerbating system degradation, eventually leading to substantial machinery damage and ultimately catastrophic failure.

To protect the system (e.g., a motor, a pump, an engine, a gearbox . . . ), the lubricant should be changed in a timely fashion. However, a balance must be struck—on one hand it is undesirable to replace an adequate lubricant but on the other hand it is desired to replace a lubricant that is in its initial stages of breakdown or contamination prior to occurrence of equipment damage. Moreover, in some circumstances, e.g., during critical periods of operation, it may be infeasible or impossible to replace a lubricant even if it becomes known that a replacement is necessary.

Measurements relating to machine fluids obtained from sensing elements and/or a laboratory process are then utilized to prevent substantial degradation of the machine fluids, and thus prevent damage to the machine. Even if such measurements are taken at regular intervals, however, a maintenance engineer is still required to effectuate maintenance measures (e.g., fluid addition, fluid replacement, addition of anti-oxidants . . . ). Particular machinery requiring fluid maintenance can be located at positions on the machinery that is difficult to reach and therefore requires a significant amount of the maintenance engineer's time to perform such maintenance. Furthermore, the maintenance engineer is prone to human error and can add incorrect fluids and/or fluid additives to a particular machine or machine component, as well as provide the machine or machine component with an over-abundance of fluid. Access to some machines for fluid service may require access to hazardous areas by maintenance personnel or may require machinery or process shutdown to insure worker safety. The additional risk of worker safety and possible machinery shutdown for lubricant service must be minimized to provide ultimate protection of maintenance staff and insure continued operation of process machines. These risks, operating cost, and other potential maintenance errors can result in accelerated failure of the machine and/or machine component, increased worker risk of safety and reduced economic performance of the organization.

Conventional systems and/or methods for in situ measurement and analysis of fluids in machinery only detect one or a very small number of fluid parameters. Moreover, there does not exist a way to collect a wide variety of fluid parameters from various types of sensors in order to get a complete picture of the condition of the fluid in real time. For example, one sensor may be able to detect a parameter and determine that it is not ideal, but generally, the sensor does not know why that is so, much less what remedial actions (if any) could be taken to mitigate a harmful condition. Further, certain types of contaminants within a fluid cannot easily or inexpensively be detected. Lastly, knowing what is the condition of the lubricant and the possible reasons permits determining whether it is safe to continue operating the equipment or if an immediate equipment shutdown is warranted.

For example, metal wear during operation can contaminate a fluid with metal particles, which can be a problem not easily detectable in a useful way. Detecting metal in fluids today is either performed by extracting a sample and performing a laboratory analysis. Alternatively, there are a few commercial products that employ optical methods to detect particles. The optical methods are costly, large, heavy, and do not determine the particle type. They only detect the particle size and number of particles. Another difficulty often arisen because occasionally entrapped air bubbles may also be classified as a particle by optical sensors.

In addition, there exist many difficulties for a multiple sensor system to communicate with other components. Hence, there is a need for an effective wireless solution for wireless and/or satellite communication. One difficulty associated with sensors that are not wired is providing power to the sensor. Due to a limited life, batteries are often not a feasible solution. The remaining life of batteries are typically difficult to determine raising the likelihood of unexpected loss of sensor function, battery replacement requires labor and machinery access, and replacement batteries represent a non-trivial maintenance and logistics burden including the safe, environmentally conscious disposal of depleted batteries. Today there are some energy harvesting techniques that extract, convert, and store ambient energy from the environment. However, none of these techniques exploit the characteristics of the fluid itself. Lastly, sensors typically employed are passive devices and do not change fluid or sensor conditions in the vicinity of the sensor elements.

In view of at least the above, there exists a strong need in the art for a system and/or methodology facilitating improved real-time in situ measurement and analysis of parameters relating to fluid in machinery, and a system and/or methodology for maintaining such fluids.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The claimed subject matter facilitates improved real-time, in situ diagnostics, prognostics and/or control by way of condition sensing. For example, a sensor that is installed in a device or machine can monitor the fluids of the device in order to ascertain various parameters relating to the fluid. By examining these parameters it is possible to determine a current state of many "health indicators" relating to the fluid. It is also possible, e.g., by employing a variety of information and/or algorithms to determine or infer a future state. The future state can be employed, e.g., to determine the remaining useful life of a fluid, the remaining time of operation of the device or machinery, as well as prognostications relating to remedial actions that can extend the useful life of the fluid and/or device. In accordance therewith, a control component can provide control information based on the sensed condition of a fluid to a device in order to mitigate a deleterious condition of the fluid.

According to an aspect of the claimed subject matter, a model-based electrical impedance spectroscopy (EIS) can be employed to determine fluid conductivity. This model can be utilized in connection with non-conductive fluids. The EIS data can be employed to determine the presence as well as an amount of metal ions in a fluid, e.g., by comparing the EIS data with known and/or likely metal ion data. Additionally, the electro-chemical sensor elements can perform a reduction-oxidation operation in the vicinity of the electrode surfaces using cyclic-voltammetry techniques. For example, an electrochemical sensor can detect these metal ions and, e.g., based upon the type of metal, the amount and/or in connection with other sensor data such as EIS response, vibrations or noise in a certain area, a determination can be made regarding metal wear as well as its likely origin or source. From this data, a sensor can be directed to make further probes and a control component can make prognostications about the future as well as potential remedial actions intended to mitigate a harmful condition detected by the sensor.

In accordance with another aspect of the claimed subject matter, sensor fusion can be employed to receive, diagnose, and/or collate a variety of sensor data from a plurality of sensors. In this manner, a clearer, more robust picture of the current state of the fluid can be obtained. The sensor data can be relayed via a wireline or wireless communications interface to a component that can provide for distributed processing of multi-sensor machinery data as well as minimize bandwidth requirements of the network. A suite of different sensors may be networked together by established network protocols such as DeviceNet, Ethernet, IntelliBus, Bluetooth, IEEE802.15.4, or Fieldbus to provide local, component-specific sensing and analysis, sub-system health analysis, system or process level analysis, and summary real-time information aggregated to provide a more accurate, comprehensive picture of the state of the dynamic system. In addition, control such as model-based and/or predictive control and/or multi-agent systems (MAS) can be integrated with dynamic health assessment information and prognostics and employed. Analytic results or raw data can be provided to a central-level processing component for fluid health assessment and prognostics. In these cases, a prognostics model can be very accurate and effective. Prognostic results can be compared to observed results and the model may be dynamically adapted and employ machine learning techniques to automatically improve performance over time and adapt to changing environments and operating conditions.

According to yet another aspect of the claimed subject matter, a sensor or suite of sensors can communicate with other components by way of wireless communication. This aspect can eliminate the costly wiring requirement of sensors as well as the associated potential for damage, failure, leaks, etc. Additionally or alternatively, these sensors can harvest power from the environment and/or the fluid it is analyzing. For example, the motion of the fluid and/or device (e.g., due to flow, pressure fluctuations, vibrations, thermal gradients, etc.) can be harvested by, e.g., a micro-electrical mechanical system (MEMS) structure or a NANO structure. According to another aspect, power can be harvested from a charge in a dielectric fluid. The charge could be created by, e.g., particle detachment, tribocharging, scuffing on a surface of the device, work activity of the device, etc. According to still another aspect, the sensor can include an electrode with a sacrificial element that supplies energy to the sensor based upon an electrochemical reaction between the fluid and the element. The sensor can also be powered by utilizing fuel cell technology with a membrane that harvests energy by way of the aspects already described. According to yet another aspect, a micro-generator can be employed to supply the sensor with the power necessary for operation.

To the accomplishment of the foregoing and related ends, the invention then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

FIG. 24 is a Table comprising a fluid analysis summary.

FIG. 50 is an exemplary illustration of a mounting sensor package.

FIG. 51 is an exemplary an assembled view of the sensor package.

FIG. 52 is an exemplary a disassembled view of the sensor package

DETAILED DESCRIPTION OF THE INVENTION

Figure 1A:
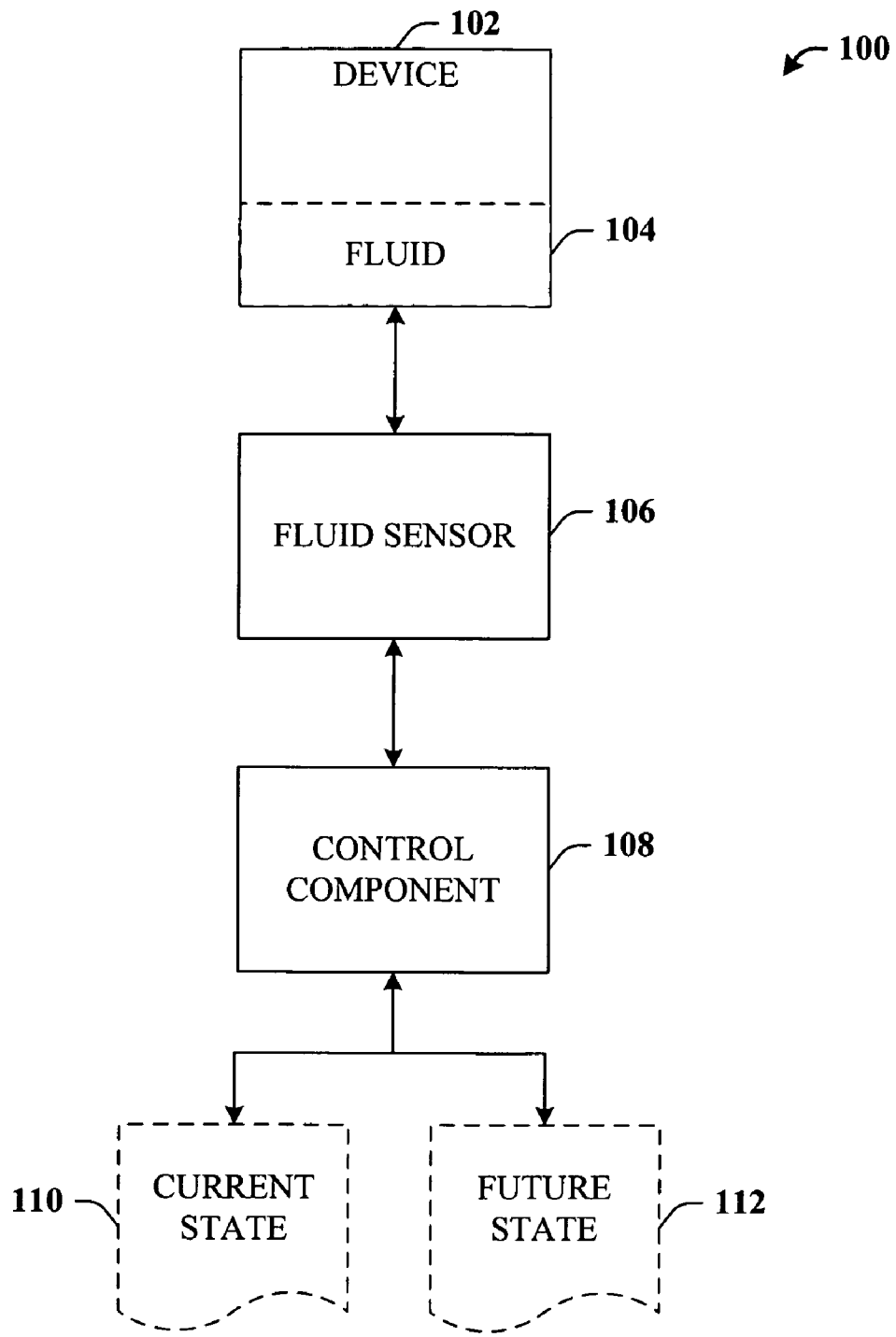
FIG. 1A is a block diagram of a system that facilitates machinery diagnostics, prognostics and control by way of condition sensing.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the term "computer component" is intended to refer to a computer-related entity, either hardware, a combination of hardware, firmware, and software, software, or software in execution. For example, a component may be, but is not limited to being, a process running on a processor, a processor, a microprocessor, a micro-computer, a single-board computer, a personal computer (PC), a personal digital assistance (PDA) device, an object, an executable, a thread of execution, a program, and/or a computer. By way of illustration, both an application running on a server and the server can be a computer component. One or more components may reside within a process and/or thread of execution and a component may be localized on one computer and/or distributed between two or more computers.

As used herein, the terms to "infer" or "inference" refer generally to the process of reasoning about or inferring states of the system, environment, and/or user from a set of observations as captured by way of events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Inferences can also be based on statistical (e.g., probabilistic or Bayesian) models, fuzzy logic systems, artificial neural nets, or any combination of these.

Referring now to the drawings, FIG. 1A illustrates a high-level system overview in connection with at least one aspect of the subject invention. The claimed subject matter relates to a novel system 100 that facilitates machinery diagnostics, prognostics and control by way of condition sensing. Generally, the system 100 can include a device 102 with a fluid 104, a fluid sensor 106 in contact with the fluid 104 and/or the device 102, and a control component 108 that can determine in real-time a current state 110 of the fluid 104 as well as infer a future state 112 of the fluid 104 (also in real-time) based at least in part upon information received from the fluid sensor 106. It is to be appreciated that the system 100 can include a plurality of devices 102 that can be referred to as a plurality or individually as device 102. Similarly, each device 102 can include several fluids 104, and each fluid 104 can be in contact with a plurality of fluid sensors 106. Accordingly, the components 102-112 can be referenced, respectively as a collection or individually, even though each of the components 102-112 can have individual characteristics that distinguish them from other components 102-112, respectively.

The device 102 can be substantially any machine or a component thereof in which the fluid 104 is present. For example, the device 102 can be a pump, a filter, a valve, an anti-friction bearing, a motor, an actuator, a pipe, a reactor vessel, a reservoir, an engine, a gearbox, a transmission, or any other component in which various properties of the fluid (e.g., the current state 110) are of interest. Accordingly, the fluid 104 can be any of a lubricant, a hydraulic fluid, water, a fuel, a coolant, a cutting oil, a beverage, a cooking oil, a food product, a biological fluid, a pharmaceutical fluid, a coating, etc. In accordance therewith, the fluid sensor 106 can monitor, measure and/or probe various parameters of the fluid 104 and/or the device 102 and can transmit data relating to the parameters to the control component 108 for diagnostics, prognostics or control of the device 102 and/or the fluid 104 and/or another device and/or a higher level operating decision or strategy. For instance, the current state 110 can be an evaluation of the current "health" of the fluid based upon the parameters monitored by the fluid sensor 106. Likewise, the future state 112 can be an estimate of the remaining useful life of the fluid. The estimate of remaining useful life of the fluid may in turn be used to signal bringing another piece of equipment to operational status to reduce the load on a failure-prone device or may result in limiting the control responsiveness of a system by reducing the control gains, or may signal an operator to not initiate a mission or a batch process to avoid incurring a costly failure during a critical mission or process operation. Decisions such as these occur frequently in aircraft systems (e.g., helicopter rescue missions) and process industries (e.g., bio-reactors for pharmaceuticals).

The parameters measured by the fluid sensor 106 can be virtually any characteristic relevant to the claimed subject matter, such as, e.g., oxidation level, temperature, viscosity, oxidation/reduction potential, pH, TAN, TBN, lubricity, dissolved oxygen, $H_2O$, conductivity, ferrous contamination, additive state, ionic species, chemical compounds or chemical contaminants, oxidation potential, dielectric analysis, conductivity, biological contamination, and density among others. Accordingly, the fluid sensor 106 can be an RTD sensor, an acidity sensor, an impedance sensor, an electro-chemical sensor, or the like. The data transmitted to the control component 108 can be applicable to the parameter, including the existence of the parameter as well as the amount of the parameter, rate of change, etc. It can also be applicable to multiple parameters. The one or multiple parameters may be sensed directly, derived from a sensed signal, derived from multiple sensor signals (e.g., using sensor fusion techniques), or derived from one or more sensor signals and/or control observations and/or model information and/or information from previous sensor signals and control responses. Exemplary devices 102, fluids 104, fluid sensors 106, parameters and data relating to the parameters are intended to be illustrative, and not limiting. It is to be understood that other examples exist that can be employed without departing from the scope and spirit of the claimed subject matter.

The control component 108 can determine the current state 110 of the fluid 104 (or device 102) based upon, e.g., a comparison of the data transmitted by the fluid sensor 106 with pre-existing data associated with the fluid 104 (or device 102) such as specification data, laboratory test results, chemical models, empirical degradation models and the like. The control component 108 can also infer a future state 112 of the fluid 104 and/or device 102 based upon the current state 110, the pre-existing data and/or a prognostics algorithm described infra. For example, the prognostics algorithm can employ a classical model, Bayesian, Dempster-Shafter, generalized evidence processing theory, fuzzy logic, artificial neural network, chemical model, empirical model, stochastic model, simulation model, sensor fusion, etc.

Figure 1B:
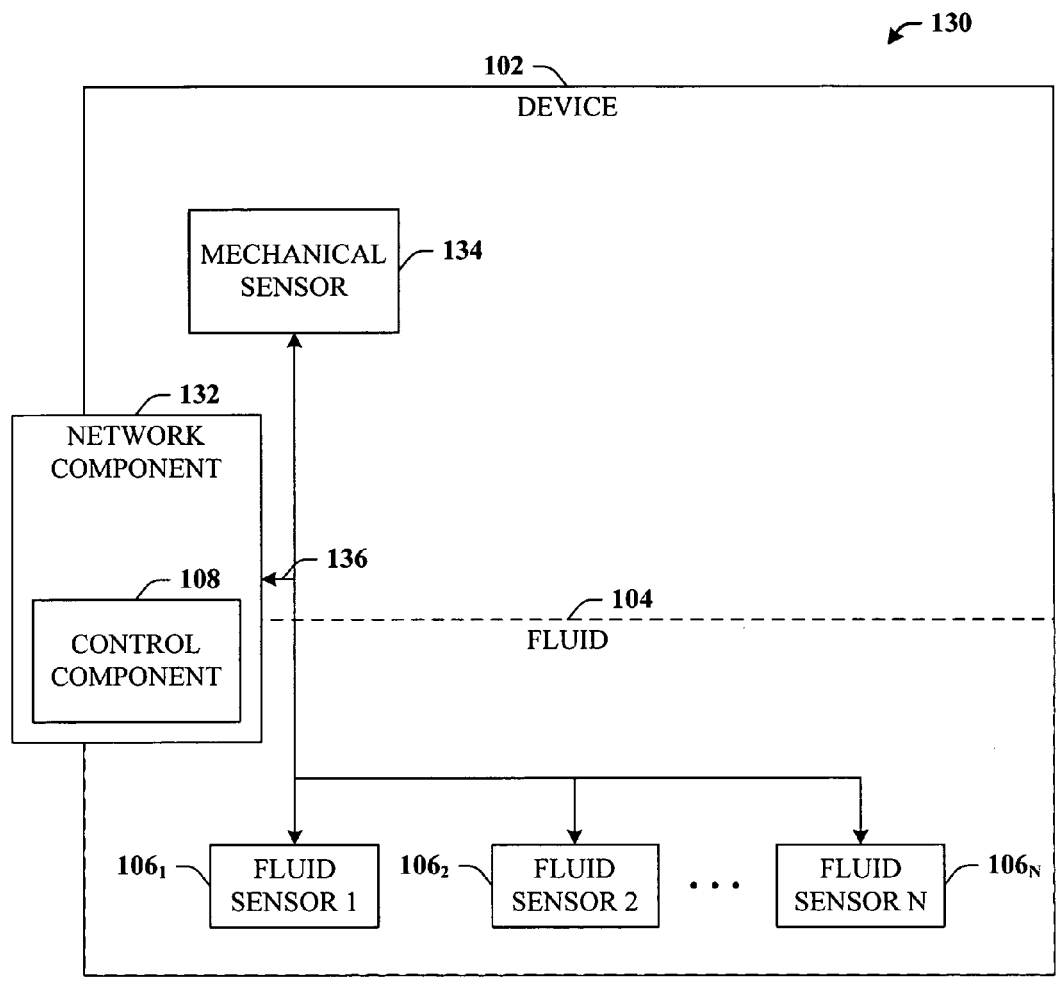
FIG. 1B is a block diagram of a multi-sensor system that facilitates machinery diagnostics, prognostics and control by way of condition sensing.

Referring briefly to FIG. 1B, a multi-sensor system 130 that facilitates machinery diagnostics, prognostics and control by way of condition sensing. Generally, the system 130 can include a network component 132 that can reside within the device 102 or be located remotely from the device 102. The network component can be a mechanical, electrical, computer-based, software module such as to support a wired network such as DeviceNet, Ethernet, Fieldbus, IntelliBus, Profibus, Modbus, or other LAN or alternatively a wireless network such as IEEE 802.11b (wireless Ethernet) or IEEE 802.15.4 (e.g., Zigbee) network interface, or alternatively a optical network (e.g., optical fiber). As described in connection with FIG. 1A, the control component 108 can receive a variety of information from the fluid sensors $106_1$-$106_N$, referred to here either collectively or individually as fluid sensor(s) 106. In addition to communication with the fluid sensors 106, the control component can also communicate with one or more mechanical sensor(s) 134 as well other sensors (not shown). For example, a mechanical sensor 134 can transmit to the control component 108 mechanical data relating to the device such as vibration data, acoustic data and the like. The communication path 136 by which the network component 132 and/or the control component 108 communicates with the sensors 106, 134 can be a wireless and/or a satellite communication path 136 as described above.

Referring back to FIG. 1A, it is to be appreciated that the control component 108 can be a processor embedded in the fluid sensor 106 as a self-contained unit that, e.g., communicates with other components, sensors and/or the device 102. The control component 108 can also be remote from the fluid sensor 108 and the communication between the components 102-108 can be accomplished by way of wireless protocols such as, e.g., IEEE 802.15.4, IEEE 802.11b, Bluetooth, satellite communication protocols and the like (e.g., communication path 136 from FIG. 1B). Moreover, as described supra, a wide variety of fluid parameters can be detected, and doing so may require multiple sensor elements in a single sensor and/or multiple sensors. By adopting wireless communication, the multiple parameters sensed by the sensors (e.g., the fluid sensor 106 as well another sensor that can detect, e.g., vibrations and/or acoustic noise in the device 102) can be communicated to a remote monitoring system or control system such as, e.g., in connection with the network component 132 of FIG. 1B described in greater detail infra. Since wiring for a conventional fluid sensor often represents a significant cost, e.g., in terms of materials and installation labor cost, such a wireless solution can provide cost benefits as well as mitigating exposure to potential wire damage and/or failure, providing increased safety particularly for environments with hard to reach locations and/or volatile, explosive, or corrosive environments and providing the ability to replace, exchange and/or bring online new sensors with relative ease.

In accordance with another aspect of the claimed subject matter, the control component 108 can control the behavior of the device 102 in order to alleviate or mitigate a harmful condition such as detrimental condition in the fluid 104. That is, the control component 108 can determine a response action based on the current state and/or predicted future state that is intended to mitigate the harmful condition by modifying the behavior, functionality and/or mode of operation of the device 102. Additionally or alternatively, the control component 108 can supply an alert that indicates the harmful condition and/or the remedial action to a remote component, a user and/or maintainer of the device 102. The notification may also indicate when a remedial action is required, the certainty or belief that the specified remedial action is required, and the implications and time frame for a new future state if the prescribed remedial action is not taken as advised by the control component 108.

By way of illustration and not limitation, the device 102 could be a tail rotor gearbox of a rotorcraft or a main transmission of a rotorcraft and the fluid 104 could be an associated lubricant of the gearbox. If the fluid sensor 106 detects, e.g., a high degree of oxidation in the lubricant and the control component 108 might make a prognosis (e.g., the future state 112) that indicates there are, e.g., 4 more hours of flight time at the current speed and gearbox loading. However, the control component 108 might determine that the oxidation in the lubricant or the rate of oxidation can be reduced by a remedial action such as reducing the tail rotor pitch that is employed to limit the stress on the tail rotor such as limiting high tack angles or high-G turns (e.g., changing the mode of operation of the device 102). As a result, instead of 4 hours the remaining useful life of the lubricant after implementing the remedial action and/or changing the mode of operation of the device 102 can be increased to, e.g., 20 hours. The remedial action can be implemented indirectly by, e.g., alerting a pilot of the aircraft. Additionally or alternatively, the remedial action could be automatic such as changing the gains or the rates at which tail rotor pitch changes. As described, by employing the information provided in the form of the current state 110, future state 112, and other information, the control component 108 can control the device 102 to extend the operational life of the device. For example, if it is determined that the operational life of the device 102 under current conditions is a certain period of time, and it is also determined that the device 102 needs to remain in operation longer than that period of time, then the control component 108 can, e.g., modify a mode of operation of the device 102. The control component 108 can test various scenarios designed to alleviate the particular condition detected by the fluid sensor 106, ideally selecting a mode of operation for the device that can yield an operational life that meets or surpasses the longer period of time. Based on potential mission requirements, variability in loading, and other expected disturbances; a different mode of operation that surpasses the required operating time with a higher degree of safety margin, greater certainty, or increased likelihood of meeting the operating lifetime requirements. Further, the fluid sensor 106 can provide constant diagnostics and prognostics such that the control component 108 can constantly update the current state 110 and future state 112, e.g., to determine if the prescribed "life-extending" control of the device is effective, etc. The results from this continual self-evaluation may be used to dynamically "tune" the future state algorithms or models to provide a more accurate estimate of remaining system lifetime for future system analysis and control.

According to another aspect the remedial action determined and/or implemented by the control component 108 can be an addition of an additive to the fluid 104, e.g., to counteract or mitigate a harmful condition. Since the fluid sensor 106 can provide a wealth of information relating to the chemistry and composition of the fluid 104, the fluid sensor 106 can also sense additive depletion for example. As another example, the fluid sensor 106 can sense the acidity of the fluid. As such, the device 102 can be equipped with a reservoir of an additive, e.g., an anti-oxidant additive that prevents or significantly reduces oxidation of the lubricant. Alternatively, the reservoir of an additive may contain an alkali (e.g., KOH) that when introduced into the lubricant changes the pH of the fluid 104. Accordingly, rather than accept excessive oxidation of the fluid or the corrosion of lubricated surfaces or being forced to change the fluid 104 in within a certain period of time that may be infeasible, impossible, dangerous, etc., all that may be necessary is to change the amount of anti-oxidant additive in the fluid or change acidity level by adding a small amount of alkali to increase (oftentimes dramatically so) the remaining useful life of the fluid 102, and, by proxy the available time the device 102 can operate without service.

Figure 1C:
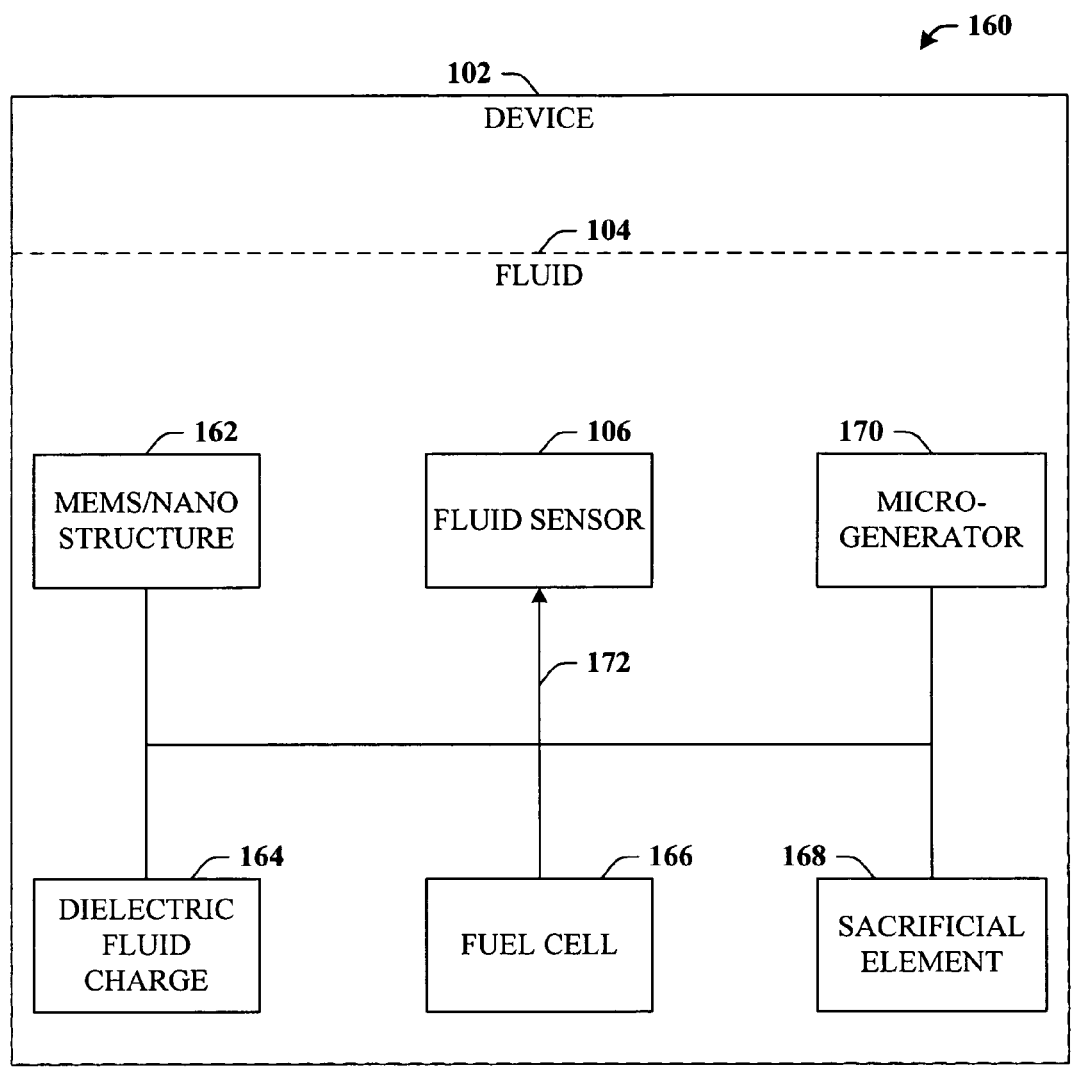
FIG. 1C is a block diagram of a system that facilitates a self-powered fluid sensor by employing characteristics of a fluid to harvest energy.

Referring now to FIG. 1C, a system 160 that facilitates a self-powered fluid sensor by employing characteristics of a fluid to harvest energy. Generally, the system 160 can include at least one of a structure 162 (e.g., a micro-electrical mechanical system (MEMS) structure, NANO structure, a mechanical structure, a MICRO structure . . . ), a dielectric fluid charge 164, a fuel cell 166, a sacrificial element 168, and a micro-generator 170. Depending upon the implementation, at least one of the items 162-170 can supply energy to the fluid sensor 106 along a path 172 that is typically a physical connection (e.g., items 162-170 are included and/or operatively coupled to the fluid sensor 106). In accordance therewith, the fluid sensor 106 can be locally powered by, e.g., utilizing physical characteristics, e.g., fluid movement and/or the chemical composition of the fluid 104 and/or the device 102. This aspect is especially useful in the case where the fluid sensor 106 is wireless, as conventional wired sensors are generally powered by way of the wiring. Conventional wireless sensors are typically battery powered, but difficulties can arise when the battery power diminishes. Additionally there is the cost for replacement batteries, the cost for logistics to provide new batteries at each sensor location and the disposal of depleted batteries, and the labor cost to replace batteries in distributed wireless sensors. Other conventional wireless sensors are attempting to employ energy harvesting using photovoltaic or piezoelectric generators. However, none of the conventional wireless sensors exploit the characteristics of the fluid 104 itself. Power may be generated locally by the fluid sensor 106 that can be used to power other fluid sensor elements 106 and the associated electronics, processor, and communications elements. Hence, fluid conditions and/or parameters may be transmitted using one of the readily available, ultra-low power wireless communications protocols.

As described, power for the fluid sensor 106 may be obtained from the physical environment using energy harvesting methods such as thermoelectric, photovoltaic, piezoelectric, etc. The claimed subject matter can also utilize the motion of the fluid 104 that the fluid sensor 106 is monitoring as a source of power. A number of cases are now provided for the sake of illustration rather than limitation. For example, certain structures 162 such as MEMS and NANO structures 162 can be constructed in the fluid 104 locally to the fluid sensor 106. These structures 162 can move in the fluid 104 based on, e.g., fluid flow or pressure fluctuations. One example is a simple flow-meter style paddle wheel that rotates in the fluid and generates a small amount of power. Another example is an actuator including a flapping plate, a rotating disk with a suitable vane structure, and/or pressure diaphragm. Yet another example is a dipstick (e.g., device 102) with a fluid sensor 106 attached wherein the dipstick is constructed of piezoelectric material and/or thermoelectric material to generate energy from the engine vibration (in the case of a piezoelectric material) and/or from the thermal gradient between the hot oil temperature and the environment (in the case of a thermoelectric material). It is to be appreciated that fluid sensor 106 is, e.g., an electrical and/or electro-chemical sensor 106, element 162 can include multiple other sensors instead of or in addition to the MEMS 162. For example, include a MEMS pressure sensor, a flow sensor, an optical sensor (e.g., near IR or NIR sensor or optical particle sensor) and/or density sensor. Since for certain non-aqueous fluids, viscosity changes as a function of pressure, the use of pressure information may be employed for interpreting the sensed viscosity since the viscosity and density change with pressure.

Additionally or alternatively, power for the fluid sensor 106 can be provided based upon the chemical composition of the fluid 104. For example, power may be generated by utilizing an electrochemical reaction in connection with electrodes designed with sacrificial elements 168. As well, power may be generated using a charge 164 that is created as a result of, e.g., the wear process occurring in a weak dielectric fluid 104 (e.g., particle detachment, or tribocharging), surface scuffing, or surface work activity. For instance, the generation of a charge 164 in the fluid 104 and/or surfaces in contact with the fluid 104 can be transferred to the fluid sensor 106. Other techniques such as electrostatic to electric energy conversion may be used to convert the generated power to usable electricity for the fluid sensor 106. In addition, the micro-generator 170 may also be used to generate usable electricity, as well as membrane technologies coupled with fuel cell 166 technologies that use the fluid 104 being monitored to generate power for the fluid sensor 106 as described above.

Figure 1D:
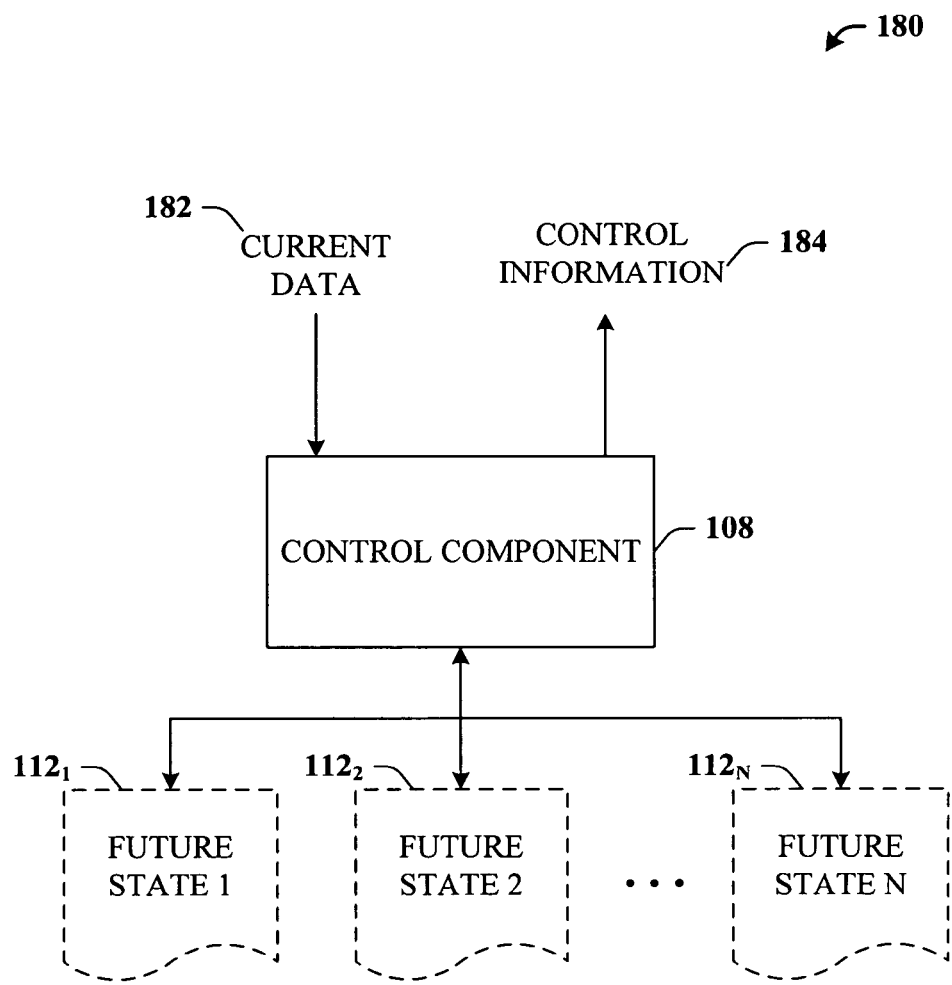
FIG. 1D is a block diagram of a system that can forecast a plurality of future states based upon a variety of data associated with current and possible future conditions.

Turning briefly to FIG. 1D, a system 180 that can forecast a plurality of future states based upon a variety of data associated with current conditions is depicted. Generally, the system 180 can include the control component 108 that can determine or infer a plurality of future states 112. Each of the future states 112 may be based on a probabilistic assumption or estimate. For example, each future state 112 can be inferred from current data 182. The current data 182 can be fluid parameters sensed by any number of sensors (not shown) as described above, historical data including previous environments, operating conditions and associated fluid degradation ranges as well as parameters that can affect the system in other ways such as expected wear rate of mechanical components. According to one aspect, the current data 182 can be different environmental variables (e.g., weather, terrain . . . ), different possible or probabilistic mission parameters, different operating profiles, different equipment operating states, different fluid modifications, different operators, or any other relevant constraint that may affect the operational life of the system 180. The control component 108 can provide feedback information based upon one or several of the future states 112 in the form of control information 184. The control information 184 can be employed to provide alerts and/or suggestions, or automatically control a device (not shown) or a portion of a device in order to achieve a desired result.

It is to be understood and appreciated that the future states 112 may be combined or interpolated to show other possible future states 112, e.g., based on operating conditions and probability distributions. For example, the future states 112 can be utilized to map out a number of various scenarios of a given mission to determine whether the mission can be completed based upon a probability distribution, a degree of certainty regarding the probability, what is known about the environment, what can be learned about the environment and/or internal components once the mission is under way, etc. Current data 182 can be constantly provided in real time and can reflect feedback results of changes implemented based upon the control information 184. Similarly, control components 108 may be provided feedback information 182 describing the system state that corresponds to a previously predicted future state. The actual state realized may be compared to the previously predicted future state and the operation of the control components 108 automatically updated to improve the prediction capability for future operation. Other aspects of the claimed subject matter will become apparent in the discussion below.

Lubricant Electrical Property Measurement

Electrochemical impedance spectroscopy (EIS) is an AC impedance measurement technique for measuring the electrical properties of a lubricant. The fundamental approach of this technique is to apply a sinusoidal excitation signal from a high frequency to a low frequency (either voltage or current) to the electrodes and measure the electrochemical cell response to the input stimulation (either current or voltage). Electrochemical impedance is normally measured using a small excitation signal so that the measurement only causes minimal perturbation of the electrochemical test system. Moreover, this is done so that the cell response is pseudo-linear. In a linear (or pseudo-linear) system, the current response to a sinusoidal potential will be a sinusoid at the same frequency but with different amplitude and will be shifted in phase relative to the input signal.

However, the electrical conductivity of a lubricant oil is very low (electrical conductivity of petroleum is $3 \times 10^{-11}$ Siemens(S)/m as compared to the conductivity of a standard KCl solution which on the order of $10^{-5}$ S/m). To measure the AC impedance of a lubricant, the excitation signal should be large enough to compensate for the low conductivity of the lubricant while confining the measurement (output response) to a pseudo-linear segment of the cell current versus voltage (input versus output) curve. A basic approach to measuring the electrical properties of a lubricant is to apply a constant amplitude AC voltage between two identical planes, parallel electrodes of effective area A, and separation d, and measure the current response of the cell. In an electrochemical cell, slow electrode kinetics, slow preceding chemical reactions and diffusion can all impede electron flow, and can be considered analogous to the resistors, capacitors, and inductors that impede the flow of electrons in an AC circuit. Thus, the impedance of lubricant oil can be defined as E=IZ where E=potential (V), I=current (A), and Z=Impedance ($\Omega$).

When the measurement of the response of an electrochemical cell in the pseudo-linear range, the current response to a sinusoidal potential will be a sinusoid at the same frequency but shifted in phase as described by the following two equations: $E(t)=M_V \sin(\omega t)$, and $I(t)=M_I \sin(\omega t+\Phi)$ where I(t)=instantaneous current, E(t)=instantaneous voltage, $M_V$=Maximum amplitude of voltage, $M_I$=Maximum amplitude of current, $\omega$=frequency in radians per second=$2\pi f$, f is frequency in Hertz, t=time, and $\phi$=Phase shift in radians. However, it is often more convenient to analyze the AC (sinusoidal) response of an electrochemical cell using a complex impedance approach. Therefore, the impedance of the lubricant can be expressed as given in equation $$Z = \frac{E' + E''j}{I' + I''j}, \text{ where}$$

$$Z = Z' + Z''j, |Z| = \sqrt{Z'^2 + Z''^2}, \theta = \arctan\frac{Z''}{Z'},$$

and where Z'=Real part of Lubricant impedance, Z''=Imaginary part of Lubricant impedance, |Z|=Magnitude of Lubricant impedance, and $\theta$=Phase angle of Lubricant impedance.

Conductivity of a liquid is related to the ability of the liquid to conduct an electric current between two electrodes. In solution, the current flows by ion transport. Therefore, with an increasing amount of ions present in the liquid, the liquid will have a higher conductivity. The conductivity also depends on liquid temperature. The conductivity in general is defined by equation at a certain liquid temperature.

$$k = \sigma \frac{d}{A},$$

where k=Conductivity of liquid (Siemens/m), $$\sigma = \text{Liquid Conductance (Siemens)} = \frac{1}{R},$$

and where R=Liquid Resistance ($\Omega$), d=Distance between two electrodes(m), and A=effective area of the electrode ($m^2$). Resistivity is inversely proportional to conductivity. Therefore, the liquid resistivity, ($\rho$), can be defined by equation.

$$(\rho) = \frac{1}{k}(\Omega m)$$

The cell constant of an electrochemical cell is defined by equation.

$$\text{Cell constant} = \frac{d}{A}$$

Equivalent Circuit for the Metal/Lubricant/Metal System

Figure 2:
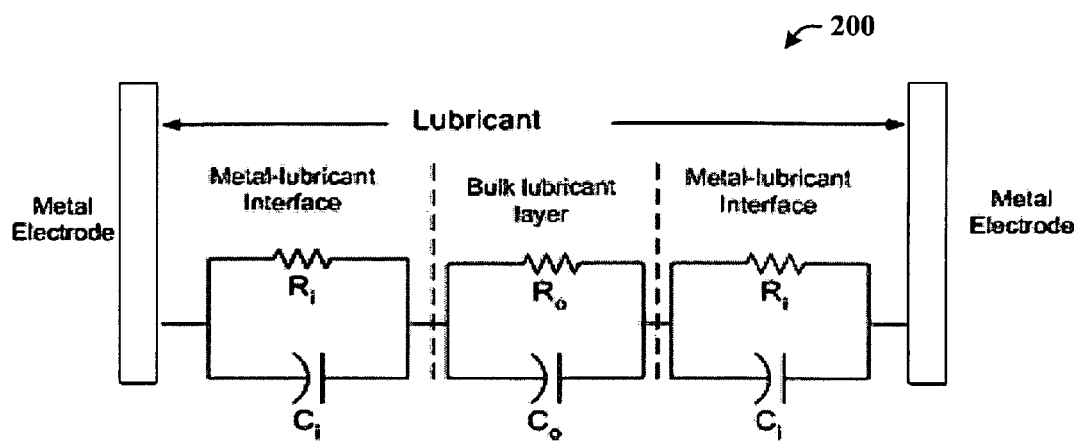
FIG. 2 is a block diagram of a simple circuit model of an electrode-lubricant system.

Referring now to FIG. 2, a block diagram of a simple circuit model 200 of an electrode-lubricant system is depicted. In the study of an electrochemical system, EIS data is commonly analyzed by fitting it to an equivalent electrical circuit model (e.g., model 200). EIS is based upon the premise that every liquid and solid has the ability to pass current when a voltage is applied to it. When an alternating current (AC) voltage is applied to a material, the ratio of V/I (i.e. voltage/current) is known and is measured as the impedance. In materials that are not generally regarded as conductors of electricity, the impedance varies as the frequency of applied voltage changes. This is due to the properties of the liquid or solid. Thus, if a measurement of impedance over a suitable range of frequencies is made, it is possible to relate the resultant impedance to the physical and chemical properties of the materials.

The magnitude of applied AC voltage is mainly dependent on the conductivity of the materials. For example it is enough to measure the impedance of water by applying 20 mV of voltage. However, since the resistivity of oil is much more than water, a higher value of voltage is needed to measure the impedance of oil. The typical value of the applied voltage for the impedance measurement of oil is approximately 300 mV or 400 mV.

The elements in the circuit model 200 are common elements such as resistors, capacitors and inductors. Each element in the circuit model 200 should represent a basic process in the physical electrochemistry of the underlying system (not shown) for which the model 200 is a representation. The electrical circuit model 200 can be employed to determine ac impedance measurements of the resistance and capacitance of lubricants and the metal-lubricant interfacial reactions.

$R_i$ represents the polarization resistance or charge-transfer resistance at the electrode-lubricant interface. The value of $R_i$ can depend on the electrochemical reaction rate of the lubricant reacting with the metal electrode. $C_i$ represents the double layer capacitance at the interface. An electrical double layer occurs at the interface between an electrode and the surrounding lubricant. This double layer is formed as ions from the lubricant stay on the electrode surface. Charges in the electrode are separated from the charges of these ions and form a capacitor. The value of $C_i$ depends on the electrode potential, temperature, ionic concentrations, types of ions, oxide layers, electrode roughness, and the adsorption and desorption phenomena. $R_o$ and $C_o$ represents the resistance and capacitance of the bulk lubricant layer. The measurements of the electrical resistance and capacitance of the electrode-lubricant interface and the bulk lubricant layer can provide useful information about the mechanisms of lubricant additive-metal surface interactions. This information may also be useful in the study of lubricant degradation.

Analysis of the Electrode-Lubricant Model

Figure 3:
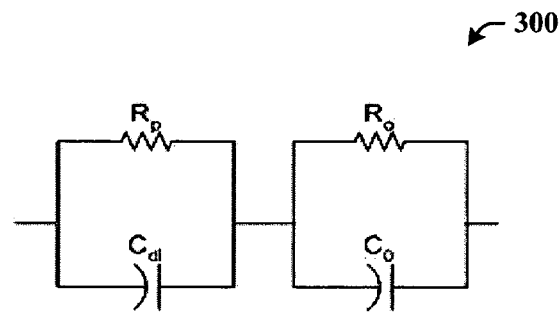
FIG. 3 is a block diagram of a simplified circuit that is equivalent to the simple circuit model of an electrode-lubricant system.

The total impedance of the electrode-lubricant model 200 is the combination of the impedance of the charge transfer resistance, $Z_{Ri}$, the impedance of the double layer capacitance, $Z_{Ci}$, the impedance of the bulk lubricant layer resistance $Z_{Ro}$ and the impedance of the bulk lubricant layer capacitance, $Z_{Co}$. If it is allowed that:

$$Z_{Ro} = R_o \quad Z_{Ri} = R_i$$
$$Z_{Co} = \frac{-j}{\omega C_o} \quad Z_{Ci} = \frac{-j}{\omega C_i}$$

then the model 200 can be further simplified to the equivalent circuit 300 shown in FIG. 3. The new impedance $Z_{Rp}$ equals to 2Ri and $Z_{Cdl}$ equals to $$\frac{-2j}{\omega C_i}.$$

The total impedance of the electrode-lubricant model is given by equations $$Z_{total} = \frac{Z_{Rp} Z_{Cdl}}{Z_{Rp} + Z_{Cdl}} + \frac{Z_{Ro} Z_{Co}}{Z_{Ro} + Z_{Co}}$$

$$Z_{total} = \frac{R_P - jR_p^2 \omega C_{dl}}{R_p^2 \omega^2 C_{dl}^2 + 1} + \frac{R_o - jR_o^2 \omega C_o}{R_o^2 \omega^2 C_o^2 + 1}$$

$$Z_{total} = Z'_{total} + jZ''_{total}$$

$$Z'_{total} = \frac{R_p}{R_p^2 \omega C_{dl}^2 + 1} + \frac{R_o}{R_o^2 \omega C_o^2 + 1}$$

$$Z''_{total} = \frac{-R_p^2 \omega C_{dl}}{R_p^2 \omega^2 C_{dl}^2 + 1} - \frac{R_o^2 \omega C_o}{R_o^2 \omega^2 C_o^2 + 1}$$

The limiting cases for the equivalent circuit model 200 (FIG. 2) are the low frequency and high frequency asymptotes, that is $$\lim_{(\omega \to 0)} Z_{total} = Z_{Rp} + Z_{Ro} = R_p + R_o$$

$$\lim_{(\omega \to \infty)} Z_{total} = Z_{Cdl} + Z_{Co} = \frac{C_{dl} + C_o}{j\omega C_{dl} C_o}$$

Thus, the total impedance at $\omega=0$ is pure resistance, while the total impedance at $\omega=\infty$ is pure capacitance.

Figure 4:
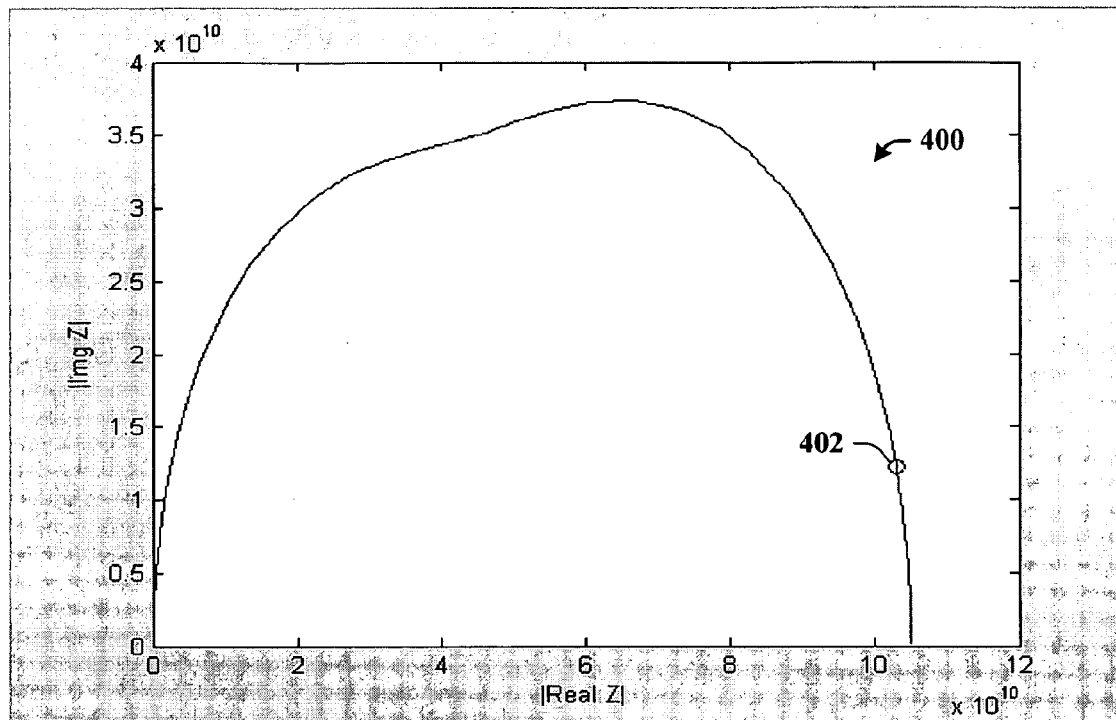
FIG. 4 is a Nyquist plot of the electrode-lubricant model in the case where $R_p C_{dl}$ is significantly different from $R_o C_o$.

Turning now to FIG. 4, a Nyquist plot 400 is illustrated. The Nyquist plot 400 demonstrates the complex-plane plot of the electrode-lubricant model (e.g., model 200) when values of $R_o C_o$ and $R_p C_{dl}$ are not significantly different. For example, when $R_p = 6.0 \times 10^{10} \Omega$, Cdl=$5.0 \times 10^{-11}$ F, $R_o = 4.5 \times 10^{10} \Omega$ and $C_o = 1.0 \times 10^{-11}$ F. The plot has a shape similar to a semicircle. The summation of the resistance $R_o$ and the resistance $R_p$ can be estimated from the intersection of the Nyquist plot and the real axis for low frequency input excitations. The summation of the impedance of the capacitance $C_o$ and the capacitance $C_{dl}$ can be estimated from the intersection of the Nyquist plot and the imaginary axis for high frequency input excitation. A circle 402 indicates the total impedance at frequency 0.01 Hz, which is a relatively low frequency value for real applications. In practice, it is frequently not possible to sample a system at zero frequency (dc). Consequently, the extraction of the model resistances from the measured impedance requires extrapolation of the observed value $Z(\omega)$ to $\omega=0$.

Figure 5:
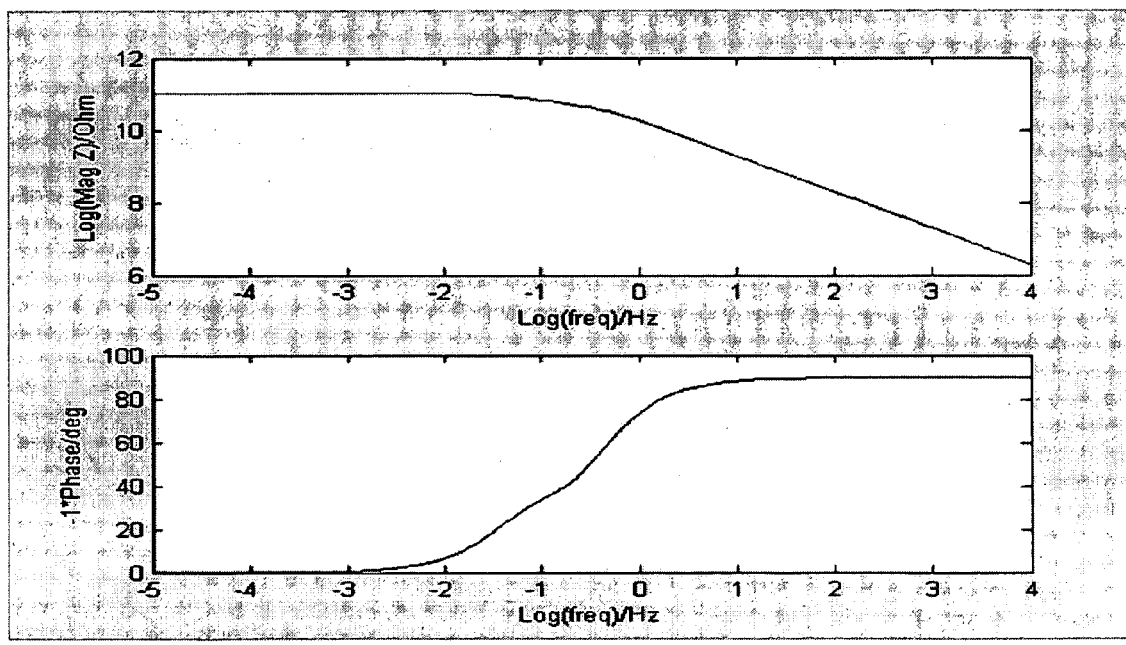
FIG. 5 is a Bode plot of the electrode-lubricant model in the case where $R_p C_{dl}$ is significantly different from $R_o C_o$.

With reference to FIG. 5, a Bode plot of an electrode-lubricant model (e.g., model 200) is displayed wherein $R_p = 6.0 \times 10^{10} \Omega$, $C_{dl} = 5.0 \times 10^{-11}$ F, $R_o = 4.5 \times 10^{10} \Omega$ and $C_o = 1.0 \times 10^{-11}$ F. The Bode plot in FIG. 5 illustrates the frequency response of the electrode-lubricant model. At the high frequency ($10$-$10^4$ Hz), the phase shift is $-90$ degree. This phase shift response indicates that the characteristic of the model behave like a pure capacitor. At the low frequency ($10^{-5}$-$10^{-3}$ Hz), the phase shift is 0 degree. This phase shift response indicates that the characteristic of the model behave like a pure resistor.

Figure 6:
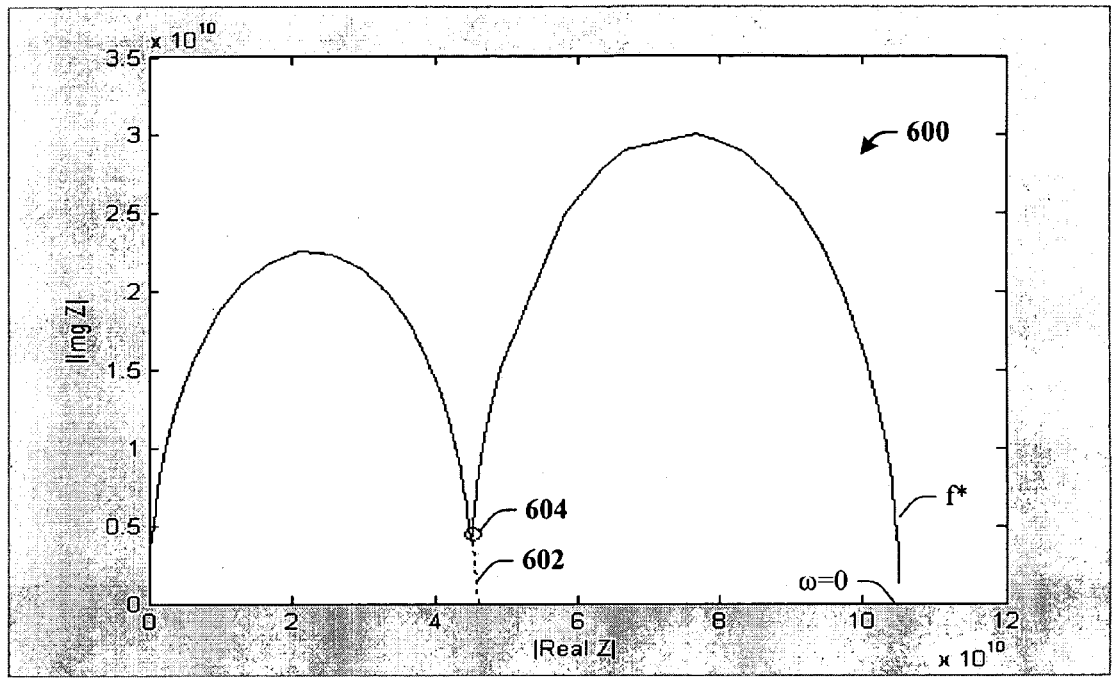
FIG. 6 is a Nyquist plot of the electrode-lubricant model that illustrates the relaxation phenomenon.
Figure 7:
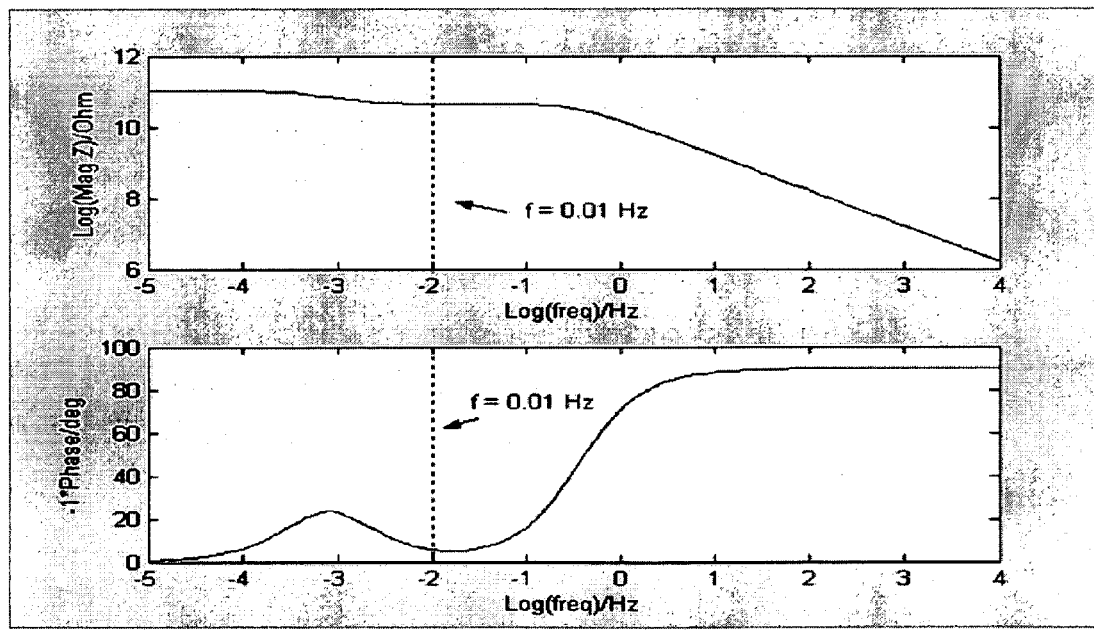
FIG. 7 is a Bode plot of the electrode-lubricant model that illustrates the relaxation phenomenon.

Turning to FIGS. 6 and 7, FIG. 6 depicts a Nyquist plot 600 that shows the complex-plane plot of the electrode-lubricant model when values of $R_o C_o$ and $R_p C_{dl}$ are significantly different (e.g., $R_p C_{dl} \gg R_o C_o$). For example, where $R_p = 6.0 \times 10^{10} \Omega$, Cdl=$5.0 \times 10^{-9}$ F, $R_o = 4.5 \times 10^{10} \Omega$ and $C_o = 1.0 \times 10^{-11}$ F. If the lowest frequency employed is f*, extrapolation to the real axis intercept yields a resistance $R_p + R_o$ at $\omega=0$. However, if the lowest frequency employed is less than 0.01 Hz, extrapolation to the real axis intercept will give an incorrect estimation of the resistance, $R_p + R_o$, as shown by the dashed line 602. In this case, the low-frequency relaxation is not detected and the extrapolation gives only a resistance $R_o$ that is obviously lower than the resistance, $R_p + R_o$. The circle 604 indicates the impedance at frequency 0.01 Hz.

The Bode plot in FIG. 7 also indicates the relaxation phenomena. The phase shift increases from near zero degree at 0.01 Hz to twenty-five degree and decrease to zero degree again at 0.00001 Hz. It has been determined that the relationship between the capacitance of the lubricant and the oil film thickness is given by the following equation:

$$C = s\upsilon \frac{A}{d'},$$

where C=lubricant capacitance, s=specific, dielectric constant of the oil, v=dielectric constant of a vacuum, A=effective area of the electrodes, and d'=oil-film thickness. The resistance of the lubricant has the relationship with the oil-film thickness (d') as given by the following equation:

$$R = \rho \frac{d'}{A},$$

where R=lubricant resistance and ρ=the bulk resistivity of the lubricant.

Because the conductivity of a lubricant, in general, is extremely low, the distance between the two electrodes of the impedance sensor should be very small in order to lower the resistance of the lubricant between the electrodes to current flow. From the equations supra, the capacitance of the lubricant is inversely proportional, while, the resistance of the lubricant is proportional to the thickness of oil film. The thickness of the oil film is actually proportional to the distance between the two electrodes and is given by the following equation:

$$d = d' + 2d'',$$

where $d'$=thickness of oil film or thickness of the bulk lubricant layer and $d''$=thickness of the electrode-lubricant interfacial region.

By reducing the distance between the electrodes (d), the thickness of the bulk lubricant layer is decreased, while the thickness of the interfacial region remains constant.

Figure 8:
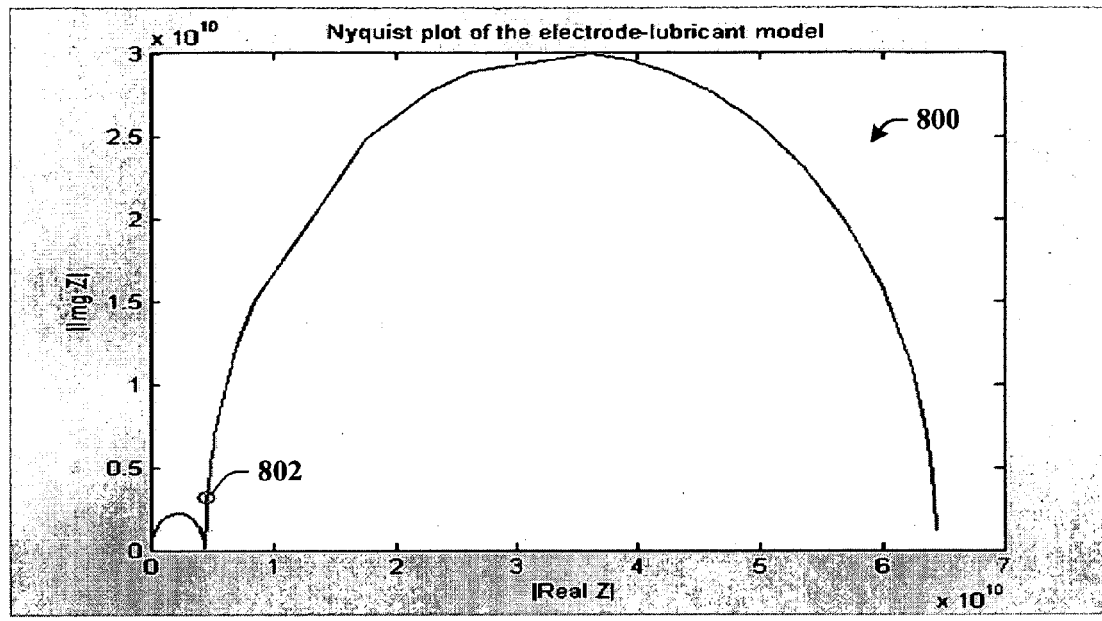
FIG. 8 is a Nyquist plot of the electrode-lubricant model when the distance between the electrodes is reduced by a factor of 10.
Figure 9:
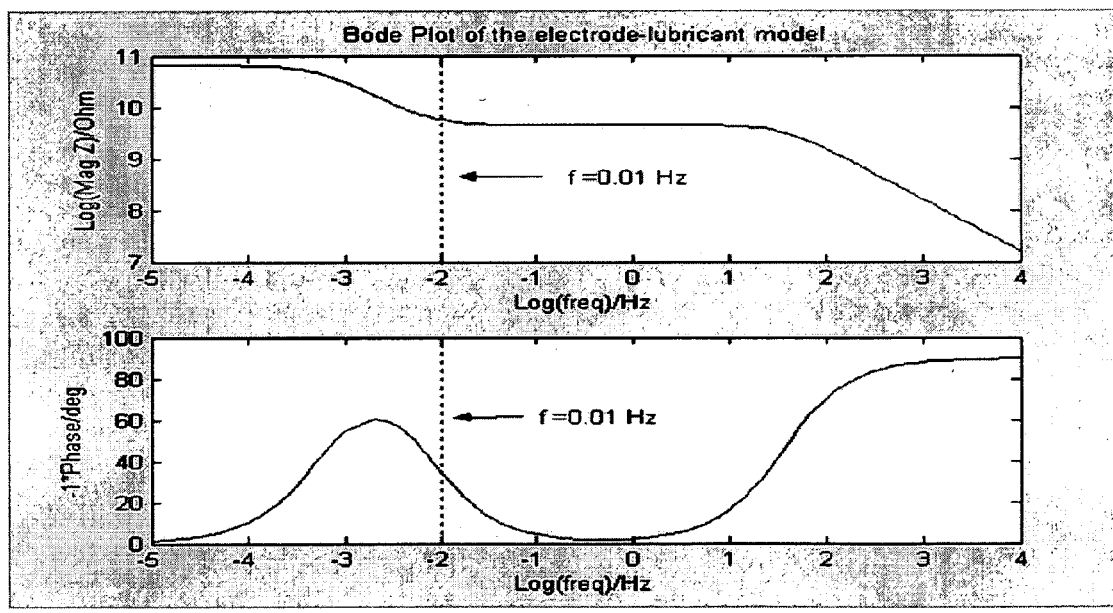
FIG. 9 is a Bode plot of the electrode-lubricant model when the distance between the electrodes is reduced by a factor of 10.
Figure 10:
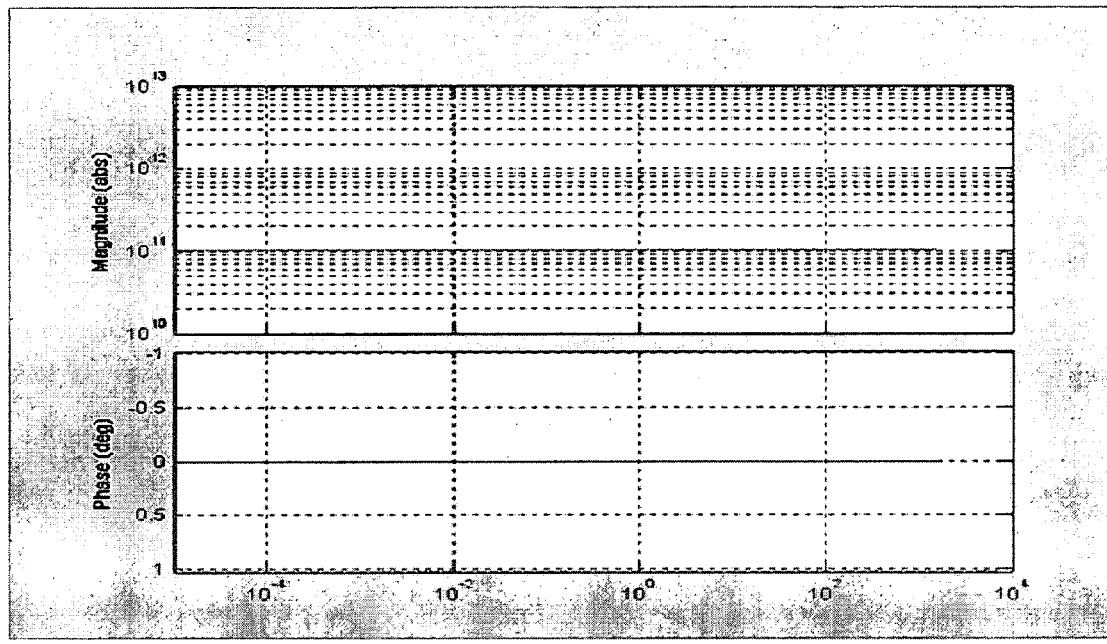
FIG. 10 is a Bode plot of the frequency response of the first term in an equation.

Referencing FIGS. 8 and 9, plots of the model (e.g., model 200) when the distance between the two electrodes is reduced by tenfold are shown. For example, when $R_p$=6.0×10$^{10}$Ω, Cdl=5.0×10$^{-9}$ F, $R_o$=4.5×10$^9$Ω and $C_o$1.0×10$^{-10}$ F. The Nyquist plot 800 shows the impedance of the model under these conditions. The presence of the second semicircle or the second relaxation is detected at the 0.01 Hz frequency, which is indicated by the circle 802. At this frequency, the plot of the system frequency response also indicates the second relaxation in the system (as shown in FIG. 7). By using this closer electrode spacing, the parameters of the model can be extracted using the analysis of the frequency response (Bode Plot) and a curve fitting algorithm.

In FIG. 9 (as well as FIG. 7), a dashed line indicates the magnitude and the phase of impedance at a frequency of 0.01 Hz. The analysis of the electrode-lubricant model illustrates two very important requirements of an impedance measurement. The first is that a sufficiently wide frequency range is required for the impedance measurement. Secondly, the impedance measurement and the parameter estimation (with the presence of two relaxations) are significantly improved by the reduction of the electrode space. However, it requires further studies to determine suitable electrode spacing(s) in order to use an impedance sensor for detecting water and/or conductive particle contamination in the lubricant.

Extraction of the Electrode-Lubricant Model Parameters from EIS Data

As described supra, the analysis of the electrode-lubricant model demonstrates that the estimation of $R_o + R_p$ can be determined by extrapolating the complex plane plot from the low frequency end to the intersection with the real axis. The extrapolation of the complex plane plot to the imaginary axis at the high frequency end provides an estimate of $Z_{Co} + Z_{Cdl}$. However, it is often difficult to determine the correct semicircle through the experiment data, especially if there is a significant scatter in the data. In general, a Bode plot provides a clearer description of the electrochemical system's frequency-dependent behavior than does a Nyquist plot. The evaluation of EIS data by using a Bode plot can provide additional information for model parameter estimation. The equation of the total impedance can be written in the alternative form as follow:

$$Z(\omega) = \frac{(R_p + R_o)\left(1 + j\omega \frac{R_p R_o (C_{dl} + C_o)}{R_p + R_o}\right)}{(j\omega C_o R_o + 1)(j\omega C_{dl} R_p + 1)}$$

Frequency Response Analysis of the Electrode-Lubricant Model

Frequency response analysis is the study of the steady-state response of a system to a sinusoidal input. By computing the log of the magnitude on both sides of the equation given by the log of the magnitude of the impedance is given by:

$$\log|Z(\omega)| = \log|(R_p + R_o)| + \log\left|1 + j\omega \frac{R_p R_o (C_{dl} + C_o)}{R_p + R_o}\right| - \log|(j\omega C_o R_o + 1)| - \log|(j\omega C_{dl} R_p + 1)|$$

The phase shift is given by equation $$\theta(\omega) = \angle Z(\omega) - \angle\left(1 + j\omega \frac{R_p R_o (C_{dl} + C_o)}{R_p + R_o}\right) - \angle(1 + j\omega C_o R_o) - \angle(1 + j\omega C_{dl} R_p)$$

Case A: CdlRp>>CoRo or CdlRp<<CoRo

Figure 11:
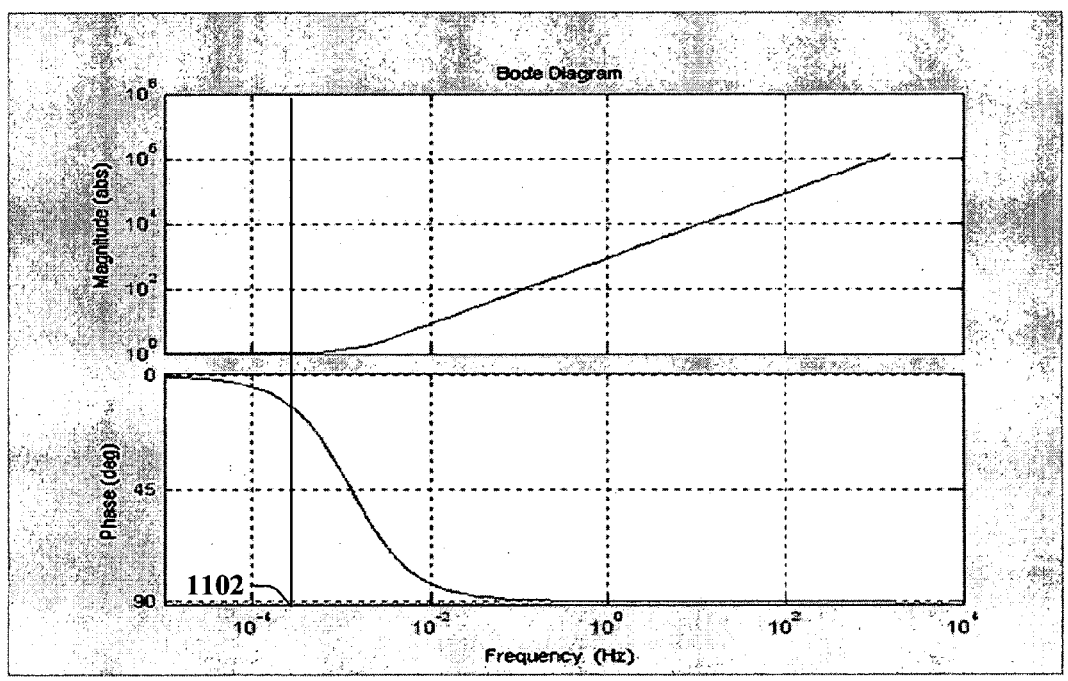
FIG. 11 is a Bode plot of the frequency response of the second term in the equation.
Figure 12:
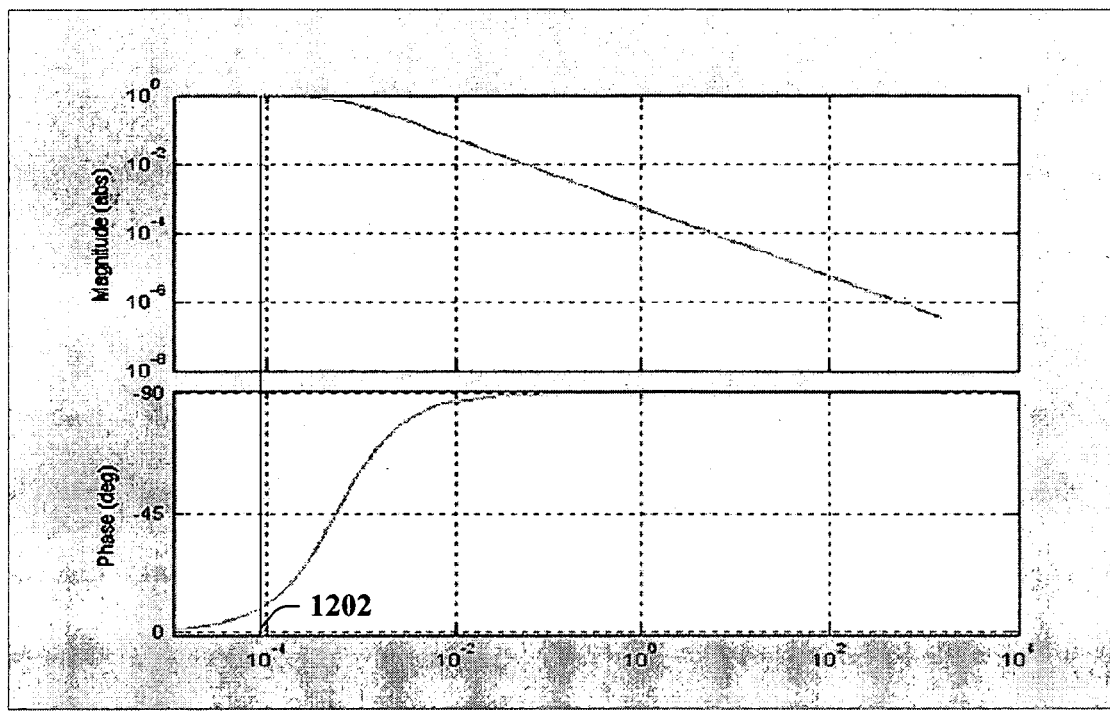
FIG. 12 is a Bode plot of the frequency response of the fourth term in the equation.
Figure 13:
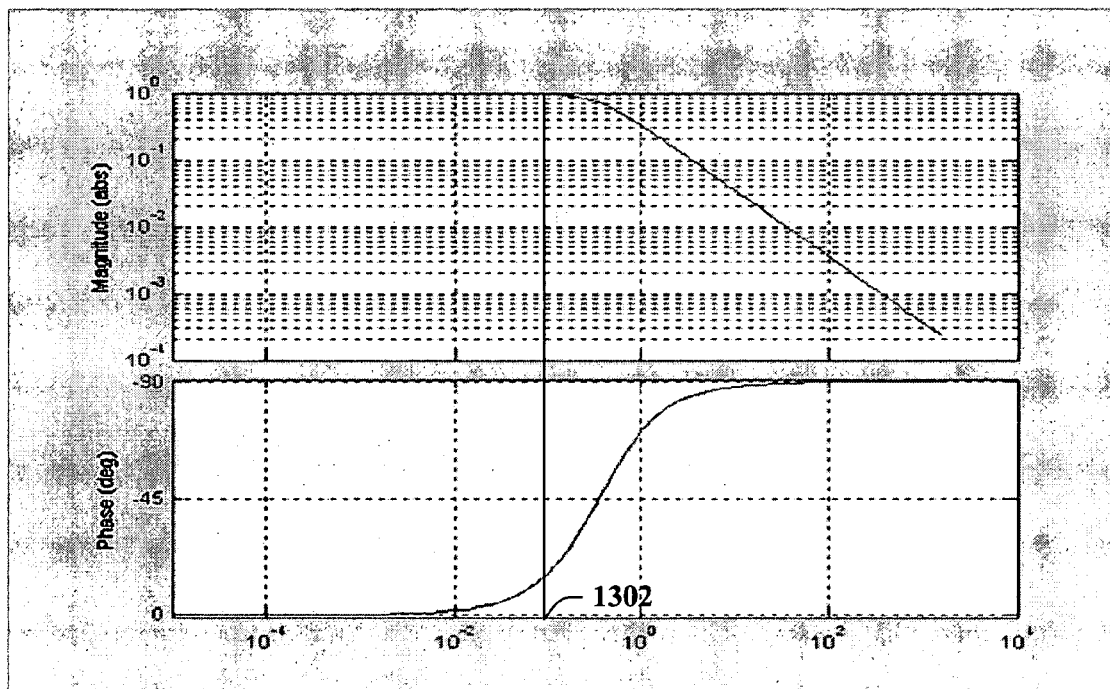
FIG. 13 is a Bode plot of the frequency response of the third term in the equation.

In the case where $C_{dl} R_p$ is significantly different from $C_o R_o$, the frequency response of the system displays two relaxations as shown in FIG. 6. By plotting the frequency response of the system using a log scale, it is easy to study the effect of the model parameters on the frequency response of the model because multiplication of magnitudes is converted into addition. The Bode plots in FIGS. 10-13 show the frequency response of each component of the two equations above. The break or corner frequencies are indicated by $$\text{``1102''} = \frac{R_p + R_o}{R_p R_o (C_{dl} + C_o)}$$

rad/s in FIG. 11, $$\text{``1202''} = \frac{1}{C_{dl} R_p}$$

rad/s in FIG. 12 and $$\text{``1302''} = \frac{1}{C_o R_o}$$

in FIG. 13.

Figure 15:
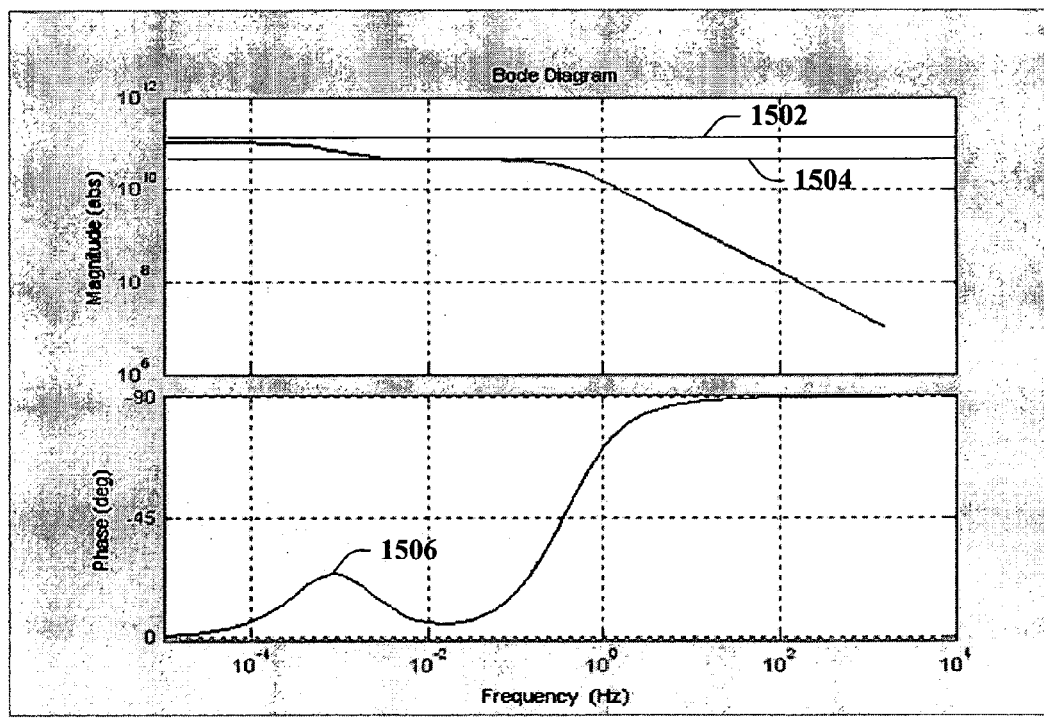
FIG. 15 is a Bode plot of the electrode-lubricant model with two plateaus.

It is apparent from the plot in FIG. 15 that the first plateau of the magnitude or the magnitude of the impedance at low frequency (indicated by line 1502) is actually log $|R_P + R_o|$.

|the first plateau|=log|$R_o + R_p$|

The magnitude of the second plateau in FIG. 15 (indicated by line 1504) can be estimated by considering the breaking frequencies of the components $$\log\left|\left(1 + j\omega\frac{R_p R_o (C_{dl} + C_o)}{R_p + R_o}\right)\right|$$

and $\log|1+j\omega C_{dl}R_p|$. The magnitude of the system is decreased between these two frequencies. Because asymptotes of the magnitudes of these two component have slopes of 1 and −1, respectively, the second plateau of the magnitude plot starts at approximately the frequency equal to $$\log\frac{R_p + R_o}{R_p R_o (C_{dl} + C_o)}$$

rad/s. At this frequency the magnitude of the system is approximately:

|the second plateau| =

$$\log|R_p + R_o| - \log\frac{R_p + R_o}{R_p R_o (C_{dl} + C_o)} - \log\frac{1}{C_{dl}R_p} = \log|R_p + R_o| -$$
$$\log|R_p + R_o| + \log R_p + \log R_o + \log(C_{dl} + C_o) - \log C_{dl} - \log R_p$$

By assuming that $C_{dl} \gg C_o$, the magnitude of the second plateau is approximately equal to the log of the bulk lubricant layer resistance.

|the second plateau| ≈ log $R_o$

Therefore, the bulk lubricant layer resistance and the resistance of the electrode-lubricant interface can be estimated by using the magnitude of the first and the second plateaus.

Figure 14:
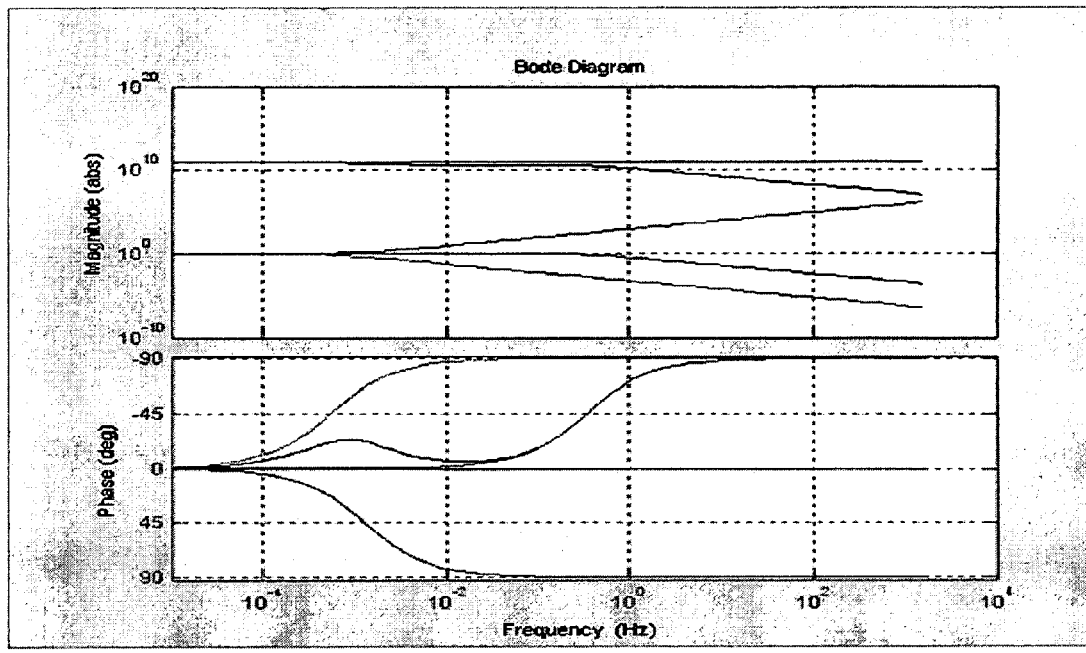
FIG. 14 is a Bode plot of the frequency response of the entire equation.

Considering the response of the system in the higher frequency range (>1 Hz), the slope of the magnitude is −1 and phase shift is −90 degree. This response of the system clearly results from the capacitance of the lubricant layer $C_o$ as shown in FIG. 14.

By assuming that $C_{dl} \gg C_o$, at high frequency, $$Z_{total} = Z_{Co} = \frac{-j}{\omega C_o} \text{ and } \log|Z_{total}| = \log\left[\frac{1}{\omega C_o}\right] = -\log(\omega) - \log(C_o)$$

Note that the Bode plot of $\log|Z_{total}|$ and $\log(f)$ or $\log(\omega)$ has a slope of −1 in the higher frequency range. At the point that f=0.16 Hz, ω=1 rad/s and log(ω=1)=0, so the second equation above becomes $$\log|Z_{total}(\omega=1)| = -\log(C_o)$$

$$C_o = \frac{1}{|Z_{total}(f = 0.16 \text{ Hz})|}$$

Therefore, the capacitance of the bulk lubricant layer can be estimated by extrapolating the magnitude curve with slope of −1 to the log |Z| axis at f=0.16 Hz.

The estimation of $C_{dl}$ can be estimated by considering the peak of the phase shift curve as indicated in FIG. 15. However, it is difficult in practice to locate the peak 1506 from EIS data because of the limitation of low frequency sampling. The estimation of $C_{dl}$ may be accomplished using a numeral method to fit the phase shift response.

Case B: RpCdl≦RoCo or RpCdl≧RoCo

Figure 16:
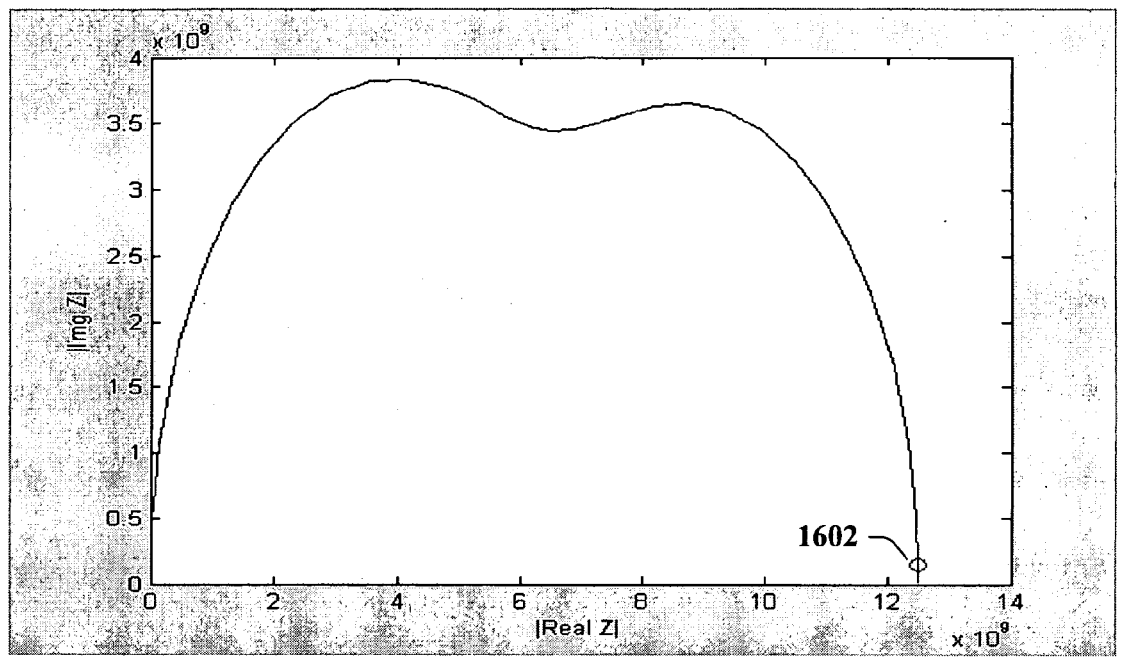
FIG. 16 is a Nyquist plot of the electrode-lubricant model in the case where $R_p C_{dl}$ is not significantly different from $R_o C_o$.
Figure 17:
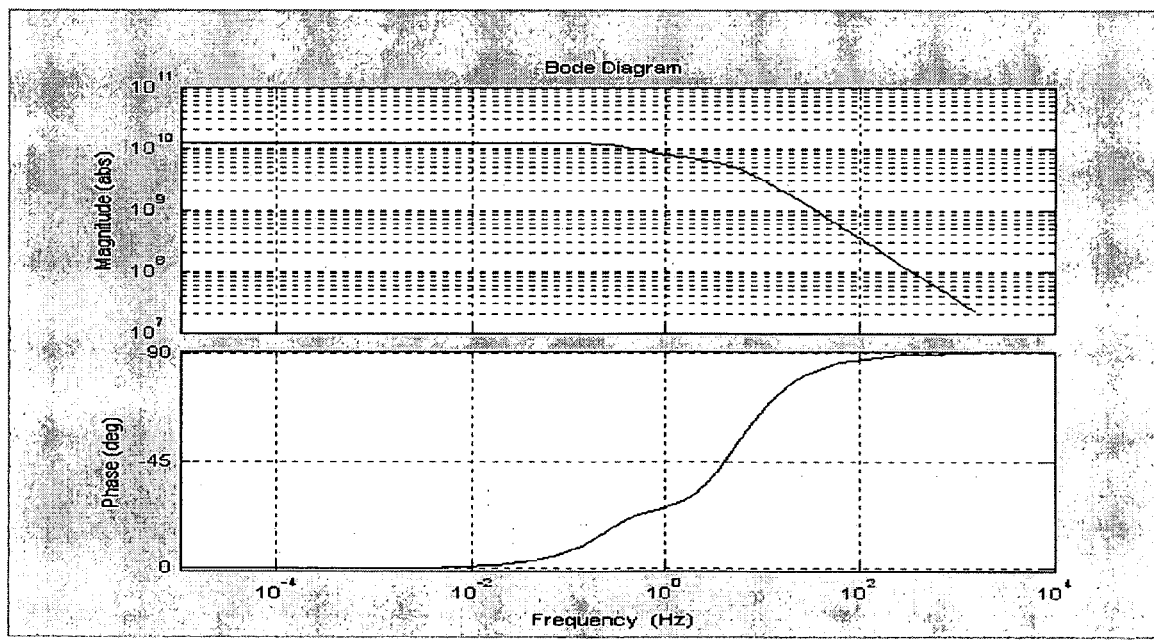
FIG. 17 is a Bode plot of the electrode-lubricant model in the case where $R_p C_{dl}$ is not significantly different from $R_o C_o$.

In the case where $R_p C_{dl}$ is not significantly different from $R_o C_o$, such as when $R_p$=6.0×10$^9$Ω, $C_{dl}$=6.0×10$^{-11}$ F, $R_o$=6.5×10$^9$Ω and $C_o$=5.0×10$^{-12}$ F, the frequency response of the system is similar to the response of a single parallel RC circuit as shown in FIG. 15. The Nyquist plot in FIG. 16 shows the complex-plane curve as a modified form of semi-circular shape. In this case, the circle 1602 indicates the impedance at 0.01 Hz and the diagram indicates that the frequency response of the system could be composed of, at least two semicircles. The semicircles exhibit a high overlapping degree. By considering the frequency responses, it is evident that the component $\log|1+j\omega C_o R_o|$ mainly contribute to the frequency response of the system in the high frequency range. Therefore, the capacitance of the bulk lubricant layer can be estimated by extrapolating the magnitude curve with slope of −1 to the log |Z| axis at f=0.16 Hz. Then log |$R_p$+$R_o$| can be estimated from the magnitude plot at the lower frequency end.

However, it is difficult in practice to extract $C_o$ or $C_{dl}$ from EIS data for this case because all model parameters are unknown. The sum of the capacitances $C_o$ or $C_{dl}$ of the two capacitors in series can be estimated by extrapolating the magnitude curve with slope of −1 to the log |Z| axis at f=0.16 Hz.

$$C_o = \frac{1}{|Z_{total}(f = 0.16 \text{ Hz})|}, C_{total} = \frac{1}{\frac{1}{C_{dl}} + \frac{1}{C_o}}$$

This case demonstrates how difficult it is to extract information from the EIS data when $C_{dl}R_p$ is not significantly different from $C_o R_o$. The analysis of the system response can be achieved by using modulus M*(ω) formalism in order to further investigate electrode polarization and the conductivity relaxation time. The modulus representation might show a clearer picture of the polarization phenomena than impedance. Modulus is derived from impedance data by the following:

$$M^*(\omega) = j\omega C_V Z^*(\omega)$$

where, CV is the vacuum capacitance of the cell and Z*(ω) is the EIS data.

The Data Fitting Method for Analyzing the Impedance Measurements

The study of M*(ω) and Z*(ω) may not provide any advantage for model parameter extraction from EIS data. A powerful tool to derive the equivalent electrical components of the bulk layer of lubricant and the interface is the theoretical "deconvolution" of the electrical response. The impedance measurements are analyzed by fitting the impedance spectrum to an equivalent circuit. The fitting method is called circuit description code (CDC).

From the study of the sensor prototype described in Section 4, the EIS data was investigated by using a nonlinear least squares fit procedure. The initial guess of the model parameters are derived by the following procedures:

First, estimating $R_p$+$R_o$ and assigning an initial guess of $R_o$ is performed by using the maximum |Z″|. This maximum |Z″| is approximately equal to the radius of the first semicircle, which is directly related to the resistance of the bulk lubricant layer. The initial guess of $R_o$ is given by the following equation:

$$R_o \sim 2*|Z''|_{max}$$

Then, $R_p$ can be estimated.

Secondly, estimating $C_{total}$ with the initial guess of $C_{dl}$ and $C_o$ given by the following:

$$C_{dl} \sim C_o \sim 2C_{total}$$

Figure 18:
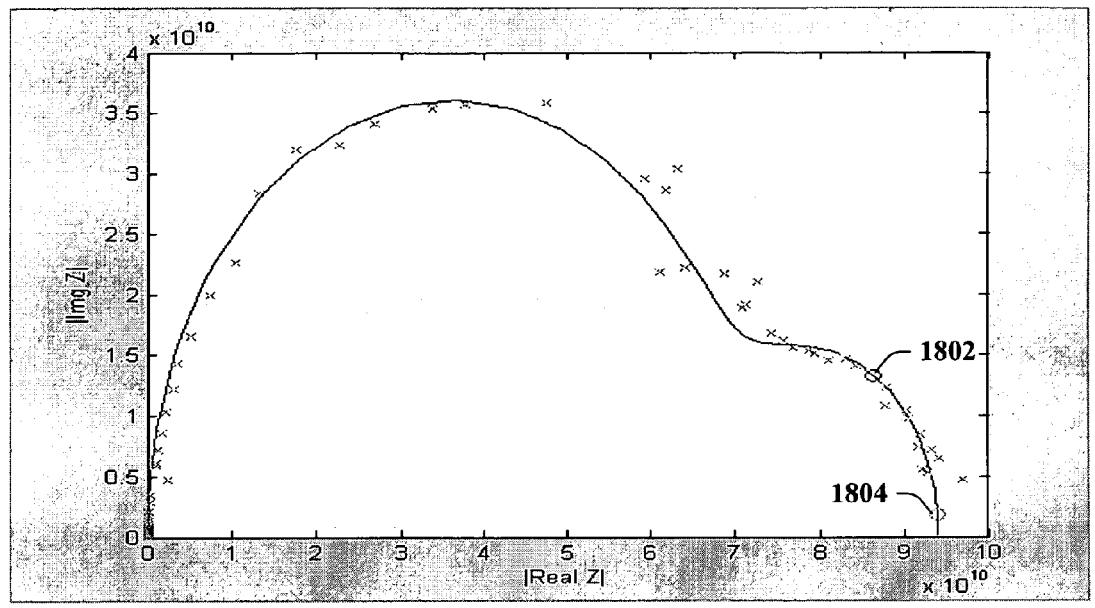
FIG. 18 is a Nyquist plot of the electrode-lubricant model manually fit the impedance data of new fresh oil.
Figure 19:
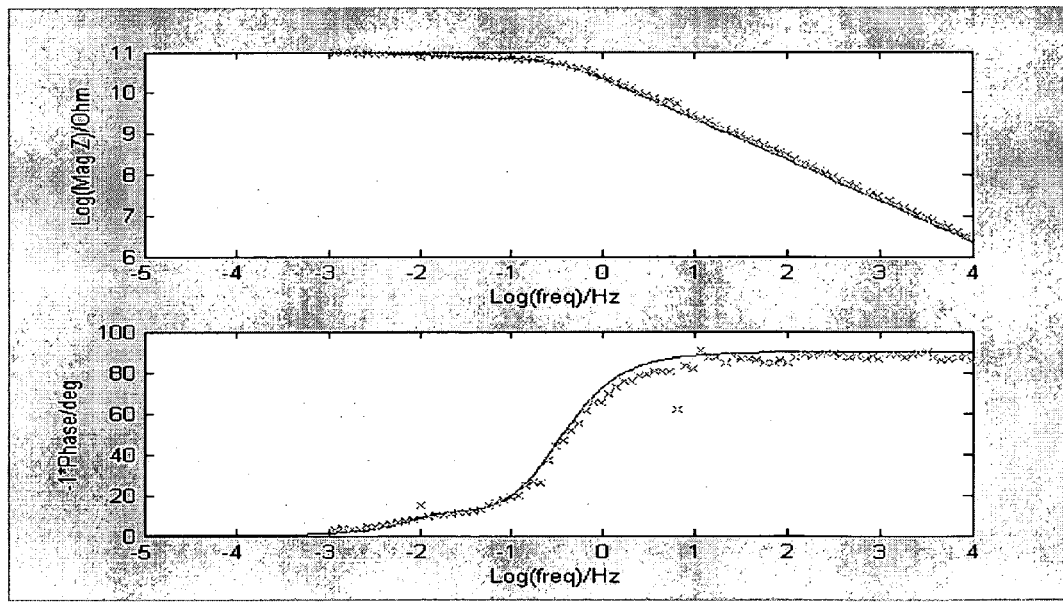
FIG. 19 is a Bode plot of the electrode-lubricant model manually fit the impedance data of new fresh oil.
Figure 20:
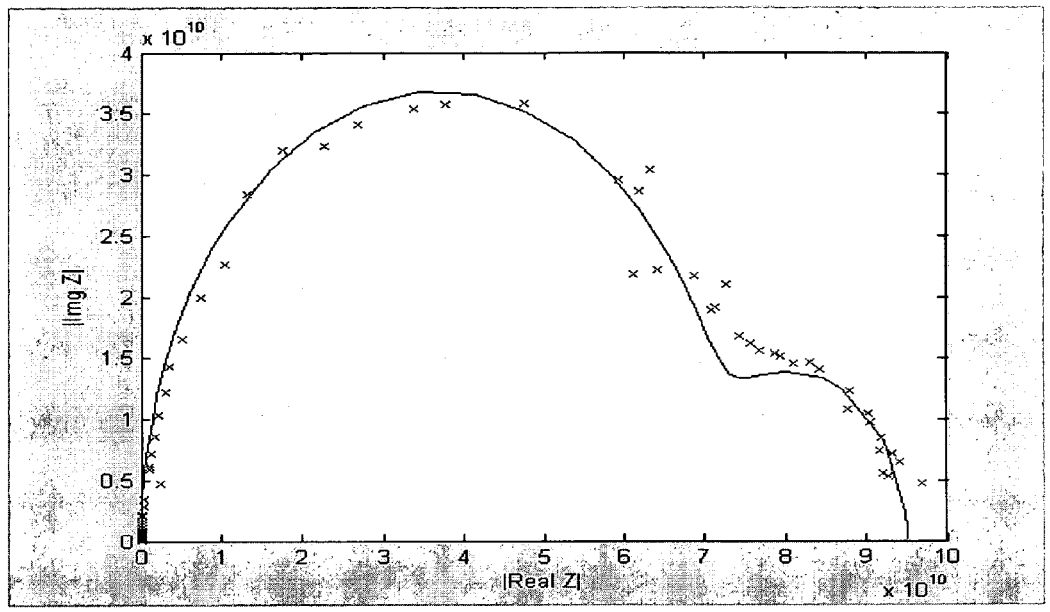
FIG. 20 is a Nyquist plot of the electrode-lubricant model using the nonlinear least squares method for the impedance data of new fresh oil.
Figure 21:
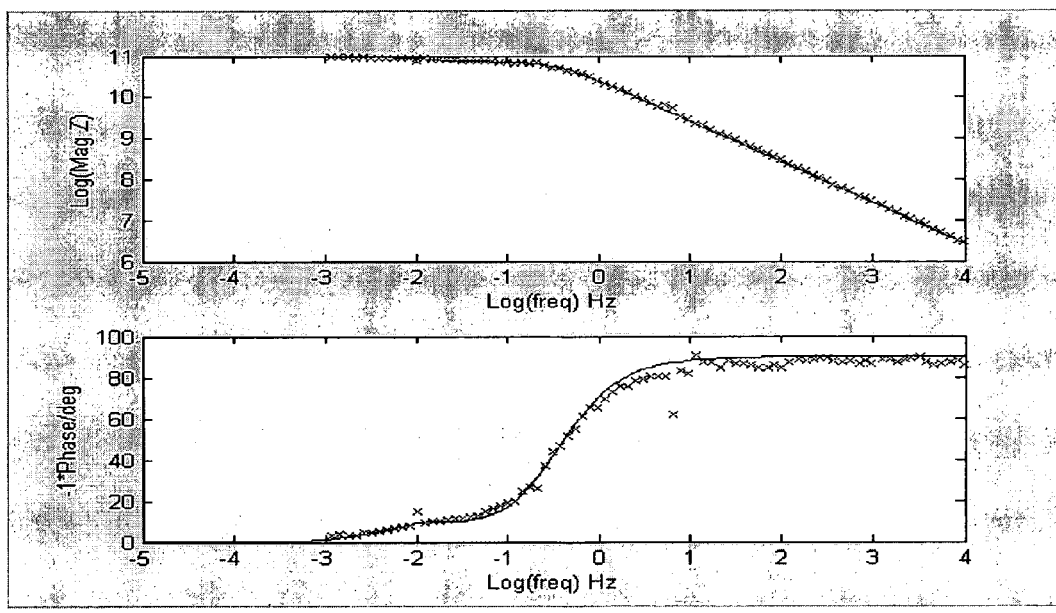
FIG. 21 is a Bode plot of the electrode-lubricant model using the nonlinear least squares method for the impedance data of new fresh oil.

Considering the Nyquist plot in FIG. 18, the complex-plane curve is generated manually by trial and error to fit the impedance data of new fresh oil from 10 kHz to 10 mHz, wherein circle 1802 indicates the impedance at 10 mHz and the circle 1804 indicates the impedance at 1 mHz. The Bode plot in FIG. 19 shows a good fit between the EIS data and the model. The diagrams in FIGS. 20 and 21 show a good fit between the new fresh oil EIS data and the model by using the nonlinear least squares method. The optimization process took 36 iterations to discover the best fit model parameters. The model parameters extracted from the trial-error process and the nonlinear least square method are listed in the table below.

This non-ideal capacitance is called a Constant Phase Element (CPE). The impedance of such a non-ideal capacitance is represented by:

$$Z_{CPE} = \frac{1}{Q(j\omega)^n},$$

where the parameter Q and $n \leq 1$ represent the non-ideal capacitance parameters, when n tends to 1, the parameter Q tends to C, and we obtain the model for ideal capacitance. This non-ideal characteristic of the capacitive effect is thought to be due to the roughness of electrode surface or caused by the heterogeneity of the electrode surface.

Tables 2 and 3 show the electrode-lubricant model parameters extracted from the impedance (EIS) data of used oil samples. The impedance data is measured by using a prototype sensor #1 (PS1) and a prototype sensor #2 (PS2). The conductivity of the oil samples (k) is also measured using an Emcee 1152 conductivity meter. Oil analysis laboratories use this meter for lubricant conductivity test. The meter applies a constant DC voltage and measures the DC current. The conductivity reading is ready after 3 seconds with an error of ±0.1 Pico S/m.

TABLE 2

Model Parameters from Impedance Measurement of Oil Samples by PS1 Sensor

| Sample Code | $Ro(\Omega)$ | $Co(F)$ | $Rp(\Omega)$ | $Cd1(F)$ | $k(S/m)$ | Cell constant($m^{-1}$) |
|---|---|---|---|---|---|---|
| New oil | $7.73 \times 10^{10}$ | $7.9 \times 10^{-12}$ | $6.05 \times 10^{10}$ | $1.08 \times 10^{-10}$ | $87 \times 10^{-12}$ | 6.72 |
| L0617-01 | $1.70 \times 10^{10}$ | $7.76 \times 10^{-12}$ | $1.54 \times 10^{10}$ | $1.39 \times 10^{10}$ | $891 \times 10^{-12}$ | 15.47 |
| L0617-02 | $2.41 \times 10^{10}$ | $7.89 \times 10^{-12}$ | $2.17 \times 10^{10}$ | $1.32 \times 10^{10}$ | $556 \times 10^{-12}$ | 13.39 |
| L0613-01 | $2.07 \times 10^{10}$ | $8.25 \times 10^{-12}$ | $2.069 \times 10^{9}$ | $1.26 \times 10^{-10}$ | $722 \times 10^{-12}$ | 14.94 |

TABLE 3

Model Parameters from Impedance Measurement of Oil Samples by PS2 Sensor

| Sample Code | $Ro(\Omega)$ | $Co(F)$ | $Rp(\Omega)$ | $Cd1(F)$ | $k(S/m)$ | Cell constant($m^{-1}$) |
|---|---|---|---|---|---|---|
| New oil | $7.23 \times 10^{10}$ | $6.17 \times 10^{-12}$ | $2.28 \times 10^{10}$ | $6.38 \times 10^{-10}$ | $87 \times 10^{-12}$ | 6.29 |
| L0617-01 | $1.57 \times 10^{10}$ | $7.07 \times 10^{-12}$ | $9.43 \times 10^{10}$ | $2.40 \times 10^{10}$ | $891 \times 10^{-12}$ | 13.98 |
| L0617-02 | $2.10 \times 10^{10}$ | $6.51 \times 10^{-12}$ | $1.14 \times 10^{10}$ | $2.17 \times 10^{10}$ | $556 \times 10^{-12}$ | 11.67 |
| L0613-01 | $1.64 \times 10^{10}$ | $6.91 \times 10^{-12}$ | $9.70 \times 10^{9}$ | $2.57 \times 10^{-10}$ | $722 \times 10^{-12}$ | 11.84 |

TABLE 1

Model Parameters Extracted from Fresh Oil EIS Data

| Method | $Ro(\Omega)$ | $Co(F)$ | $Rp(\Omega)$ | $Cdl(F)$ |
|---|---|---|---|---|
| Manual Trial and Error | $7.0 \times 10^{10}$ | $7.0 \times 10^{-12}$ | $2.4 \times 10^{10}$ | $4.5 \times 10^{-10}$ |
| Nonlinear Least Square | $7.23 \times 10^{10}$ | $6.17 \times 10^{-12}$ | $2.28 \times 10^{10}$ | $6.38 \times 10^{-10}$ |

The data fitting procedure can be improved by replacing the ideal capacitances $C_{dl}$ and $C_o$ with non-ideal capacitances.

Figure 22:
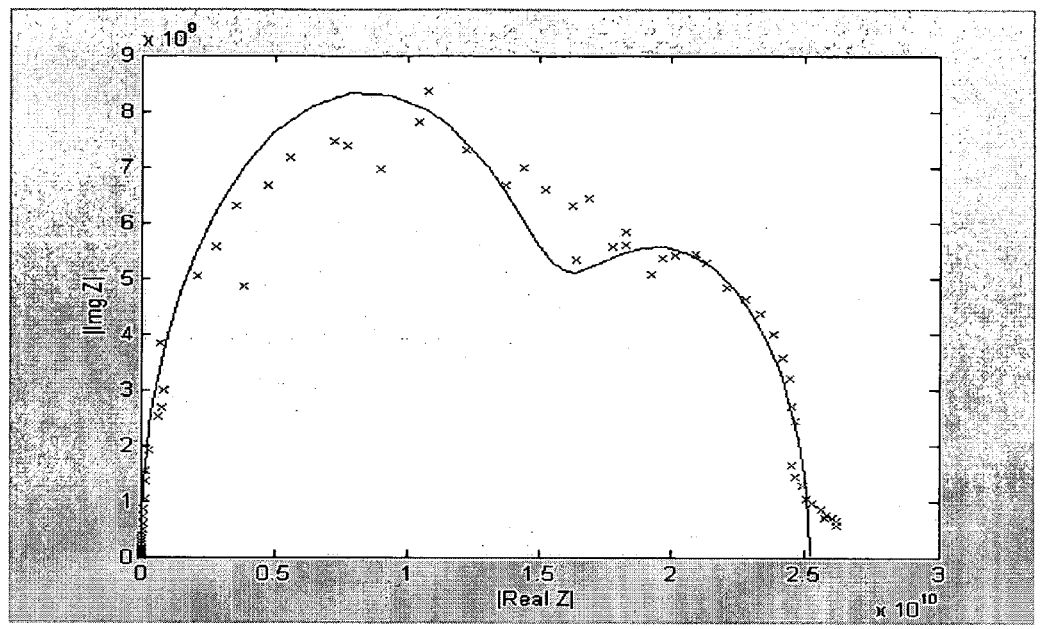
FIG. 22 is a Nyquist plot of the electrode-lubricant model using the nonlinear least squares method for the impedance data of used oil.
Figure 23:
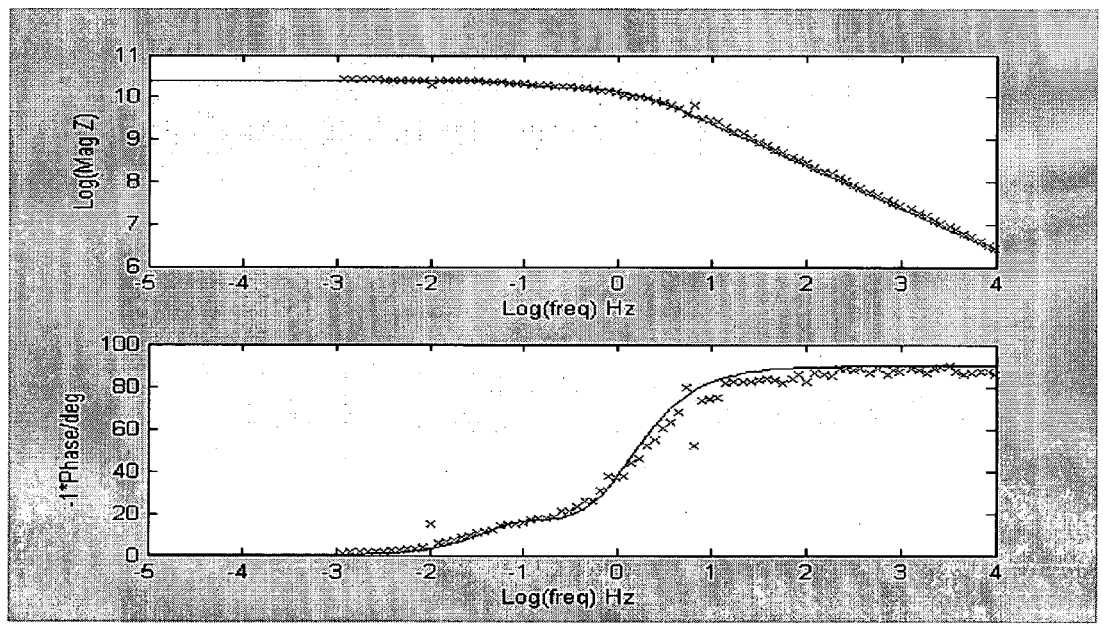
FIG. 23 is a Bode plot of the electrode-lubricant model using the nonlinear least squares method for the impedance data of used oil.

It has been determined that the impedance of the prototype sensor PS1 can detect changes in the electrical properties of the used oil samples. Similar results were also found using the PS2 sensor. The diagrams in FIGS. 22-23 show the fitting of the complex-plane curve and the Bode plot to the EIS data of the sample oil measured by the PS2 sensor, where $R_o=7.23 \times 10^{10} \Omega$, $C_o=6.17 \times 10^{-12}$ F, $R_p=2.28 \times 10^{10} \Omega$ and $C_{dl}=6.38 \times 10^{-10}$ F. by using a nonlinear least squares method.

The cell constants of PS1 and PS2 shown in Table 2 and Table 3 are computed in order to determine if PS1 and PS2 are operating in the linear range. The results show that PS1 and PS2 have approximately the same cell constant except during the new fresh oil measurement. The high resistivity of new fresh oil may cause a reduction in the effective area of the electrodes (A). If the entire electrode area is the effective area, the expected cell constant value is $$\frac{1 \times 10^{-3}\ m}{(2 \times 4.5 \times 2) \times 10^{-6}\ m^2} = 55.5\ (m^{-1}).$$

The cell constants in Table 2 and Table 3 indicate that the real effective area is larger than the expected electrode area. A better way to determine the cell constant is by using a sensor for which the electrode space d is adjustable. The resistivity of the lubricant can be determined by the slope of $R_o$ and d. The cell constant is then given by the ratio between lubricant resistance and lubricant resistivity.

The results shown in Table 2 and Table 3 verify that the nonlinear least squares method with a good initial approximation of the model parameters is a suitable tool for the electrode-lubricant model parameters extractions.

MEMS Impedance Sensor Test with KCL Solution

Potassium Chloride solution (KCl) is frequently used as a standard solution for conductivity measurement test. The table below shows a standard of KCl solution (JIS Ko102).

TABLE 4

Standard KCl solution (JIS KO102)

| Standard KCl solution | Conductivity (mS/cm) at 25 C. | Grams of KCl/liter of solution |
|---|---|---|
| A | 111.34 | 74.2460 |
| B | 12.86 | 7.4365 |
| C | 1.409 | 0.7440 |
| D | 0.147 | 0.0744 |

The impedance MEMs sensor was tested with a Standard KCL solution by using an electrochemical workstation (CH Instruments Model 660B). The applied ac voltage has 10 mV magnitude and was varied from 0.01 Hz to 100 kHz. The Randles equivalent circuit model is suitable for modeling the MEMS sensor electrode-KCl system. The bulk resistance of KCl can be estimated using the high frequency impedance with a phase shift of zero degrees. The estimated resistances of the KCl test solutions are listed in Table 5. The KCl test solutions were also tested with a Yellow Springs Instrument (YSI) model 35 conductivity meter. The conductivity readings are listed in Table 5. According to the test results, the resistance readings from the MEMS sensor increases from the KCl solution B test to the KCl solution D test. These results indicate that the design of the MEMS impedance sensor is proper for fluid conductivity measurements.

TABLE 5

MEMS impedance sensor B5 test results with standard KCl solutions

| Standard solution | Measured KCL Resistance | Actual Conductivity reading | Computed Cell constant |
|---|---|---|---|
| KCl solution B | <3.98 × 10³ Ω | 11.66 mS/cm | <46.40 (cm⁻¹) |
| KCl solution D | 3.98 × 10⁴ Ω | 0.1386 mS/cm | 5.51 (cm⁻¹) |

Conductivity data was also accumulated for water contaminated hydraulic fluids. In addition, detection of metal wear by way of, e.g., electrochemical analysis can be employed in connection with the sensor, (e.g., sensor 106 of FIG. 1). For example, the sensor can detect and/or identify metal ion species, the amount present, etc., which can then be employed to diagnose a current state 110 and estimate a future state 112. As well, many other parameters of a fluid can be detected, some of which are listed in Table 6 below:

TABLE 6

Lubricant Analysis of Gearbox Oil Samples

| Sample Code | Hours of operation | K (Pico S/m) | TAN (Mg KOH/g) | Viscosity @ 40 C (cSt) | Wear Metal (ppm) | Water (% Vol) | Oxidation | Severity |
|---|---|---|---|---|---|---|---|---|
| Samples include new MIL-L-23699 oils and degraded samples of this gear oil aged in a gearbox under conditions of elevated temperature and elevated torsion loading of the gearbox during operation at nominal speed. | | | | | | | | |
| New | 0 | 87 | | | | | | |
| L0528-00 (reference) | 0 | | 0.04 | 25.4 | 0 | Nil | 0.673 | Normal |
| L0528-01 | 3.9 | 321 | | | | | | |
| L0528-02 | 6.6 | 346 | | | | | | |
| L0529-01 | 9.8 | 313 | | | | | | |
| L0529-02 | 13.6 | | 0.34 | 228.7* | Iron 4 | Nil | 0.573 | Moderate |
| L0529-03 | 17.3 | 328 | | | | | | |
| L0530-01 | 20.1 | 301 | 0.38 | 61.0* | Iron 4 | Nil | 0.618 | Moderate |
| L0530-02 | 27.2 | 235 | | | | | | |
| L0602-01 | 32.9 | | 0.29 | 58.2* | Iron 2 | Nil | 0.616 | Moderate |
| L0603-01 | 35.9 | 360 | | | | | | |
| L0603-02 | 40.6 | | 0.43 | 97.0* | Iron 1 | Nil | 0.606 | Moderate |
| L0604-01 | 49.0 | 709 | | | | | | |
| Oil samples from gearbox with load = 1.3 | | | | | | | | |
| L0612-00 (reference) | 0 | | 0.03 | 25.3 | 0 | Nil | 0.667 | Normal |
| L0613-01 | 3.2 | 722 | | | | | | |
| L0613-02 | 5.7 | | 0.08 | 25.4 | Iron 21 | Nil | 0.677 | Observation |
| L0613-03 | 8.2 | 957 | | | | | | |
| L0613-04 | 9.7 | 831 | 0.08 | 25.4 | Iron 19 | Nil | 0.675 | Observation |
| L0617-01 | 12.7 | 891 | | | | | | |

TABLE 6-continued

Lubricant Analysis of Gearbox Oil Samples

| Sample Code | Hours of operation | K (Pico S/m) | TAN (Mg KOH/g) | Viscosity @ 40 C (cSt) | Wear Metal (ppm) | Water (% Vol) | Oxidation | Severity |
|---|---|---|---|---|---|---|---|---|
| L0617-02 | 33.7 | 556 | 0.10 | 25.3 | Iron 209<br>Tin 1<br>Nickel 1<br>Manganese 2 | Nil | 0.680 | Severe |

Note: the viscosity result may not be relevant, the sample separated into two layers during the viscosity test
*Conductivity is measured with the conductivity meter Electrochemical Sensors An important and versatile sensor element in the multi-element fluid sensor is the electrochemical sensor element. This can be a two-electrode or three-electrode sensor element that determines the fluid's capacity for gaining or losing electrons. While a pH sensor can characterize the relative state of the system for receiving or donating hydrogen ions (e.g., base or acid characterization), the oxidation-reduction potential is affected by all oxidizing and reducing agents in the fluid, including hydrogen ions. This characteristic makes the electrochemical sensor responsive to a wide range of agent types in the fluid. However, it also makes it more difficult to establish the contaminant or fluid species that is responsible for the observed ion exchange. Using cyclic-voltammetry methods and subsequent analysis of the sensor response it is possible to identify the characteristic features of water, additives, or other unique species. The existence of many compounds and unknown elements makes it impossible to identify the specific agent or agents contributing to the reduction-oxidation activity. It is possible to uniquely identify a known possible contaminant in a known fluid using knowledge of the reduction potential of the component to be identified. When the range of possible contaminants is large or when contaminants have very similar reduction potential values it is not possible to uniquely distinguish the species present or the amount present. It is possible however to combine results from the conductivity sensor and pH/TAN sensor with the electrochemical sensor using sensor fusion (described infra) to significantly enhance both the diagnostic and species detection capabilities of the electrochemical sensor. For example, the presence of water in oil will give a characteristic "fingerprint" in each sensor element response. This information may be combined to establish the presence of water or the probable presence of water in combination with another contaminant.

Since the electrochemical sensor response is affected by all ion transfer activity, regardless of the source, the electrochemical sensor response may also be affected by the presence of metal ions in solution. Thus, the process of metal wear in a lubricating fluid produces metal ions as well as metal particulates. Therefore, an electrochemical sensor may be able to provide an extremely valuable indication of metal wear. The indication of metal wear may provide an earlier indication of excessive or unusual wear by identifying the specific wear ions present in the fluid. The ability to track the presence and rate of change of specific ions provides advantages over laboratory metal wear tests or on-line particle counters (e.g., optical tests) that are unable to discriminate particle species.

First, it can be determined the type of target metal ions to be detected. Accordingly, specifications for metal particulate size distribution by metal type likely to be in the fluid (e.g., fluid 104 of device 102 from FIG. 1) can be obtained. Similar data for, e.g., aircraft engines and transmissions have been compiled by the Department of Defense in the Joint Oil Analysis Program Manual (Volume III). For example, these specifications can show, e.g., that the maximum allowable increase of iron particles within a certain number of hours of operation is a certain value, such as, e.g., 9 ppm. Or, that the limit is, e.g., 3 ppm of iron in an engine and combining transmission within, e.g., a 10 hour operating window. Also, an increase of more than, e.g., 2 ppm of aluminum or chromium particles in any of the rotating systems/components/device within a 10 hour operating period can be catastrophic. For many applications there will be a positive correlation between metals present in ppm and the presence of ions of the same metal.

Based on the types of metals anticipated in lubricating oils a suite of calibrated oils with particular metallic and non-metallic ions present in known concentrations can be obtained. In addition to clean, new oil, individual samples with 1000 ppm of Iron, Chromium, Lead, Aluminum, Silicon, and Phosphorous can be obtained. FIG. 24 provides a fluid analysis summary that presents the test results for various fluid types to illustrate the types of information on the fluid samples including the source and quantity that can be obtained. Test results for the multi-element sensor are provided in the columns with the sensor identification label shown. Other fluid analysis results were obtained from Rockwell Automation laboratories or from outside commercial test laboratories. It is to be appreciated that the clean new oil permits diluting the samples with metal to lower concentrations of metal ions than what is shown in FIG. 24. The following describes the operation of the electrochemical sensor and the sensor's response to the metal ions in the calibrated oil.

Detection of ionic species in a medium, particularly in an aqueous environment, can be accomplished by electrochemical techniques. The oxidation or reduction of these ions can be carried out if the corresponding Gibbs free energy for the reaction can be provided (e.g., enough energy to carry out the reaction). The Gibbs Free Energy equation indicates the amount of energy that needs to be provided for the reaction to proceed so that the current could be measured. By imputing the voltage, multiplying it by the Faraday constant and the number of electrons transferred, the amount of energy needed to complete the reaction can be calculated.

This can be the operational principle of the amperometric measurement. Voltammetric measurement is also based on this similar principle. In this case, the applied potential increases linearly at a pre-determined rate over a pre-determined potential (voltage) window. The objective is to assess the possible oxidation or reduction reactions that may occur at different potentials within the applied voltage window.

In this study, the electrochemical sensor response is employed to establish the feasibility of using a voltammetric based electrochemical sensor for detecting metal ions in the lubricant. Two designs of the electrochemical sensor are used in this study. One design employs a two-electrode configuration, a working and a combined counter-reference electrode structure. The other design uses a three-electrode arrangement, a working, a counter, and a reference electrode. The working and the counter electrodes are platinum, and the reference electrode is sliver-sliver chloride (Ag/AgCl). Other metals may be used that also provide for an electrochemical response such as antimony or iridium.

Figure 25:
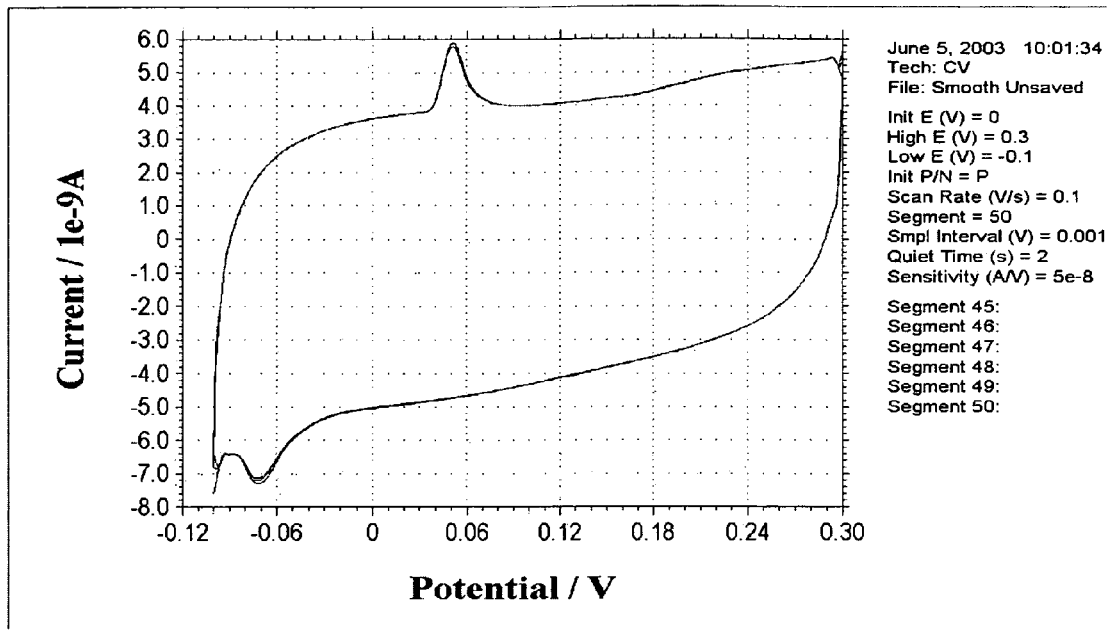
FIG. 25 is a plot of a Voltammogram of 0.1M NaCl Solution.

In a preliminary study, the fabricated sensor prototype is used to carry out a voltammetric study of a 0.1M NaCl solution. FIG. 25 shows the voltammogram that was obtained. It shows an oxidation peak occurring at 0.06 volts versus an Ag/AgCl reference electrode and a reduction peak at −0.07 volts versus an Ag/AgCl reference electrode. The voltage window is between −0.10 volts and +0.30 volts. The oxidation reaction corresponds to the oxidation of chloride ions in the solution. The reduction reaction is the reduction of chlorine (from the oxidation of chloride ions). This assessment shows the electrochemical sensor prototype performs well in an aqueous solution.

Figure 26:
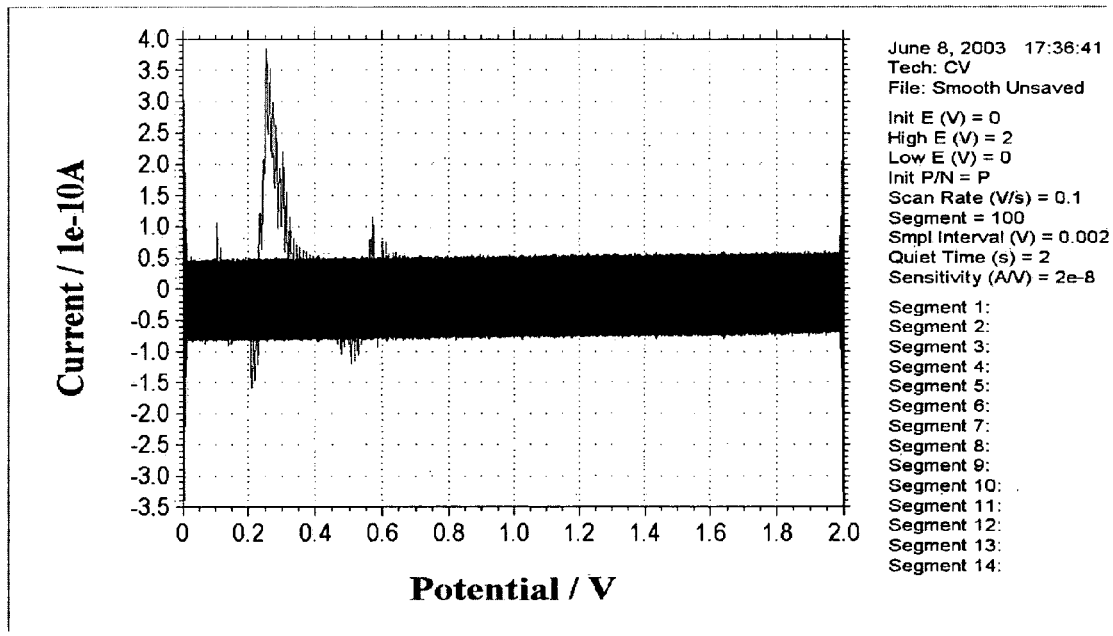
FIG. 26 is a plot of a Voltammogram of a base oil with 1,000 ppm aluminum.

The electrochemical sensor was used in specifically prepared oil samples using a base of mineral oil and containing known quantities of specific ions. FIG. 26 shows the voltammogram obtained in the base oil with 1,000 ppm (by weight) aluminum. Comparing to the figure above, as expected, the base oil shows a much higher resistivity (the thick black horizontal lines). However, there is an appreciable oxidation peak of the metal ion at +0.3v versus the Ag/AgCl reference electrode. The repeatability of this observation is good, even though quantification of the current produced is difficult due to the high degree of resistivity in the oil that results in a very noisy signal.

Figure 27:
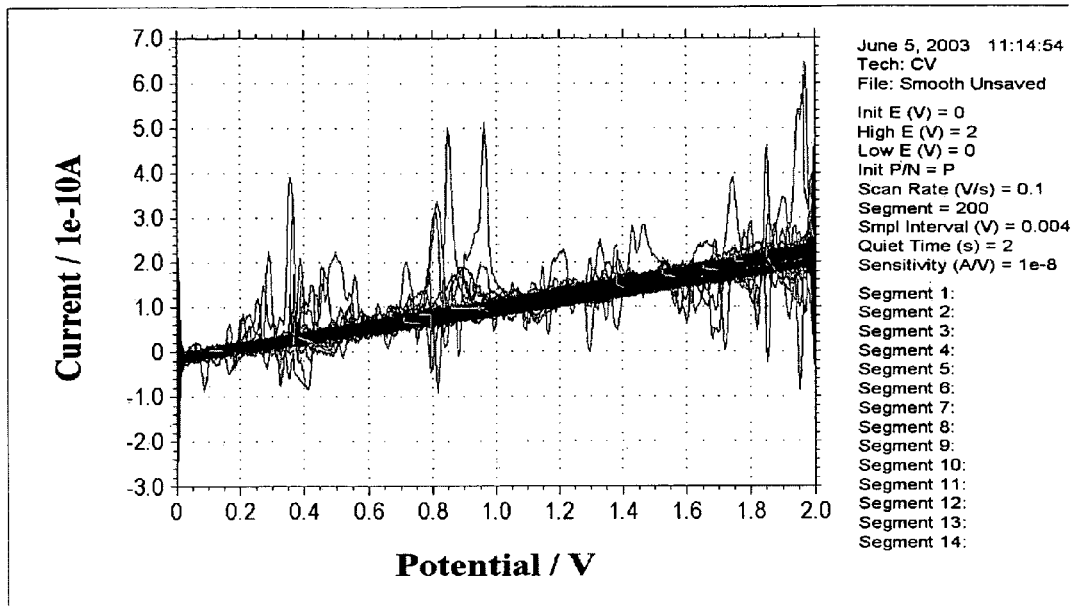
FIG. 27 is a plot of a Voltammogram of the base oil with 1,000 ppm chromium.

FIG. 27 illustrates a voltammogram obtained in the base oil containing 1,000 ppm of chromium. An oxidation peak at approximately 0.6v versus Ag/AgCl electrode is observed. This observation, similar to that shown in the figure above, is repeatable and semi-quantitative.

Figure 28:
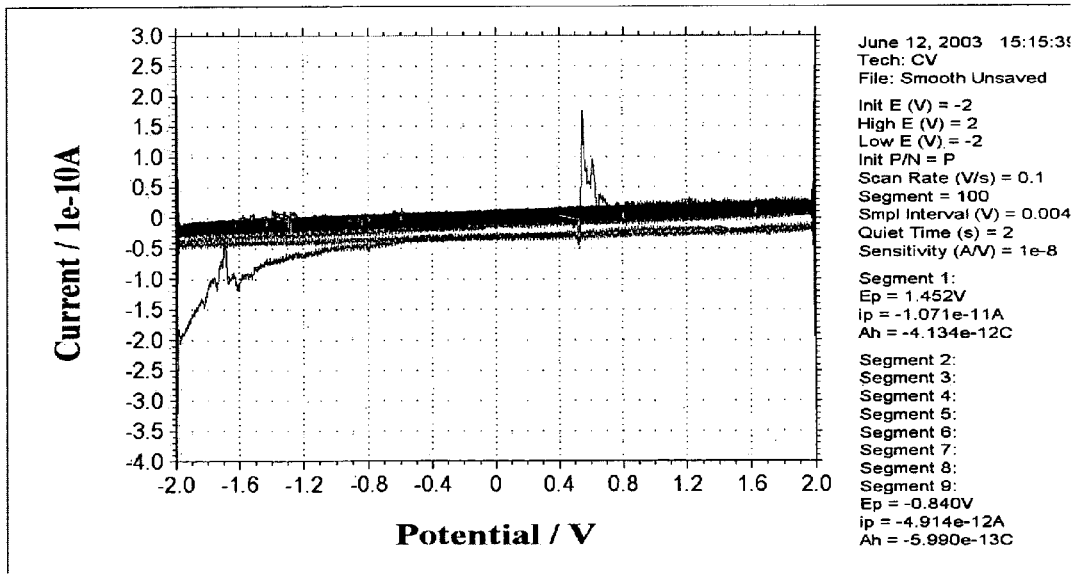
FIG. 28 is a plot of a Voltammogram of the base oil with 1,000 ppm iron.

FIG. 28 shows a voltammogram from the base oil containing 1,000 ppm of iron ions (sample #L0521-07). There are two distinguished oxidation peaks that occurred at 0.4v and 0.9v versus Ag/AgCl reference electrode. These oxidation reactions may be (1) oxidation of iron (zero valance) ions to ferrous ions, and (2) oxidation of ferrous ions to ferric ions respectively. However, this postulation requires further experimental investigation.

Figure 29:
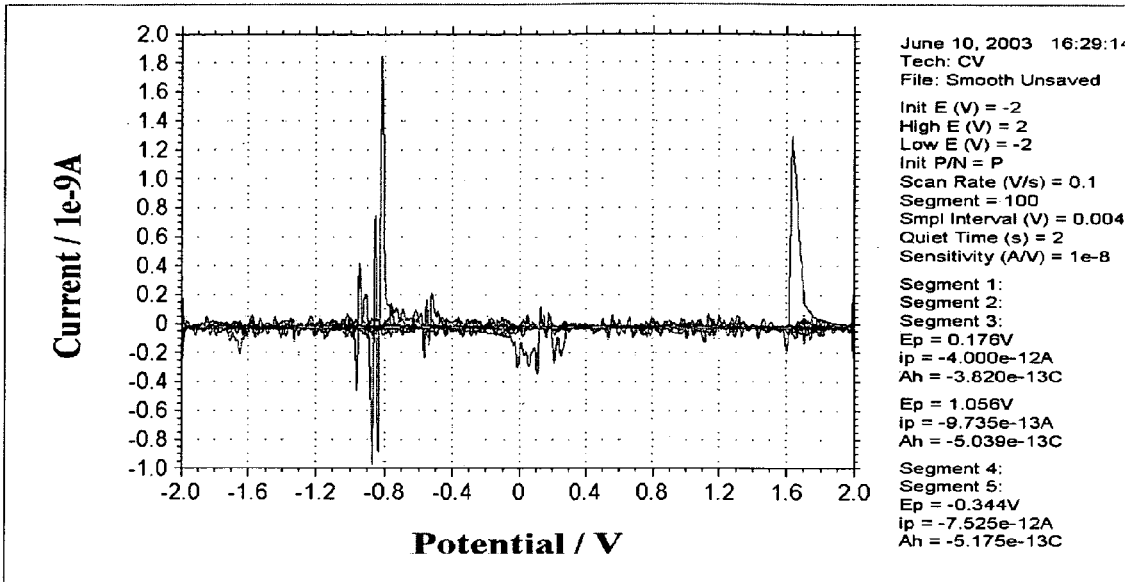
FIG. 29 is a plot of a Voltammogram of the base oil with 1,000 ppm phosphorus.
Figure 30:
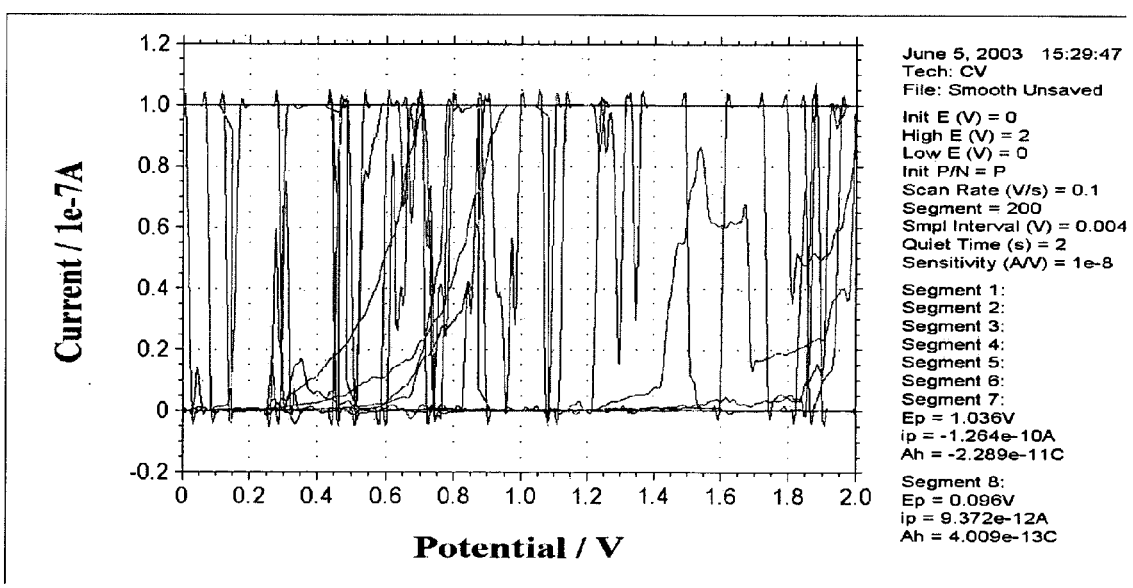
FIG. 30 is a plot of a Voltammogram of the base oil.

FIG. 29 shows a voltammogram obtained of base oil containing 1,000 ppm phosphorous. Two oxidation peaks, one at −0.8 volts and another at +1.5 volts versus Ag/AgCl electrodes are shown. The actual reaction mechanisms of the oxidation of phosphorous ions are not understood. However, the presence of the oxidation peak at those potentials is evident. FIG. 30 displays the voltammogram for the base oil (Lot 30, sample #L0521-01), and it does not show any specific presence of ions or species at any particular potential. Based on the exploratory results obtained, an oil sample with a specific ion shows a reaction peak at a specific potential. Because of the relatively high degree of resistivity of the oils or lubricant, quantitative assessment of the concentration level of the ions is difficult. In the presence of multiple species or ions, the identification of each of these species or ions is not feasible by this electrochemical technique alone.

Accordingly, an oil sample with specific metal ions present will exhibit a characteristic reaction peak at specific potentials or possibly several characteristic peaks. These peaks will correspond to the reduction potential of the elemental ions present. These results suggest that the electrochemical sensor may be able to detect elemental ions such as chromium, iron, aluminum, and phosphorous in lubricating fluids. The unique signature of the metal ions present will also support identifying the particular ionic species present in the fluid—or perhaps simply identifying or confirming the absence of ions in the fluid suggesting no excessive metal wear, fresh fluid, or a missing additive or depleted additive.

Because of the relatively high degree of resistivity of the oil or lubricant, it may be difficult to precisely establish the concentration level of the ions species present. In addition, since the electrochemical sensor response is affected by all ions in the fluid, it may be difficult or impossible to accurately identify all the specific ionic species present in the fluid particularly if the reduction potential is outside the range of voltage potential applied or if multiple ion species present in the fluid have. The use of this sensor in identifying specific species or ions in a less-conductive oil or lubricant medium may be enhanced by employing multiple sensors, sensors with ion-selective coatings (e.g., ion-selectric electrodes—ISE) and sensor fusion methods.

To analyze the metal content of degraded fluids samples that were extracted from a controlled gearbox experiment. An industrial gearbox filled with fresh, new gear oil and subsequently operated under high temperature and high load conditions. Periodically during gearbox operation fluid samples were extracted and analyzed as the fluid progressed from new fresh oil to fully degraded, blackened oil. Analytical laboratory test results confirmed the prevalence of metal species in the fluid. The type of metal in solution corresponds to the composition of the gearbox components that wear. It is significant that the electrochemical sensor was also able to detect and characterize silicon (Si) in oil. It will be very useful to also detect silicon as a contaminant. Operating, e.g., aircraft in hostile environments such as deserts may result in sand being introduced into the lubricant, hydraulic fluid, or fuel.

The electro-chemical sensor coupled with effective classification models and sensor fusion may provide a unique and extremely useful tool for real-time monitoring of machinery wear and machinery fault diagnostics. Correlating the electro-chemical metal ion response with the pH/TAN sensor and conductivity sensor response using sensor fusion can enhance the ability to detect and to discriminate metal ions in oil. This sensor element may provide a basis for detecting the earliest stages of wear and potentially discriminating the wear component and wear rate.

The use of contaminant selective coatings, ion-selective coatings, and bio-selective coatings or a combination of these can provide for enhanced sensitivity for detecting, classifying and/or quantifying elements that may be present in aqueous or non-aqueous fluids. For example, there is interest in detecting the build up of bacteria in water storage tower that occurs as water remains stored for prolonged periods, particularly in warm weather. The detection and quantification of undesirable chemical or biological agents can provide for enhanced protection for water distribution customers while avoiding the costly discard of water based only on water storage time. As another example, it is important to detect the presence of biological agents in vehicle fluids such as oil, hydraulic fluid, and fuel. Biological agents in fluids are undesirable and can affect machinery operation and personnel health. Hazardous levels of bacteria can occur as a result of bacterial growth or through malicious tampering of fluids such as through military action of hostile forces.

As such, specialized coatings applied to a sensor can protect the sensor from corrosive agents while facilitating detection and/or identification of certain biological agents. For example, the sensor can be coated with a material that includes an enzyme that reacts with a particular biological species or species by-product, and thus, facilitates detecting the presence, concentration, and growth rate of a biological species. Similarly, coatings (e.g., electrolytic coatings) that promote selective ion and/or electron transfer to the sensor can enhance the ability to detect small amounts of a targeted material, improve the detection accuracy, and provide more accurate concentration and rate of reaction information. Such coatings can be applied to the elements of a variety of different sensor types, e.g., dielectric, pH, and electrochemical elements may be coated with bio-selective material of an enzyme type and/or a molecular imprinting type and/or ion-selective or electron-transfer promoting coating. An electrochemical sensor may be operated in potentiometric mode or amperometric mode, and multiple sensor elements can employ different operating modes and with different coatings. Thus, the results for each element can be combined using sensor fusion (described infra).

The data shows that we can distinguish between gear oil, hydraulic fluid, and different types of fuel by using the bulk resistance value ($R_o$) extracted from the ac impedance data obtained from the conductivity sensor. The bulk resistance value of oil and the hydraulic fluid are similar. This is consistent with the data obtained from laboratory conductivity tests. The estimation of the interface resistance ($R_p$) and double layer capacitance ($C_{dl}$) are not as accurate and indicated for example by the double layer capacitance ($C_{dl}$) of the fluid. The electrical model of the interface for the conductivity sensor may be enhanced by providing additional laboratory tests to provide a more accurate model and/or selective coatings or electrolytic coatings in order to make this a more effective analytical tool. The bulk fluid properties ($R_o$ and $C_o$) that are used in the prognostics model (described infra) are very accurate.

These results indicate that conductivity results alone do not permit classifying all the cases for the gearbox test (Table 6). However, OCP and the conductivity (bulk and double layer electrical properties) and temperature may be readily integrated using sensor fusion to distinguish the degraded oil from new gear oil.

Prognostics

Determining the future condition or expected future is referred to as prognostics. This capability is important to maximize the value from machinery instrumentation and data analysis. Numerous industrial manufacturers have identified prognostics as the most critical information they can use from machinery monitoring. While diagnostics can provide information on the current condition of a system (e.g., current state 110) that may direct repair or maintenance action required, prognostic information (e.g., future state 112) can directly affect future investments, operating modes, missions, etc. Driving machinery health information to a decision support level provides the maximum impact and is directed at protecting machinery and processes from unexpected failures or catastrophic conditions. It has been determined that prognostics and system-level diagnostics (as opposed to component-level) are the top two objectives in condition-monitoring. Consistent with this level of importance, a specific objective of fluid sensor analysis is to establish reliable, robust models of fluid degradation that will ultimately be used to predict the future operating condition or remaining useful life of critical components. The prognostic model can also be used to investigate other future operating scenarios and establish operating and control options that may prevent an impending failure or alternatively, enable mission completion with high reliability even with severely degraded or failing components.

Lubricant degradation generally depends on the complex interaction between many factors such as operating condition, type of machinery, loading profile, amount of oil present, base oil formula, type of additives, type and amount of contaminants, environment (e.g., temperature, humidity) etc. Many offline techniques such as spectroscopic and ferrographic analysis are very effective for analyzing root causes of lubricant failure. However, such techniques can only be performed at specific time intervals through offline sampling because the cost to provide preventive maintenance is often limited. Moreover, the offline tests can miss some types of lubricant degradation and failures occurring between sampling intervals. An online health lubricant monitoring system can improve preventive maintenance through timely identification of incipient lubricant degradation and thereby reduce machine down time and maintenance costs.

Multiple data fusion systems are available to combine the information from the sensor with other operating, schedule, machinery, and environmental information. A model-based sensor fusion method has been developed to combine information of lubricant properties measured by the fluid sensor array. The integration of the measured lubricant properties can be used to more accurately establish the condition of the lubricant (e.g., diagnostics) and also to predict the remaining useful life of the lubricant (e.g., prognostics). In accordance therewith, an on-line lubricant health monitoring system can be used with a variety of different fluid formulations by using one or more data fusion and pattern recognition techniques.

Data Fusion

Data fusion techniques combine the output of multiple sensors to obtain more accurate information than is possible from a single sensor. These techniques have been applied to both military and nonmilitary problems. Military applications include automated target recognition (e.g., for use in smart weapons), guidance for autonomous vehicles, remote sensing and problems involving the location, characterization and identification of dynamic (moving) entities such as emitters, platforms, weapons and military vehicles. Nonmilitary applications include industrial and manufacturing process monitors, condition based maintenance (CBM) for complex machinery, robotics and medical applications. Several techniques may be are used in multi-sensor data fusion. Because in many of the applications the information to be fused comes from different sources, the data fusion process may include many disciplines such as signal processing, statistical estimation, decision and control theory, and artificial intelligence.

There are several benefits of using multiple sensors integrated into a data sensor suite and data fusion architecture. Most notably, more robust operational performance can be realized and extended spatial/temporal coverage is possible. These benefits result because a single sensor can contribute only limited information, multiple sensors with redundant and complementary information will have higher operational reliability, and multiple sensors can provide greater coverage of an event that needs to be detected. Even multiple sensors of the same type can provide enhanced accuracy and reliability of the sensor signal and improved signal-to-noise (SNR) ratio.

Data Fusion Process Model

Figure 31:
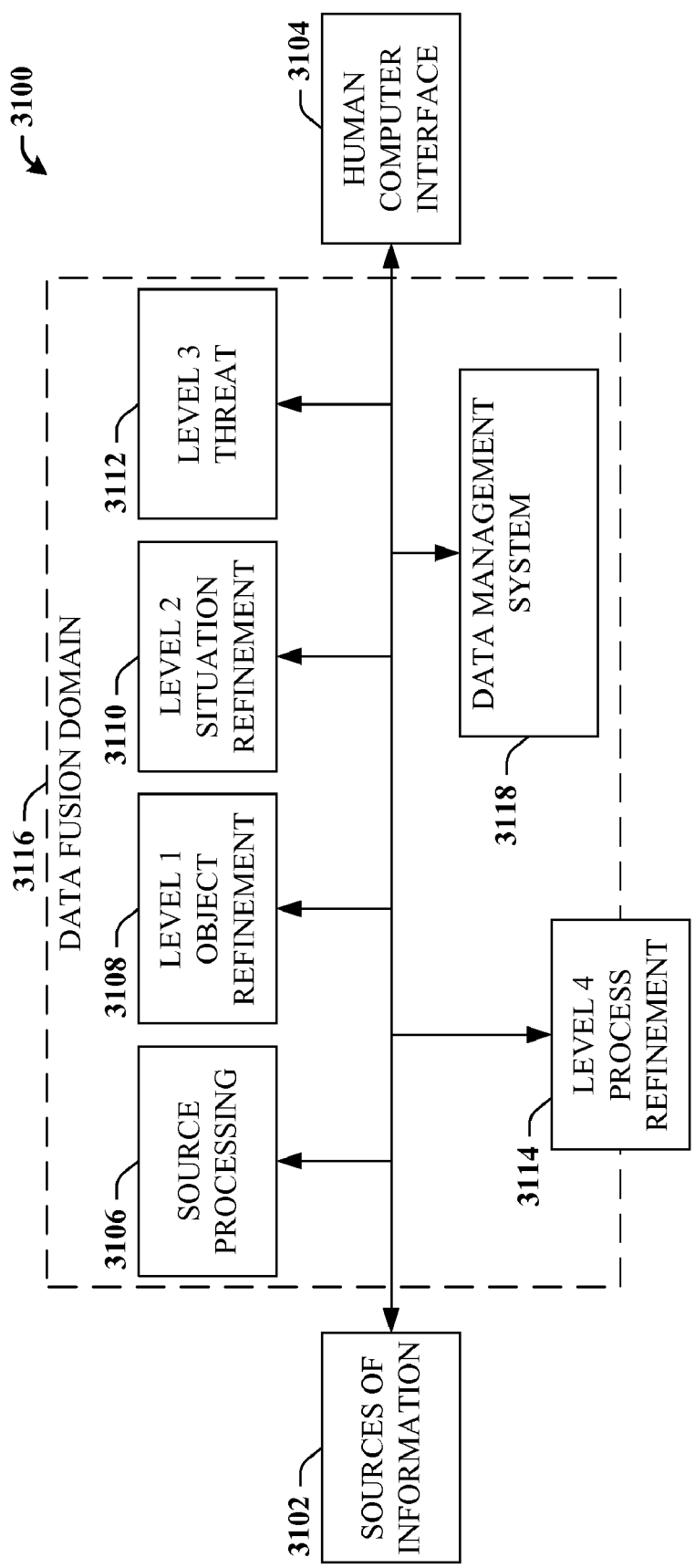
FIG. 31 is a block diagram of a data fusion model.

Referring now to FIG. 31, a data fusion model 3100 is depicted. Data fusion levels are convenient ways to organize and categorize data fusion functions. How a specific process is implemented depends on the individual systems requirements, and there is considerable flexibility in the possible approaches including hybrid or adaptive user-defined data fusion approaches. Flexibility also exists in determining where in the process to fuse the information. The Joint Directors of Laboratories (JDL) Data Fusion Working Group, established in 1986, began to codify the terminology related to data fusion. The result of that effort is a process model for data fusion. A top level representation of the JDL data fusion process model 3100 is shown.

The JDL process model of data fusion is functionally oriented and is intended to be very general and useful across different application areas. The JDL data fusion model 3100 is a conceptual model that identifies the process, functions, categories and specific techniques that are applicable to data fusion. For example, sources of information 3102 can indicate the number and/or type of input sources of information. Human Computer Interface (HCI) 3104 can allow human input such as commands, and information requests. Through the HCI a data fusion system can communicate results such as alerts, etc. Source Preprocessing 3106 (e.g., Process Assignment) can reduce the load on the data fusion system by allocating data to appropriate processes. Level 1 Processing 3108 (e.g., Object Refinement) can combine, e.g., location, identity and parametric information to achieve a refined representation of individual objects. Level 2 Processing 3110 (e.g., Situation Refinement) can develop a description of the current relationships among objects and events in the context of their environment. Level 3 Processing 3112 (e.g., Threat Refinement) can project the current situation into the future to draw inferences about enemy threats, friends and opportunities for operations. Level 4 Processing (Process Refinement) Level 4 Processing 3114 can perform a variety of exemplary functions, detailed below.

First, Level 4 Processing 3114 can monitor the performance of the data fusion process to provide information about real-time control and long term performance. Second, Level 4 Processing 3114 can identify what information is needed to improve the multilevel fusion product, as well as determine the source specific requirement to collect relevant information, and allocating and directing the sources to achieve the mission goals. Some of these functions can be outside of the domain 3116 of data fusion function.

A Data Management System (DMS) 3118 can also be provided in the domain 3116. The DMS 3118 can be an extensive ancillary function that is required to support data fusion due to the variety and amount of data, as well as the need for data retrieval, storage, archiving, compression, relational queries and data protection.

Architecture for Multisensor Data Fusion

Figure 32A:
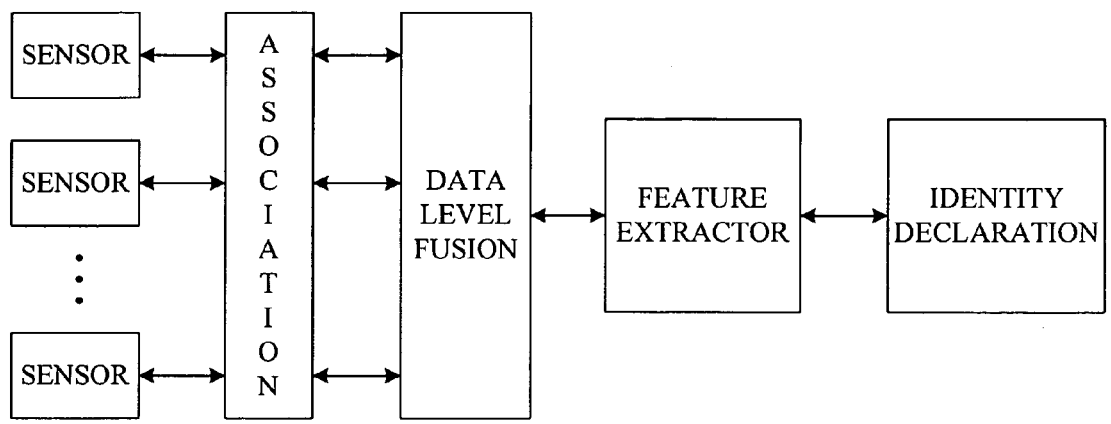
FIG. 32A is a block diagram of a data level fusion architecture for multisensor identity fusion.
Figure 32B:
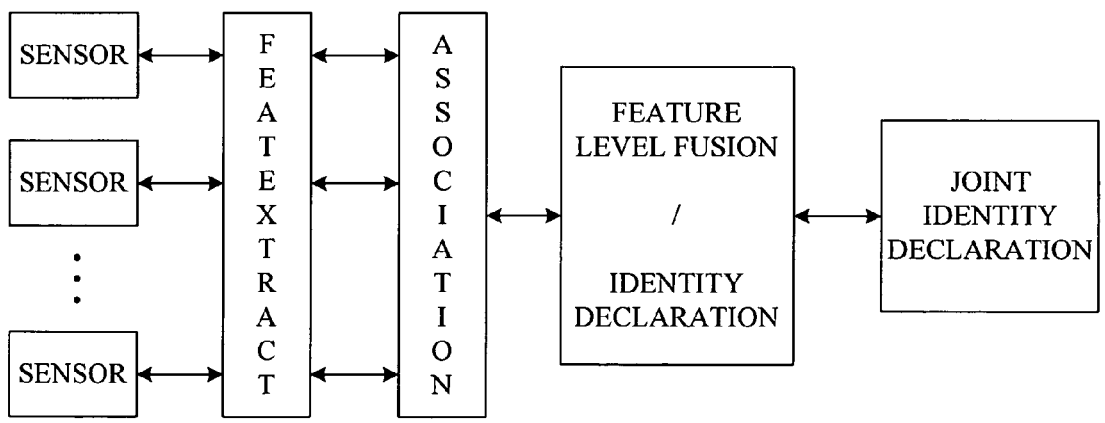
FIG. 32B is a block diagram of a feature level fusion architecture for multisensor identity fusion.
Figure 33:
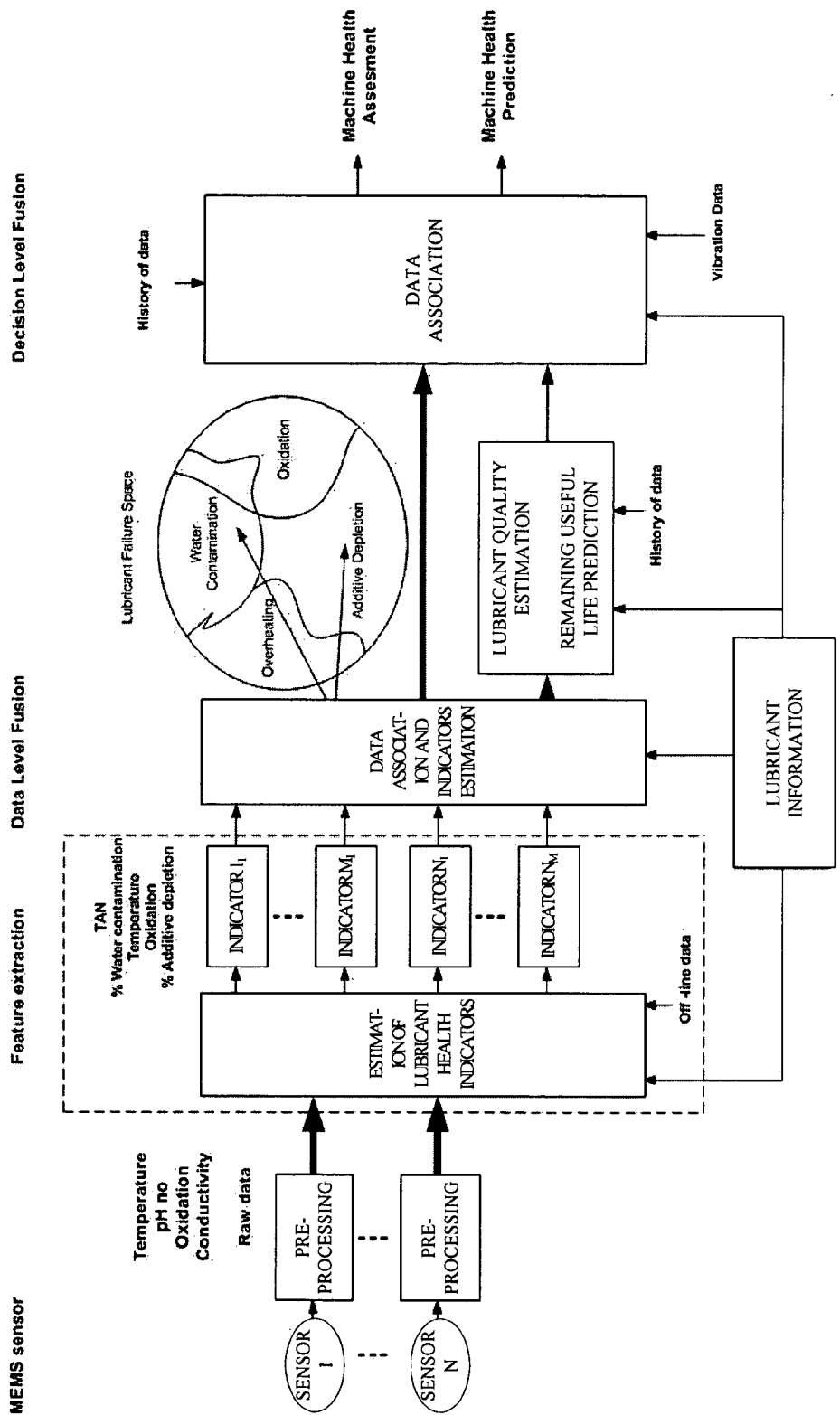
FIG. 33 is a block diagram of a conceptual framework for a data fusion system.

Turning now to FIGS. 32 and 33, a data level fusion architecture 3200 for multi-sensor identity fusion and a feature level fusion architecture 3300 for multi-sensor identity fusion, respectively, are depicted. One of the key issues in developing a multi-sensor data fusion system is determining where in the data flow to combine or fuse the data. There are two main objectives for the Level 1 processing 3108 data fusion: the fusion of location information in a distributed sensor array system and the fusion of parametric data. In a target tracking application, for example, the fusion of location information is used to determine the position and velocity of an object and the fusion of parametric data are used to classify or identify the object. In this aspect, there are three broad alternatives to fusing location information to determine position and velocity of moving object: 1) Fusion of raw observational data (e.g., data level fusion); 2) Fusion of state vectors (e.g., a state vector is an estimate using an individual sensor's measurements of the position and velocity of an observed object); and 3) Fusion of either raw data or state vector data.

An example of the second type of Level 1 processing 3108 considered is identity fusion. For identity fusion there are several types of architecture that can be used. For example, raw data level fusion, feature level fusion, decision level fusion, etc.

Direct fusion of raw sensor data is depicted in FIG. 32A in the architecture 3200. Each sensor can observe an object and the raw sensor data can be combined. This is commonly achieved by using a feature extraction vector from the fused data, and a transformation is made between the feature vector and the declaration of object identity. Fusion at the raw data level is not generally used when different types of sensors are used with different data formats and types and sampling rates.

The second architecture 3202 for identity fusion is feature level fusion, illustrated in FIG. 32B. In this case, each sensor observes an object, and feature extraction is performed to get the feature vector from each sensor. These feature vectors are then fused and an object identity declaration is made based on the joint feature vector. Techniques such as neural networks, cluster analysis, templates and knowledge-based techniques are used in this data fusion architecture.

In the architecture 3202, each sensor can perform an independent identity declaration process based only on its source data. For example, each sensor can convert observed object attributes into a preliminary declaration of object identity. Therefore, it does not limit the fusion process to a specific feature and it allows new features to be added to the system or different features to be used without changing the entire analysis. The object identity declaration provided by the individual sensors is combined using decision level techniques such as classical interface, Bayesian interface or knowledge-based techniques. A conceptual framework for a data fusion system is depicted in FIG. 33.

Decision Level Identity (Detection and Classification) Techniques

Decision level fusion seeks to process an identity declaration from multiple sensors to achieve a joint declaration of identity. In the lube health application of interest to us, identity declaration is consistent with determining the type and extent of degradation in the lubricating fluid. The most widely used techniques are:

Classical interface: Classical interface methods seek to determine the validity of a proposed hypothesis (versus an alternative hypothesis) based on empirical probabilities. Classical interface methods compute the joint probability of an observation, or observation sequence, given an assumed (null) hypothesis.

Bayesian interface: Bayesian interface methods update the probabilities of alternative hypotheses, based on observational evidence. Bayes' formula defines the relationship between the a priori probability of a hypothesis, the conditional probability of an observation given a hypothesis, and the posteriori probability of the hypothesis.

Dempster-Shafter: Analogous to the Bayesian interface method, the Dempster-Shafter technique updates the posteriori belief of proposition given observational evidence; to compute the assessment of belief that any given proposition is true.

Generalized Evidence Processing Theory: This approach is generalization of the Bayesian process and uses a combination of rules to assign evidence and optimize the resulting decision.

Fuzzy Logic Interface: This is a fusion technique that uses the membership function approach to scale and combine specific input quantities to yield the fused outputs. The basis for the combined output comes from scaling the developed membership functions based on a set of rules developed in a rule base that is defined by the user.

Neural Network Fusion: A well-accepted application of artificial neural networks is data and feature fusion. For the purposes of fusion, a network's ability to combine information in real time with the added capability of autonomous re-learning (if necessary) makes it a very attractive approach for many fusion applications.

These techniques, as well as others can be employed for the purpose of estimation. For example, the control component 108 of FIG. 1 can infer a future state 112 based upon the information provided by the sensor 106.

Estimation Techniques

Once multi-sensor information has been obtained and features have been extracted from the data and sorted into groups associated with different situations, estimation techniques can be applied to combine or fuse the data. The estimation techniques determine the "state" vectors that best fit the data in a well defined mathematical sense. Estimation problems may be dynamic, in which the state vector changes as a function time, or static, in which case the state vector is constant in time. At the same time, estimation techniques can be recursive (e.g., Kalman filtering) and non-recursive (e.g., standard implementations of linear regression). Certain questions need to be answered when applying estimation algorithms. For example, 1. System models: What models should be selected to define the problem under consideration? What is to be estimated and how do we predict the state vector in time? What assumptions can we make about the observation process?
2. Optimization criteria: What criteria will give the best fit to the data?
3. Optimization approach: Having defined criteria for the best fit, what method will be used to estimate the unknown parameters/states given the criterion that has been chosen?
4. Processing approach: Fundamentally, how will the observations (data) be processed? For example, will they be processed in a batch mode in which all observations are used after they have been received, or sequentially, in which case the observations are processed one at a time as they are received.

TABLE 7

| System Models | Estimation Issues and Alternatives | | |
|---|---|---|---|
| | Optimization Criteria | Optimization Approach | Processing Approach |
| Observation equations | Least square (LS) | Direct Methods -non derivative methods: | Sequential processing |
| Equations of motions | Weighted LS Mean Square | Downhill Simplex Direction | Batch Processing technique |
| Dynamic model | Maximum likelihood | -Derivative Methods | Covariance |
| State Vector definition | Constrained | Conjugate | error |

TABLE 7-continued

| System Models | Estimation Issues and Alternatives | | |
|---|---|---|---|
| | Optimization Criteria | Optimization Approach | Processing Approach |
| Implementation Data editing Coordinate system | (Bayesian) | gradient Variable metric (Quasi- Newton) Indirect Methods Newton Raphson methods | formulation |

These techniques, as well as others are well-known by researchers and practitioners in the field and can be readily employed for the purpose of estimation. For example, the control component 108 of FIG. 1 can infer a future state 112 based upon the information provided by the sensor 106.

Kalman Filter

The Kalman filter uses the statistical characteristics of a measurement model to determine estimates recursively from the fused data. If the system can be described with a linear model and both system and sensor error can be modeled as white Gaussian noise, a Kalman filter provides unique, statistically optimal estimates for the data of interest. Consider a linear dynamic system including N sensor outputs represented by the following model:

$$x(k)=A(k)x(k-1)+B(k)u(k)+v(k)$$

$$y(k)=H(k)x(k)+w(k)$$

where k represents the discrete time index, x(k) is the state vector, u(k) the input vector, y(k) measurement vector, H(k) is the observation model of the N sensors, v(k) and w(k) zero mean white Gaussian noise sequences with covariance matrices Q(k) and R(k), respectively.

The Kalman filter provides an unbiased and optimal estimate of the state vector in the sense of minimizing the error covariance and can be described as follows:

Prediction:

$$\hat{x}(k)=A(k)x(k-1|k-1)+B(k)u(k)$$

$$P(k|k-1)=A(k)P(k-1|k-1)A^T(k)+Q(k)$$

Estimate:

$$K(k)=P(k|k-1)H^T(k).[H(k)P(k|k-1)H^T(k)+R(k)]^{-1}$$

$$\hat{x}(k|k)=\hat{x}(k|k-1)+K(k)[y(k)-H(k)\hat{x}(k|k-1)]$$

$$P(k)=[I-K(k)H(k)]P(k|k-1)$$

where $\hat{x}(k|k)$ represent the estimate of the state vector x(k|k), P(k|k) is the state estimate of covariance matrix, and K(k) is the Kalman filter gain matrix.

Condition Base Maintenance (CBM)

CBM is a philosophy for performing maintenance on a machine or system only when there is objective evidence of need or impending failure. Implementation of CBM involves predictive diagnostics (e.g., diagnostics of the current state or health of the machine and a prediction of the time to failure based on an assumed model of anticipated use). CBM and predictive diagnostics depend on multi-sensor data, such as vibration, acoustic noise, temperature, pressure, and lubrication health indices. This information must be effectively fused to determine machinery health. Moreover, the development of good maintenance can be obtained by reducing the risk of unexpected failure, minimizing maintenance and repair cost, maximizing system availability and increasing platform reliability.

CBM can use sensor systems to detect the earliest symptoms of incipient failure, diagnose emerging equipment problems and to predict how long the equipment can effectively serve its operational purpose. The sensors collect and evaluate real time data using signal processing algorithms. These algorithms correlate unique features in the sensor signals with important operating states and failure causes. The key to effectively implementing CBM is the ability to detect, classify, and predict the evolution of a failure mechanism with sufficient robustness, so that this information can be used as a basis for planned maintenance. Furthermore, CBM system data can be extremely valuable for decision support to avoid risk-prone operating strategies, maximize operational efficiency or maximize throughput, or minimize the impact of a potential failure. A CBM system should be capable of detecting the early initiation of a failure, evaluating the reliability of sensed condition and establishing potential causes, classifying the failure type and severity, identifying consequential or collateral failure(s) (e.g., an electrical unbalance in a three-phase motor winding may cause predicting remaining useful life (RUL) with a degree of certainty, and the like.

Review of Machine & Lubricant Health Monitoring & Prognosis Systems

From the literature survey of machine and lubricant health monitoring and prognosis systems, there are three major approaches for developing such on-line systems. The first one is a model-based approach. This approach has been implemented by developing oil degradation models using data from standard oil and machine tests. The model and online data from commercial sensors are used to estimate remaining useful life of the machine and lubricants. Smolenski and Schwartz used this approach to develop engine-oil degradation models by using off-line data and linear regression models. Toms developed an oil analysis expert system based on statistical analysis of samples of oil test data. This expert system, however, was designed only to monitor machine and lubricant health at the specific machine where the oil samples are collected. Price and Centers constructed and implemented an algorithm to predict ester-based lubricant behavior in a turbine engine. Input data consisted of selected lubricant flow rates, bulk lubricant and bearing temperatures, and laboratory generated data. The program used lubricant property data as a function of time at several temperatures to produce mathematical functions describing total acid number, viscosity change and evaporation as a function of temperature at selected times. Program output data are predicted values of critical lubricant properties as a function of engine hours, reflecting lubricant that has been added to the system because of evaporative and seal losses and the system also predicted degradation that could occur during cool-down cycles. Byington and Garga developed a data fusion system for predictive diagnostics for electromechanical systems. They developed a model of a turbine engine lubrication system by using analog electrical impedances to model the oil flow circuit. The model also contained analytical expressions for mass, momentum and energy equations, as well as other empirical relationships. This computer model was used to generate lubricant failure data for the construction of a failure tree for the lubricant.

The second approach is sensor-based approach. A fundamental concept of this approach is the development of sensors that can directly measure the lubricant condition. The trend of measured lubricant condition is used to predict the remaining useful life of the lubricant. Basu, et al. developed an oil condition sensor that measures the electrical properties of engine oil. They used the conductivity trend to determine the oil degradation process. The performance of this sensor is not dependent on any particular oil brand, classification, or viscosity grade. The smart sensor algorithm uses a pattern recognition technique to recognize the different stages of the oil conductivity trend. Phillips, et al. developed special designs of lubricant electrical property sensors to detect real-time oil degradation, water contamination and fuel dilution in operational engine oils for internal combustion engines. An equivalent circuit model of the sensor is used to extract the lubricant electrical properties.

The third approach is a hybrid approach, which is a combination of the sensor based approach and the model based approach. Jagannathan and Raju used MEMs technology to develop oil condition sensors for predicting the remaining useful life of engine oil. They developed a mapping between their sensor outputs to oil degradation parameters by training a neural-fuzzy model with off-line lubricant data.

Data Fusion System Framework for Lubricant and Machine Health Assessment

Figure 34:
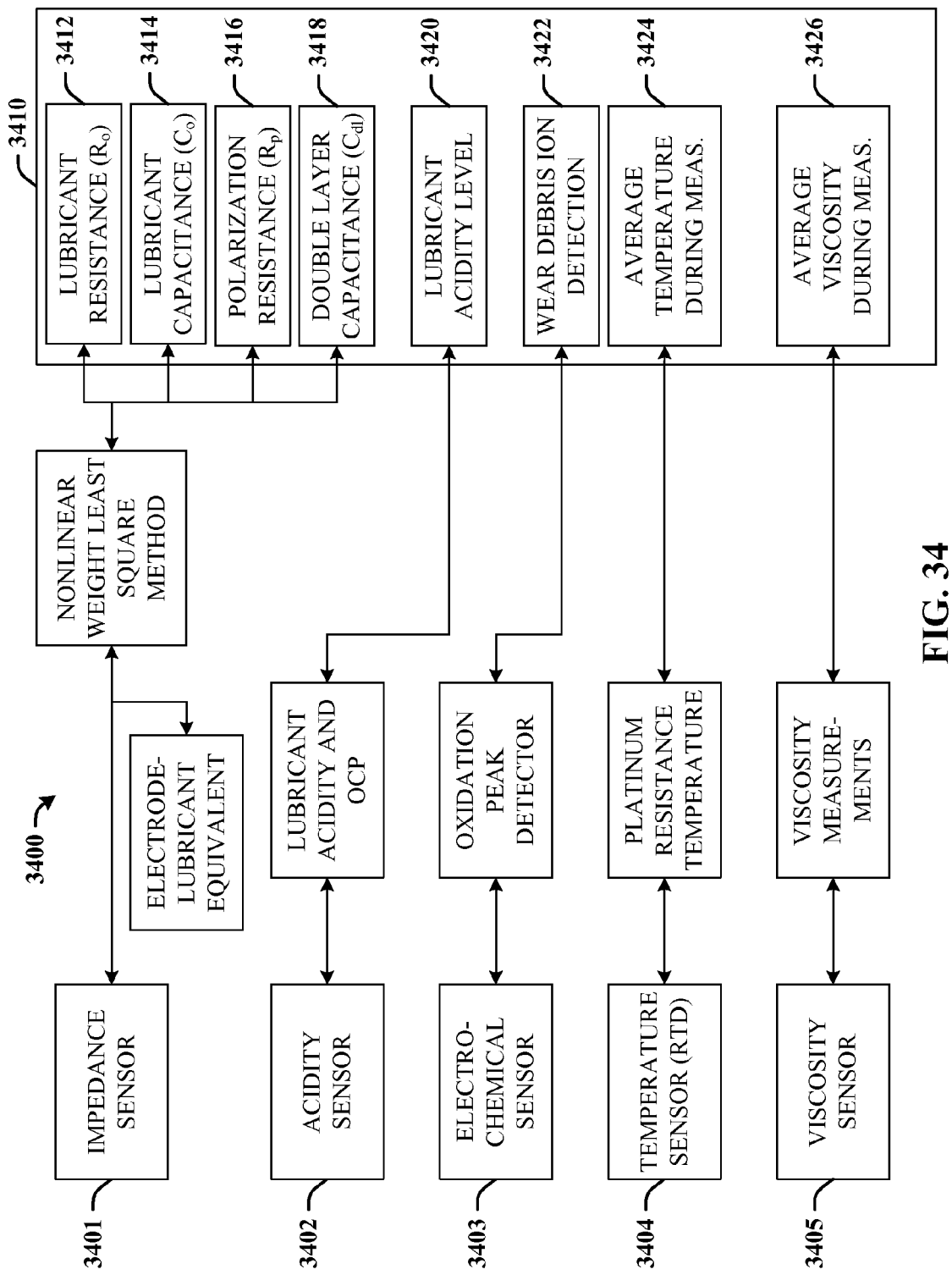
FIG. 34 is a block diagram of a feature extraction process of lubricant health data fusion.

Referring now to FIG. 34 a conceptual framework of the lubricant and machine health monitoring and prognosis system 3400 is depicted. The lubricant sensor array consists of five sensor elements 3401-3405. It is to be appreciated that other sensors not depicted could be included that measure other properties and/or parameters of the fluid (e.g., lubricant) as well as a plurality of sensors for each sensor type 3401-3405. The sensors shown are an impedance (conductivity) sensor 3401 that can measure, e.g., AC impedance, an acidity (TAN) sensor 3402 that can measure, e.g., lubricant acidity such as pH and/or open circuit potential (OCP), an electrochemical sensor 3403 that can measure, e.g., oxidation peak and/or water content or additive content, a resistance temperature detector (RTD) 3404 that can measure, e.g., platinum resistance temperature, and a MEMs sensor 3405 that can measure, e.g., viscosity, density, pressure and/or flow of the fluid or fluid electrical properties (e.g. dielectric strength). Sensor operation and preprocessing of the data can use techniques such as Electrochemical Impedance Spectroscopy (EIS), Cyclic Voltammetry (CV), open circuit potential (OCP) and an RTD model to transform the sensor array data into information about the lubricant properties. The feature extraction process can estimate the lubricant heath indicators from lubricant property measurements and create a feature vector or a lubricant health indicator vector. The feature fusion process associates the lubricant information, the feature vectors at the current time step and at the previous time steps, to determine the condition of the lubricant. The current condition of the lubricant is then used to estimate the lubricant heath as well as the remaining useful life of the lubricant. Finally, at the decision fusion level, a joint declaration of the estimate of lubricant health, the remaining useful life of the lubricant, the machine vibration analysis and the history of machine health provides an overall assessment of the health of the machine as well as a set of prognostic indicators.

Feature Extraction Process

Features are an abstraction of the raw data that provide a reduced data set with sufficient accuracy that concisely represents the original sensor information. In general, these features may not allow reconstruction of the original data. Transformation of the raw data into a relevant feature vector is termed feature extraction. In the lubricant health data fusion system, the raw data measurements from the sensor array 3401-3405 can be transformed into a vector of lubricant health indicators 3410. These lubricant health indicators are electrical properties 3412-3418, acidity level 3420, (the detection of) oxidized ions 3422, e.g., due to machine wear, the average temperature 3424 of the measured lubricant and average viscosity 3426 of the lubricant.

The experiments of the acidity sensors 3402 with the lubricant samples showed a correlation between the open circuit potential (OCP) of the sensor 3402 and the total acid number of the samples. Further, the experiments with the acidity sensors 3402 using the lubricant samples from laboratory gearbox experiments (Table 6) show the ability to discriminate between a new lubricant sample and a degraded lubricant samples. The current OCP-lubricant acidity model is simply a linear relationship between the OCP level at the specified time and the lubricant acidity level (e.g., total acid number called TAN or acid number called AN).

Extracting information from the lubricant impedance measurement involves an estimation of electrical properties (e.g., 3412-3418) of the lubricant by using the electrode-lubricant circuit equivalent model given in FIG. 3. The total impedance of the electrode-lubricant system is given by equation.

$$Z_{total} = \frac{R_P - jR_p^2 \omega C_{dl}}{R_p^2 \omega^2 C_{dl}^2 + 1} + \frac{R_o - jR_o^2 \omega C_o}{R_o^2 \omega^2 C_o^2 + 1}$$

$$Z_{total} = Z'_{total} + jZ''_{total}$$

$$Z'_{total} = \frac{R_P}{R_p^2 \omega^2 C_{dl}^2 + 1} + \frac{R_o}{R_o^2 \omega^2 C_o^2 + 1}$$

$$Z''_{total} = \frac{-R_p^2 \omega C_{dl}}{R_p^2 \omega^2 C_{dl}^2 + 1} - \frac{R_o^2 \omega C_o}{R_o^2 \omega^2 C_o^2 + 1},$$

where, $R_p$=Polarization resistance, $R_o$=Bulk lubricant layer resistance, $C_{dl}$=Double layer capacitance, $C_o$=Bulk lubricant layer capacitance, and $\omega$=Frequency in radians/§.

A weighted least-squares method with the Levenberg-Marquardt algorithm is used to find the best fit between the frequency response of the model and the measured EIS data. The best fit between the measured EIS data and the model can be achieved by solving the optimization problem:

Finding the best fit x that minimize a loss function L(x):

$$L(x) = e(x) W e(x)^T$$

$$x = [R_o C_o R_p C_{dl}]^T$$

The loss function L(x) is a scalar function of x that is the sum of the squares of the observation residuals weighted by W, and e is the vector of the residuals in the following form:

$$e(x) = \begin{bmatrix} y'(\omega_{max}) - z'_{total}(\omega_{max}, x) \\ y''(\omega_{max}) - z''_{total}(\omega_{max}, x) \\ y'(\omega_i) - z'_{total}(\omega_i, x) \\ y''(\omega_i) - z''_{total}(\omega_i, x) \\ \vdots \\ y'(\omega_{min}) - z'_{total}(\omega_{min}, x) \\ y''(\omega_{min}) - z''_{total}(\omega_{min}, x) \end{bmatrix}$$

W is a Weight matrix in this following format:

$$W = \begin{bmatrix} w_1, & 0, & \ldots, & 0 \\ 0, & w_2, & \ldots, & 0 \\ & & \ddots & \\ 0, & 0, & \ldots, & w_n \end{bmatrix},$$

where n=the number of sample frequencies used multiplied by two, $y'(\omega)$=the real part of the measured EIS data, $y''(\omega)$=the imaginary part of the measured EIS data, $\omega_{max}$=the highest sampling frequency, and $\omega_{max}$=the lowest sampling frequency.

Figure 35:
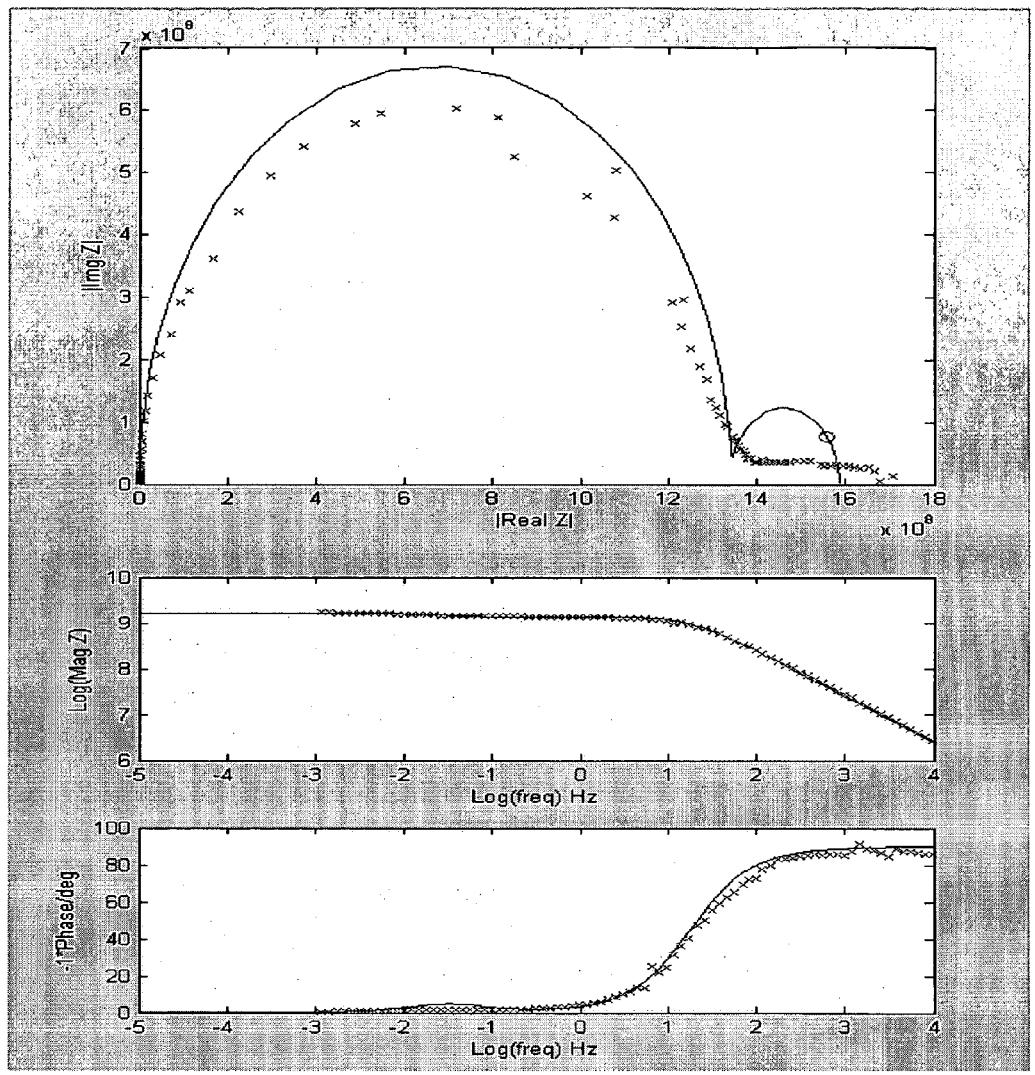
FIG. 35 is a Nyquist and Bode plot of model frequency response that fits with a sensor response in new lube oil.

The weights w should be selected so that the response of the model fit well with the EIS data in high and low frequency ranges. The plots in FIG. 35 show the frequency response from the equivalent model that fits with the EIS data, for new fresh oil.

Feature Level Fusion

At the feature level fusion, the vectors of lubricant health indicators are fused together and the declaration of the lubricant condition is made based on the joint feature vector. The approach to develop the declaration process is based on knowledge of the lubricant and the experimental data from the lubricant samples. An important factor that affects lubricant health is oxidation of the lubricant. Lubricants react with oxygen, especially at high temperature, to form hydroperoxides, free radicals, ketones, aldehydes and organic acids. The rate of this process is the oxidation rate. The rate of oxidation depends on the amount of oxygen available to react with the oil molecules, the temperature, and the amounts of water and metal catalysts. The onset of the oxidation process indicates that the antioxidant additive is almost completely depleted. Oxidation can not be prevented, but only delayed because of the presence of antioxidant additives.

Figure 36:
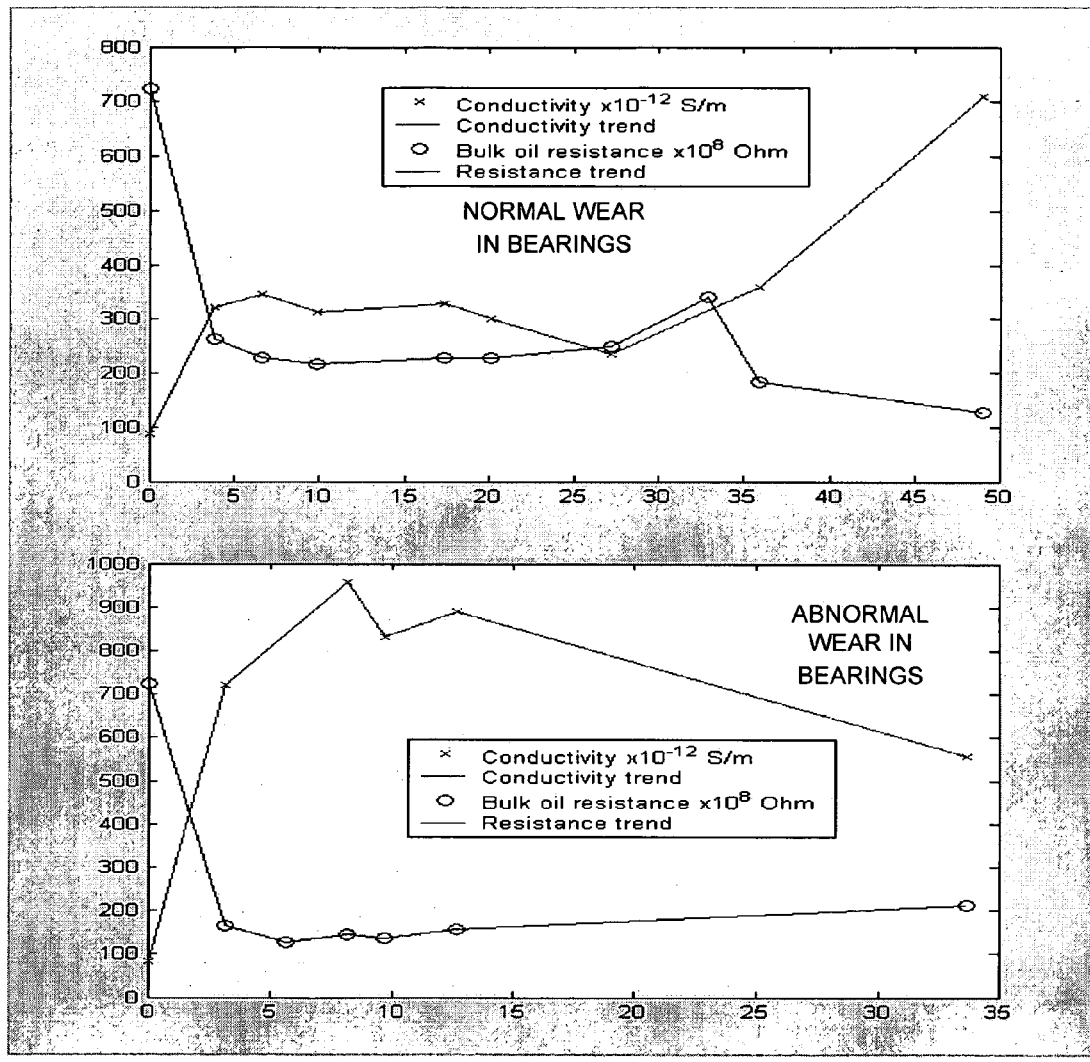
FIG. 36 is a plot of lubricant conductivity and bulk lubricant layer resistance ($R_o$).

By considering the experimental data from the laboratory gearbox experiments in Table 6, the estimated bulk lubricant layer ($R_o$) is inversely proportional to the measured conductivity of the test samples. The conductivity trend in FIG. 36, with the upper portion showing normal wear in the bearings and the lower portion showing abnormal wear in the bearings, illustrates that the conductivity of the oil has rapidly increased during the first five hours of operation. The first five hour period is defined as the break-in period for new clean oil. In the experiment without load, the change in the oil conductivity was minimal during the 5-35 hours of the test and then the conductivity rapidly increased after the 35th hour as shown. In the experiment with an external load on the gearbox, the conductivity trend shows the rapid increment in the conductivity of the lubricant during the 5-8 hour period and then the conductivity of the lubricant decreased after 8 hours. The estimated capacitance of the bulk lubricant layer ($C_o$), which is related to the dielectric constant of the lubricant, had relatively small changes after the break-in period in both of the experiments.

Figure 37:
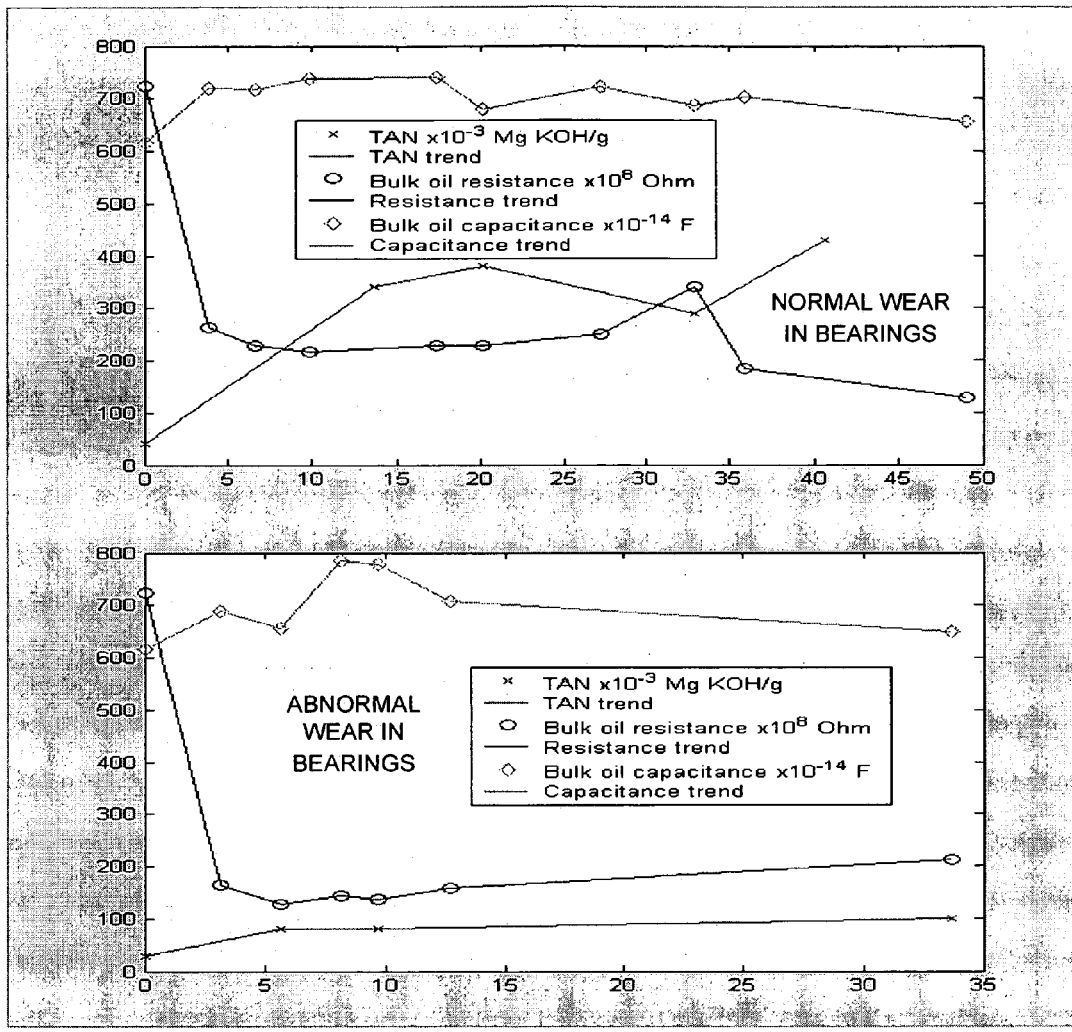
FIG. 37 is a plot of TAN, bulk lubricant layer resistance ($R_o$) and capacitance ($C_o$).

By considering the laboratory analysis of the oil samples, the total acid numbers (TAN) of the oil samples indicates that the acidity of the oil had increased after the break-in period for both of the experiments. However, the increment of oil acidity (TAN) was more rapid in the experiment without the load than the other experiment. The oil acidity (TAN) had slowly increased after the break-in period in both of the experiments. The trends of oil acidity (TAN) in the experiments are shown in FIG. 37, wherein the upper portion again depicts normal bearing wear and the lower portion indicates abnormal bearing wear. The plots distinguish the abnormal wear of the bearings. Since the gearbox bearing is made of iron, the number of iron particles in this experiment is higher than the others. This higher number of iron particles is expected to result in a higher conductivity of the lubricant. One interesting result is the conductivity of the oil sample: L0617-02. The number of iron particles in this sample is the highest number of iron particle (209 ppm) in all of the gearbox experiments.

The analysis of the experimental data permits developing a lubricant health assessment technique by using lubricant health indicators. Our approach is similar to the rate of change based alarm method to alert the user of abnormal changes in lubricant conditions. This method ignores the absolute values of the lubricant condition measurements. This approach has been effectively applied to wear particles and TAN. Table 8 below shows the lubricant health assessment technique using the rate of change based alarm approach. During the break-in period, the bulk lubricant layer resistance rapidly decreases when the new oil mixes with the used oil substances and particles left in the gearbox. The bulk lubricant layer capacitance and the acidity level however rapidly increase during this period. During the depletion of the additive, the acidity level of the lubricant slowly increases. The change in the bulk lubricant layer resistance should be minimal during this period since there is only a small change in the conductive component from the build-up of acid. This observation is based on the experimental data and the study of the lubricant conductivity trend given in. The change in the bulk lubricant layer capacitance during this period is also minimal since the change in the dielectric property of the lubricant depends on the change in the chemical and physical properties of the lubricant.

TABLE 8

Rate of Change Alarm in Normal Oil Degradation

| Lubricant Health indicator | Stage 1 Break-in period of Clean oil | Stage 2 Depletion of Additive (oil ok) | Stage 3 Onset of oxidation (oil degraded) | State 4 Increase in viscosity (oil failed) |
| --- | --- | --- | --- | --- |
| Resistance (Ro) | Gradually Decrease | Minimal change | Gradually Decrease | Gradually** Increase |
| Capacitance (Co) | Gradually Increase | Minimal change | Gradually Increase* | Continued Increase* |
| Acidity Level | Gradually Increase | Slowly Increase | Gradually Increase | Continued** Increase |

*Required further studies on lubricant degradation to confirm the assumption
**Assumption based on the basic property of lubricant The onset of significant lubricant oxidation starts when the depletion of the antioxidant is nearly complete. During this period, the acidity level rapidly increases as a result of increases in the acid compounds of the oxidation by-product. The bulk resistance then rapidly decreases after the onset of the oxidation. After the onset of the oxidation, it can be assumed that the bulk capacitance also rapidly increases because the chemical and physical properties of the lubricant start changing significantly.

Normally, the end of lubricant life is based on results from the standard lubricant laboratory tests and the lubricant specifications. S. S. Wang uses the inflection point of the conductivity trend, where the rate of lubricant resistivity is changing from a decreasing rate to an increasing rate. At this point, the viscosity of the lubricant is so high that the conductive ions in the lubricant can not move easily. In a military helicopter gearbox application, the inflection point of the bulk lubricant resistance may not be a good factor to define the end of the lubricant life because the physical properties of the lubricant have changed significantly at this point, and they may no longer be compliant with applicable military lubricant standards. Alternative methods to define the end of lubricant life are to use a limit of the acidity level or the limit of the rate at which the bulk resistance of the lubricant is decreasing. Alternatively, it is desirable to detect the presence of anti-oxidant additives and track the depletion of anti-oxidant additives. Sensor test results previously described demonstrated the ability to detect additive ions (e.g., phosphorous) in lubricating oil.

The rate of change based alarm approach may be sufficient to identify the lubricant health condition during normal lubricant degradation. However, this approach may not be sufficient to identify the root causes of a lubricant failure such as water contamination. A good example is the discrimination between the lubricant failure case of water contamination and the failure case of debris contamination. Considering the experimental data of the gearbox oil samples with an external load, the resistivity of the lubricant continued to rapidly increase after the break-in period and then increased after 10 hours of operation while the acidity level was relatively unchanged. Because water and metal debris reduce the resistivity of the lubricant, it is very difficult to differentiate between water contamination and debris contamination by using the rate of change approach, alone.

A lubricant fault classification process may be derived based on fluid chemistry and the experimental response of lubricant sensor array to specific lubricants with different failure modes to construct the lubricant failure mode space. For example, Phillips & Eggers reported that 1% water lowers the output of their oil condition sensor by two orders of magnitudes.

Figure 38:
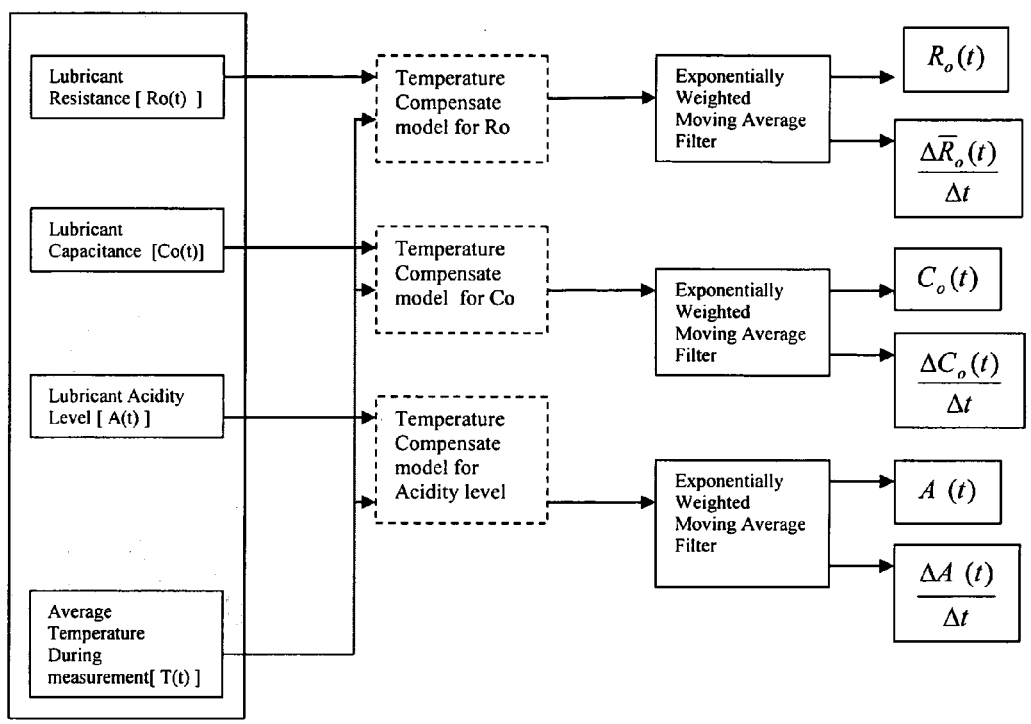
FIG. 38 is a block diagram of a system for the temperature compensation process and the signal conditioning.
Figure 53B:
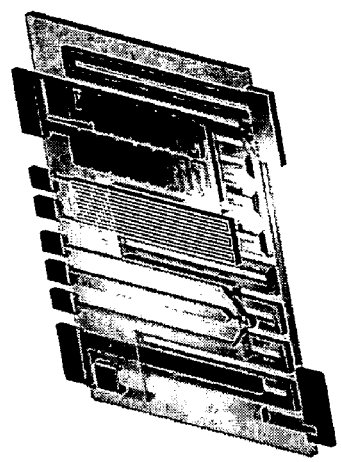
FIG. 53 is a block diagram of a multi-element fluid sensor to IntelliBus interface.
Figure 53A:
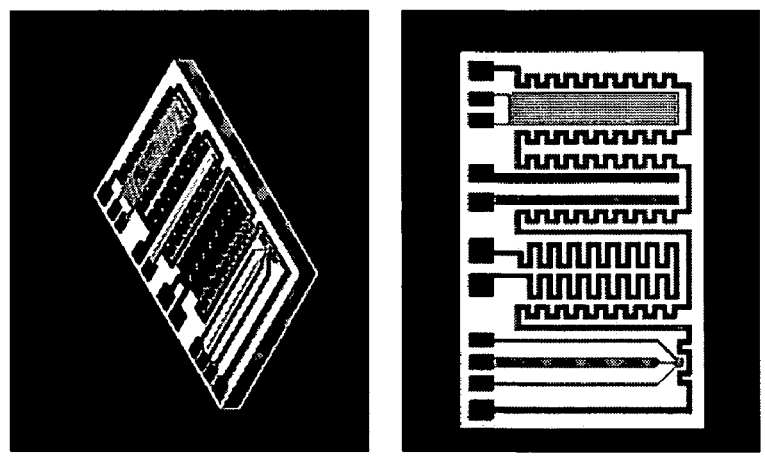

Referring now to FIG. 38, a system 3800 for temperature compensation and signal conditioning with feature level fusion is depicted. Because the lubricant health indicators are temperature dependent, the measurement of each sensor element should be compensated to the same reference temperature. Sensor-temperature compensation models may be developed analytically based on fluid physics or experimentally. Additionally, thermally controlled sensor elements may be employed. A thermally controlled sensor suite consists of one or more heater elements and one or more temperature sensor elements that permit heating the fluid such as through resistance heating and sensing the temperature of the resultant heated fluid. It is possible to use the same electrical structure for both heating and sensing. A preferred design is to employ a separate heating element and a separate temperature sensing element. The power provided to the heating element can be controlled to maintain the sensor elements and adjacent fluid being sensed at a specific temperature. The temperature of the sensor elements and adjacent fluid provided by the temperature sensor element can be used in a closed-loop fashion as is well-known in the art to maintain the sensor elements and adjacent fluid at a target, setpoint temperature. (FIGS. 53A and 53B)

Temperature compensated sensor measurements are then filtered using exponentially weighted moving average filters. This type of filter is commonly used in noise reduction algorithms in the process industries. The exponentially-weighted, moving average procedure can be done with the following procedure: 1) Selecting a number of data points for the average computation (n); 2) Compute the average of the sensor measurement with n−1 data points, $\bar{x}_{n-1}$ by using the following equitation $$\bar{x}_{n-1} = \frac{1}{n-1} \sum_{i=1}^{n-1} x_i \quad \bar{x}_i = x_i, \quad 1 \le i < n-1,$$

where $x_i$=the measurement of the sensor at time step i; and 3) Computing $\bar{x}_k$ when k>n−1 by the following equation:

$$\bar{x}_k = \alpha \bar{x}_{k-1} + (1-\alpha)x_k, \quad \alpha = \frac{n}{n+1},$$

where α=filter constant $0 \le \alpha < 1$

After the current measurements are filtered, the average measurement at time k, $\bar{x}_k$ and the rate of change $$\frac{\Delta \bar{x}_k}{\Delta t}$$

or $$\Delta \bar{x}_k = \frac{\bar{x}_k - \bar{x}_{k-1}}{t_k - t_{k-1}}$$

are computed.

Figure 39:
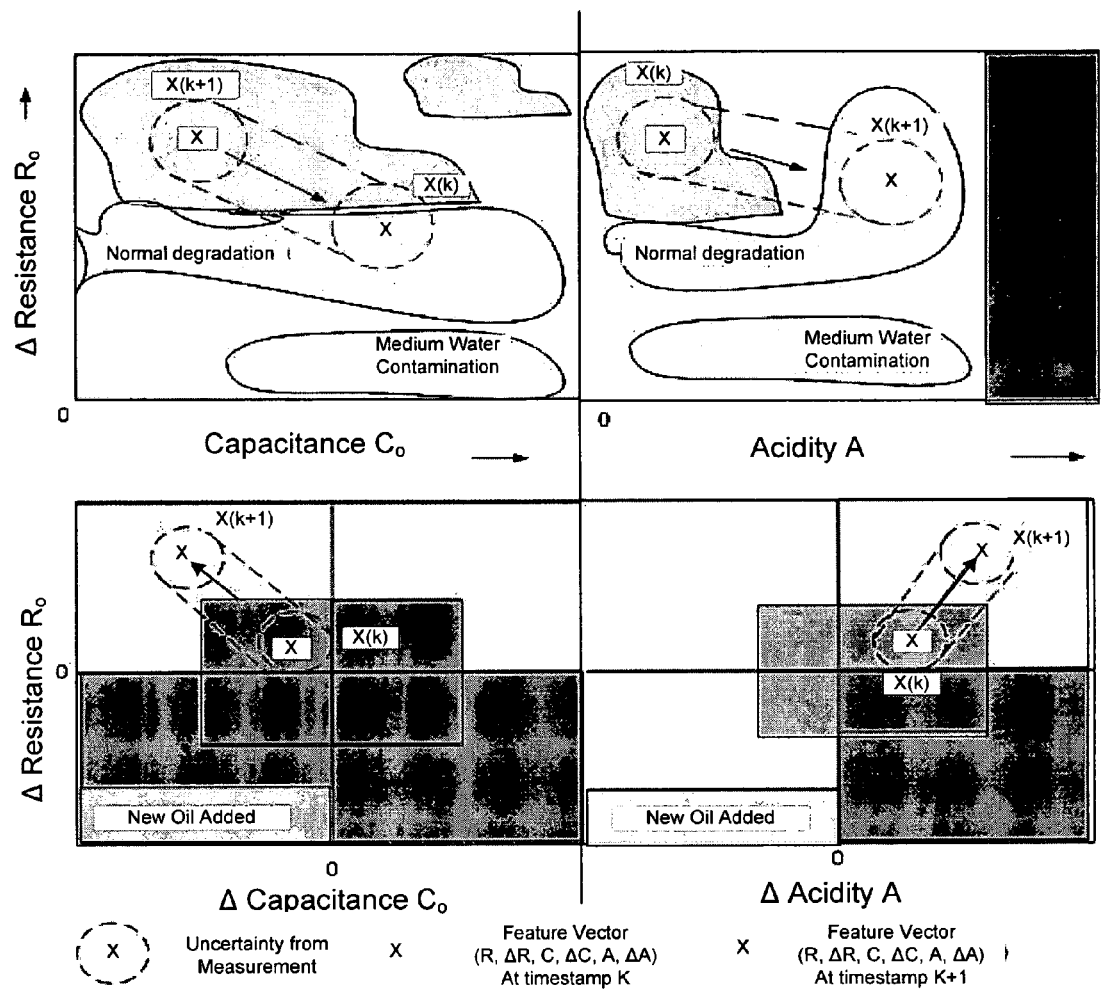
FIG. 39 is a diagram of two-dimensional projections of six-dimensional lubricant failure mode space.

The first approach to developing the lubricant failure mode space is to use the lubricant experiment data for manual clustering in a six dimensional space ($R_o \times \Delta R_o \times C_o \times \Delta C_o \times A_o \times \Delta A_o$). The high dimensional space is clustered into the green zone (oil ok), the red zone (oil failed) and the yellow zone (oil degraded) with several simple failure modes such as medium water contamination and normal oil degradation. The diagram in FIG. 39 shows some two dimensional projections of the six dimensional failure space. Assuming that the feature vector, X(k) stays in the oil ok zone (green) at time k, the feature vector then moves to the oil degradation zone (yellow) at the time k+1 because the changes in $R_o$, $C_o$ and A significantly increase.

The lubricant failure mode space clearly depends on factors such as the physical and chemical properties of the lubricants, the equipment using the lubricant, and the operating environment. Because there are a large variety of lubricant formulations used in industrial and military applications, the approach to manually partition the failure mode space requires a lubricant test data and data analysis. This approach while generally not useful for a universal on-line lubricant health monitoring system, will provide information on how the lubricant health indicators can be used to discriminate between the different health stages as well as provide cues indicating the various likely failure modes of lubricant.

Figure 40:
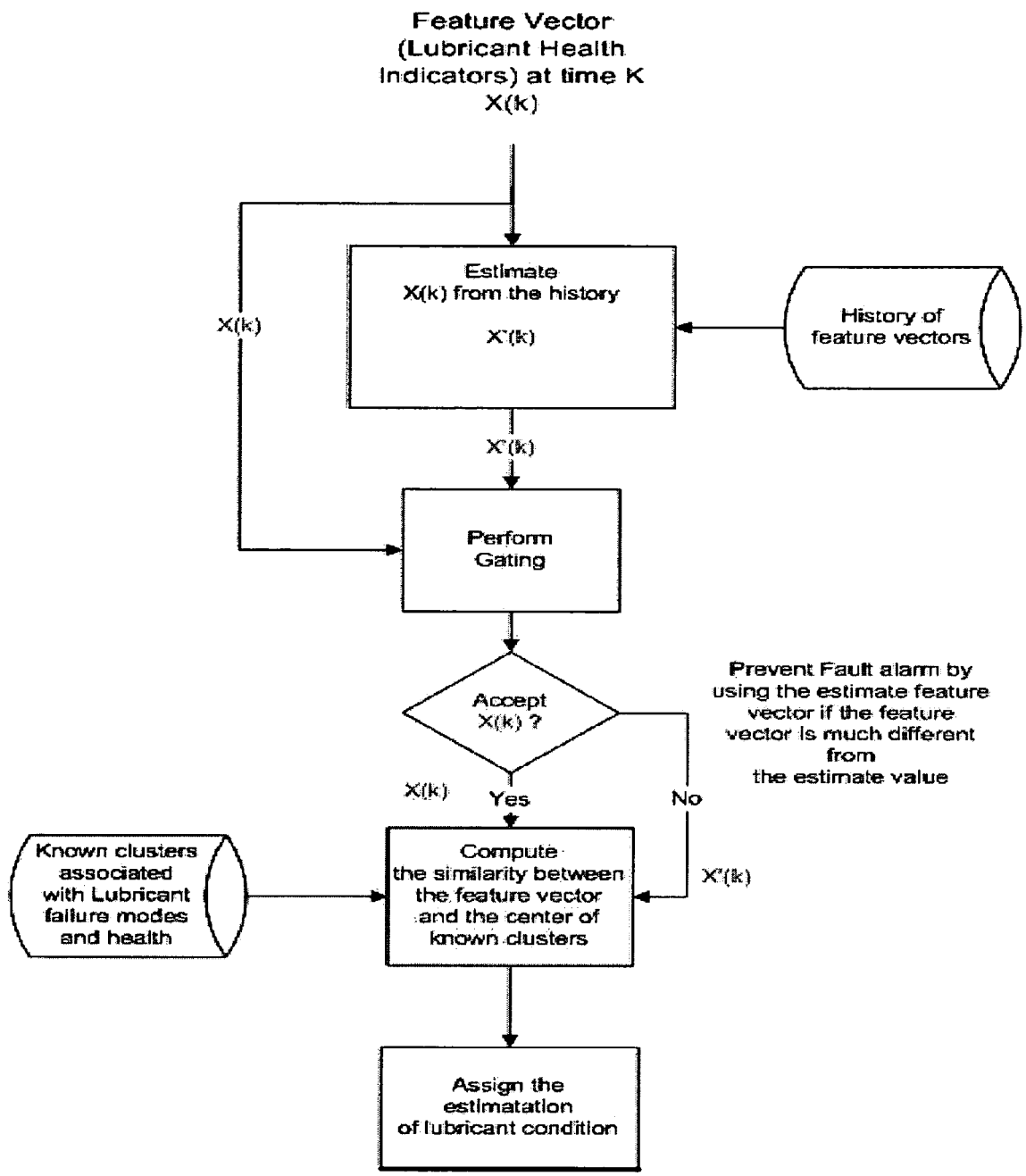
FIG. 40 is an exemplary flow chart of procedures facilitating an algorithm of data association.

The flowchart in FIG. 40 shows an algorithm for the data association in this feature level fusion. By assuming that the feature X(k) is available at time k, the rate of change and the feature vector at time k−1 are used to estimate the feature vector X(k). A gating algorithm then compares the estimated feature vector $\bar{X}(k)$ with the measured vector X(k). If the estimated vector $\bar{X}(k)$ is much different than the measured vector X(k), the measured X(k) is discarded and the estimated vector $\bar{X}(k)$ is used instead for the data association. Otherwise, we use X(k) for the data association. This procedure reduces the possibility of false alarms from noisy measurements. In the next state, the similarity between the feature vector or the estimated feature vector and the feature vectors representing the known lubricant failures are computed by evaluating the distance between the two vectors. A simple Euclidean distance measure may be computed although other distance measures may be used instead. It is necessary to scale the entire feature vector to [0, 1] since the measurements of the lubricant health indicators can have widely varying ranges of sensor data magnitudes. An alternative method is to use the correlation coefficient to measure the association. Finally, the association between the current feature vector and the known failure mode is assigned by using the measure of correlation.

The correlation between the vector A and B measured by a Euclidean distance measurement is given by:

$$A=[a_1 a_2 a_3]^T, B=[b_1 b_2 b_3]^T a_i \text{ and } b_i=[0,1]$$

$$D_{AB} = \sqrt{g_1(a_1-b_1)^2 + g_2(a_2-b_2)^2 + g_3(a_3-b_3)^2},$$

where $g_1$, $g_2$ and $g_3$ are the weights that assign the contribution of each vector component to the correlation measurement, where $g_1+g_2+g_3=1$. We can use these weights, g, to decrease or increase the contribution of some health indicators such as the acidity level in the correlation measurement. A flow chart of the data association algorithm is shown in FIG. 40.

Lubricant Health Estimation

Figure 41:
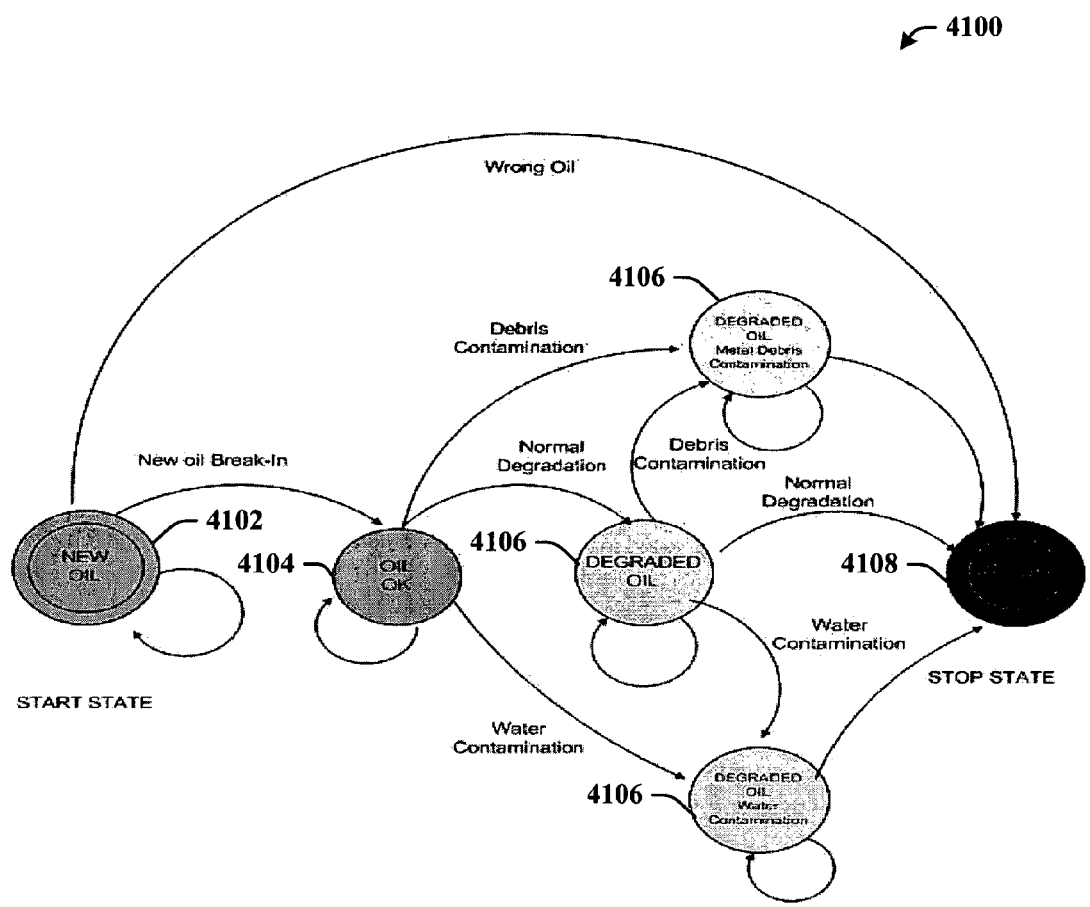
FIG. 41 is an exemplary finite state automaton for lubricant heath estimation.
Figure 42:
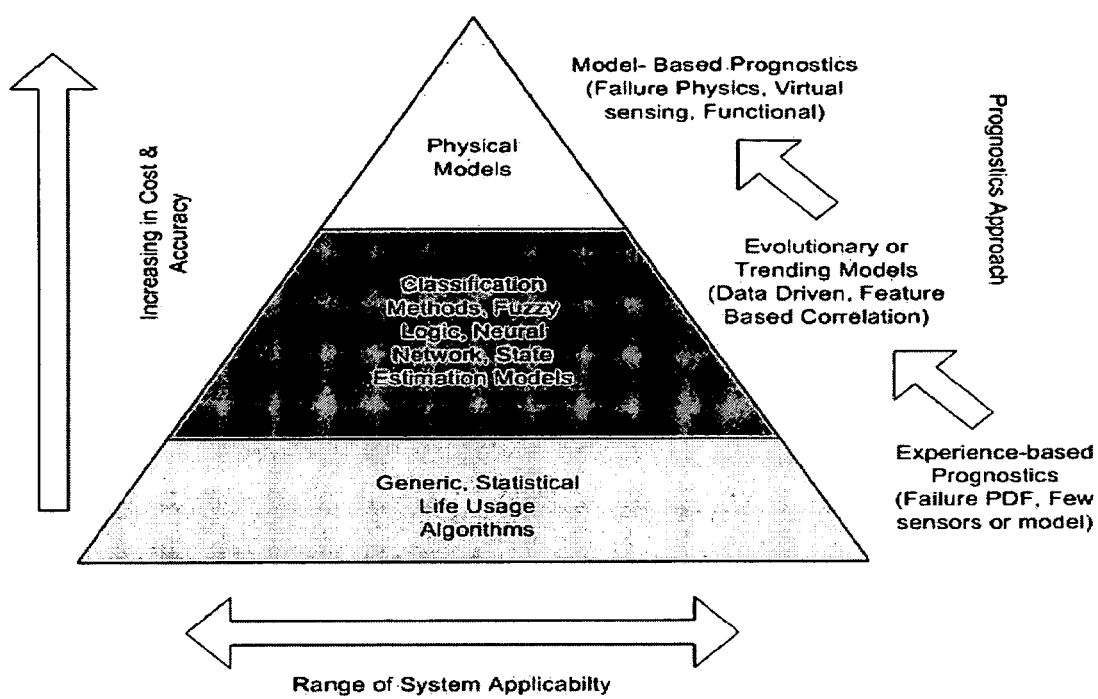
FIG. 42 is a block diagram that illustrates a hierarchy of prognostic approaches.

FIG. 41 depicts a finite state transition map 4100 for lubricant heath estimation. The data association process at the feature level fusion can provide the measurement of the correlation between the lubricant sensor measurement and the known lubricant failures. The finite state automaton 4100 represents a simple lubricant health estimation process. The state of the finite automata represents the health status of lubricant. The lubricant health estimation has new oil 4102, oil that is okay 4104, degraded oil 4106, and failed oil 4108. The new oil 4102 status represents the lubricant condition of fresh clean oil before the break-in period. The okay oil 4104 status represents the lubricant condition after the break-in period where the antioxidant is still active. The oil degraded 4106 status represents the lubricant condition after the onset of lubricant oxidation. The failed oil 4108 status represents the lubricant condition that exceeds the lubricant or machine operating specifications. When the lubricant has reached the failed oil 4108 status, the remaining useful life of the lubricant equals to zero. In Table 8, the failed oil 4108 status represents the lubricant that has a breakdown in viscosity. Abnormal oil degradation such as water contamination or debris contamination can also be represented by a degradation of the state of lubricant. A change in lubricant status is represented by a transition from one state to other states. The transition is triggered by the highest correlation between the current feature vector and vectors in the known failure mode space. The degradation progress of the oil is typically not reversible without intervention, for example replenishing a depleted additive or replacing the oil.

Lubricant Health Prognosis

Prognosis is the process of predicting the future state of a system. Lubricant health prognosis gives the prediction of the remaining useful life of the lubricant. Several techniques such as Stochastic Auto Regressive Integrated Moving Average (ARIMA) models, fuzzy pattern recognition principles, nonlinear stochastic models of fatigue crack dynamics, polynomial neural networks and wavelet neural networks have been introduced over the past years to address a variety of diagnostic and prognostic problems.

An effective approach is the least squares regression method to determine a trend of the sensor outputs by fitting a linear model to the history of each of the sensor outputs. The next step is to determine the limit of each of the sensor outputs at the end of the useful life of the lubricant. The time at which the trend of one or more of the sensor outputs intersects with their corresponding useful life limit can be ascertained. This information can be used to determine an approximation of the remaining useful life of the lubricant. Turning briefly, to 42, a hierarchy of prognostic approaches developed by Byington, et al., illustrates various approaches for prognostics that range in scope from simple failure rate models to high-fidelity physical-based models is depicted.

Experienced-Based Approach

In the case where a physical model of a subsystem or component is not available and there is insufficient sensor information to assess the operating condition, an experienced-based prognostic model may be the only alternative. This prognostic approach requires the failure history or, data of components provided by manufacturers under similar operation. There are a number of methods that can be used to find a statistical distribution such as a Weibull distribution that fits the available data. The prognosis of when a component will fail or degrade is then based on the analysis of past experiences. This type of approach may use data on time scales on the order of a maintenance interval, and then the distributions are updated as more data becomes available.

Evolutionary Prognostics Approach

An evolutionary prognostic approach relies on tracking the condition and rate of change of the current component condition (e.g., lubricant health indicators 3410 from FIG. 34) and correlating the observations to known performance degradation or component fault models or trends. The trend of component degradation progressing through time is used for predicting the future state of the system. This approach works well for determining system level degradation from the improper functioning of multiple components. However, it requires sufficient sensory information and knowledge of proper system performance and/or knowledge of behavior during the failure scenarios that are of interest.

Feature Progression and AI-Based Prognostics

A feature progression and AI-Based prognostic approach uses known failure degradation paths of measured/extracted features as they progress over time for forecasting the future state of the system. In this approach neural networks or other AI techniques are trained on features that progress through failure condition. In this approach, the probability of failure curve progressing over time and the correlated feature magnitudes are required as a priori information to train a neural network. During training, the network adjusts its weights and thresholds based on the input features and desired output prediction. Once trained, the neural network architecture can be used to forecast feature progressions under similar operating conditions.

State Estimator Prognostics

State Estimation techniques such as the Kalman filter for linear data models can also be used in a prognostic technique. In this approach, the minimization of the error between a model and the available measurements is used to predict future behavior of the features. For a given measurement or extracted feature, a simple model of the feature dynamics can be implemented. The error covariance associated with the measurement noise is typically based on actual noise variances, while the process noise is usually based on the characteristics of the simple model. In the end, the filter (e.g., state estimator) approach is used to track and smooth the features related to the prediction of how a given failure mode is progressing.

Physics-Based Prognostics

A physics-based stochastic model may be used for component failure mode prognostics. It can also be used to predict the remaining useful life of a component. In this case, given the current operating conditions, the stochastic model is used to estimate the state of the failure process, and this information is then used in conjunction with the model to predict the future state of the system. This model can also be used to train a neural network or probabilistic-based autonomous system for real-time failure prognostic predictions. Because this is a model-based approach, at least a basic knowledge of the system including the failure modes and uncertainties is required.

Lubricant Health Prognostic System

When lubricants are used in a system, the oxidation inhibitors in the lubricant deplete to a certain critical level at which point the lubricant begins to degrade and polymerize at an accelerated rate. A significant change in the physical properties of the base oil such as viscosity, clarity, and conductivity begin to occur at this point. This point is referred to as the end of the useful life of the lubricant. The prediction of the remaining useful lubricant life (RUL) is very important to maintaining the overall health and operational capability of a machine. It also provides important information to help optimize maintenance schedules and minimize lubricant costs while avoiding unscheduled equipment failures. There have been significant efforts to develop lubricant heath prognosis systems. Schwartz and Smolenski developed an automatic engine oil change indicator system by studying the degradation of engine oil in various conditions. They determined the remaining distance that can be traveled before the next required oil change by using a linear regression model that is determined by lubricant health indicators such as TAN, TBN, and the oil oxidation induction time. The current distance and the intersection between the computations from the linear model and the limits of the health indicators provide an approximation of the remaining distance before the next oil change. Price and Centers developed a simple lubricant degradation model using laboratory data. The results from their computer simulation show a good prediction of lubricant degradation. However, this simple model cannot capture many important lubricant degradation factors such as wear metal contamination. Byington and Garga developed an electrical circuit model of a turbine engine lubrication system. This model generates lubricant failure data for developing the lubricant prognostic system. This system predicts the remaining useful life of the lubricant based on the outputs of neural networks, a fuzzy logic interface and an expert system.

Development of Lubricant Health Prognosis

The lubricant health prognosis system using data from the MEMS sensor array optionally uses diagnostic results, experienced-based and statistically estimated future conditions (e.g., future state 112) to determine the remaining useful life of the lubricant. This system can be based upon experimental data, instead of model-driven data from simulations experiments. An approach to the development of the lubricant prognostic system is to use evolutionary or trending models of the lubricant health indicators. These models will assist the prognostic system in the prediction of the remaining lubricant useful life. Although the model-based prognostics approach has the potential for providing a more accurate prediction than the evolutionary prognostic approach, this prognosis approach requires not only detailed knowledge of lubricant and its failure modes, but also the interaction between the lubricant and other system elements (e.g. mechanical structures).

Figure 43:
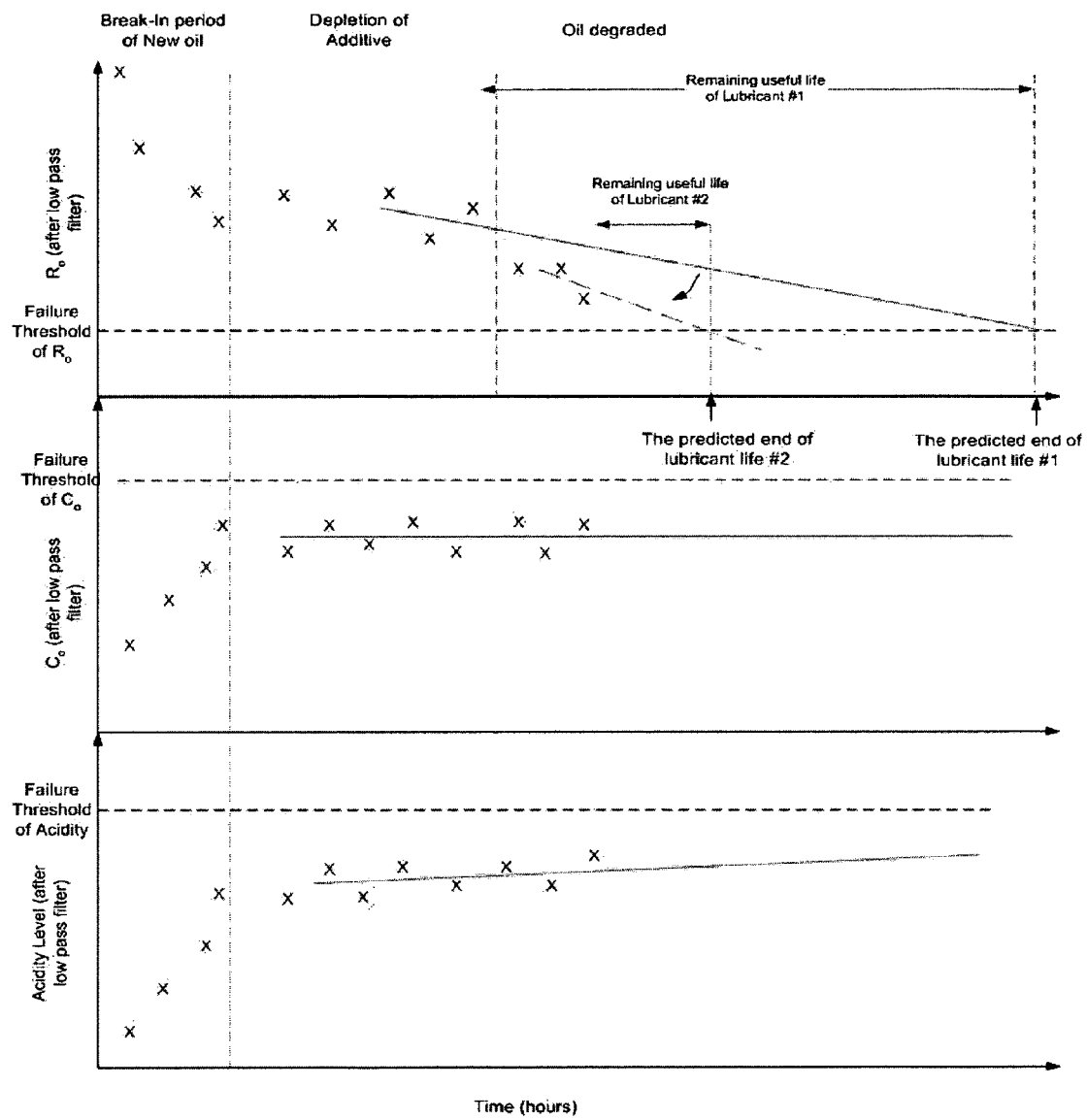
FIG. 43 is a plot of lubricant health prognosis using recursive linear regression.

A prognostic approach that utilizes the trends of lubricant health indicators (after the signal conditioning process) is shown in FIG. 43, which illustrates the implementation of the recursive linear regression of the lubricant health indicators in a given data window. Greitzer and Pawlowski used this simple approach to develop an onboard Prognostic Health Monitoring (PHM) system for the gas turbine engine used on the US Army M1 Abrams tank. By assuming that the lubricating oil is degrading similar to the lubricant in the gearbox experiment without an externally applied load, the bulk resistance ($R_o$), the bulk capacitance ($C_o$), and the acidity level (A) of the oil are slightly changed during the depletion of the additive. During the oil degradation period, the rate of $R_o$ change will increase as a result of the presence of iron wear debris. The rates of change of the bulk capacitance and the acidity level are not significantly different from the depletion of the additive in the "oil ok" period.

The RUL of the lubricant is estimated by computing the predicted end of lubricant life using the model developed from the data. The RUL point can be calculated from the intersection of the regression line that best fits the most recent lubricant health indicator data within the regression data window and the failure threshold of the lubricant health indicator. The predicted end of lubricant life during the additive depletion period (#1) will be longer than the one (#2) during the lubricant degraded period because the rate of change of $R_o$ change is increased. The size of the regression window is a very critical parameter. Noisy measurements can have an adverse effect on the predictions of the lubricant health indicators. The effect of noise can be reduced by increasing the size of the regression window size. However, this may also yield a prediction that is less sensitive to recent changes. One way to trade-off between these two factors is to increase the size of the regression data window, and employ a forgetting factor on the data to reduce the impact of older data on the prediction. Our method to estimate the RUL is to apply the LEAP-Frog technique. Greztizer and Ferryman reported the improvement of RUL prediction from simulated sensor data in the case of slow degradation and sudden changes of the data. This technique is a recursive linear regression method with adaptive window size. The RUL can be estimated using the computational procedure shown in the flowchart of FIG. 44.

Figure 44:
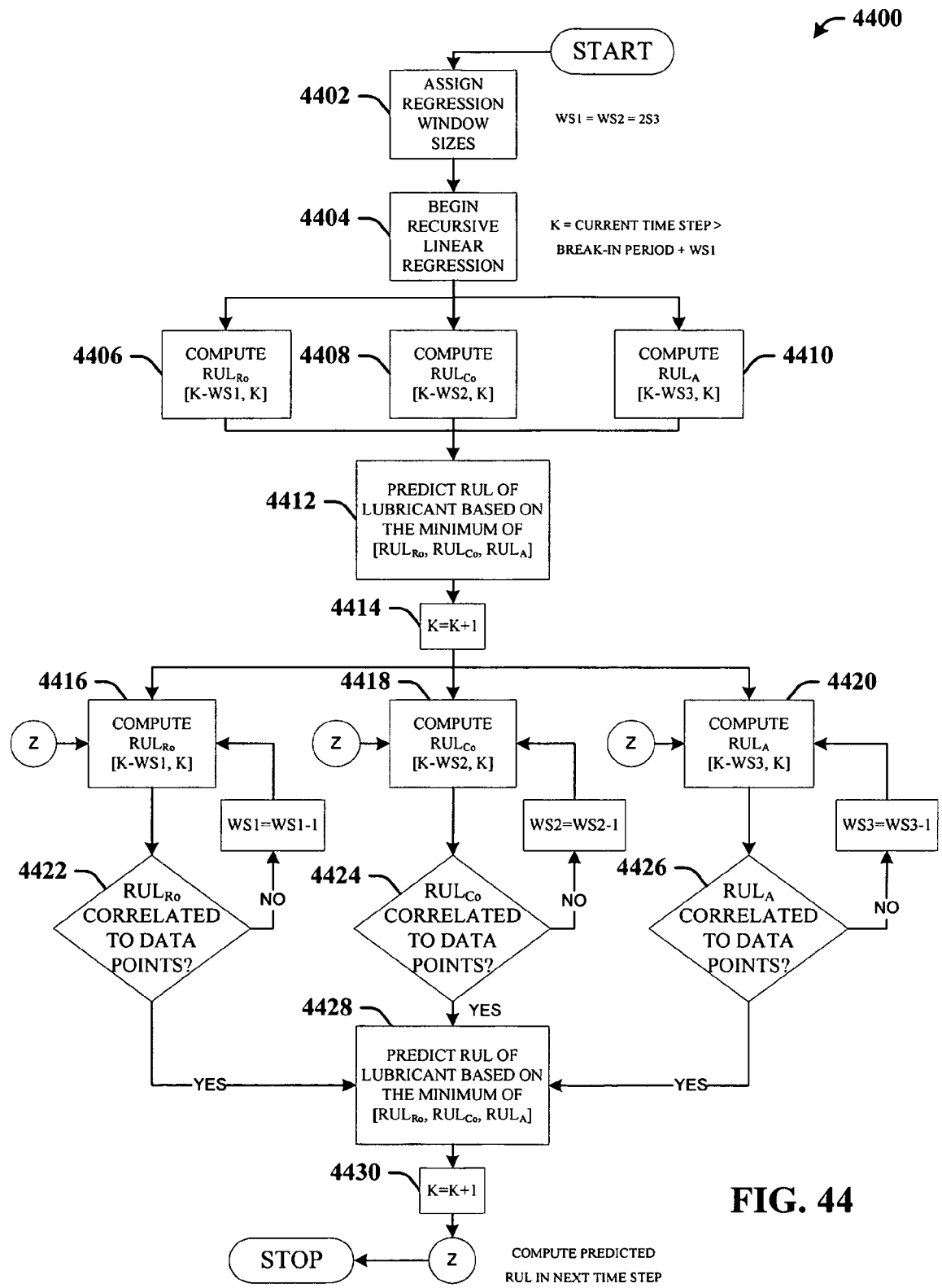
FIG. 44 is an exemplary flow chart of recursive linear regression using LEAP-Frog technique.

Referring now to FIG. 44, a method 4400 for recursive linear regression using LEAP-Frog technique is depicted. At 4402, a relative large regression window for $R_o$, $C_o$ and A can be selected, e.g., ws1 for $R_o$, ws2 for $C_o$, and ws3 for A. The initial regression windows can be initially set to the same size. At 4404, the RUL prediction can begin at time t*+ws1, t* can be, e.g., the break-in period of new oil. At 4406, the linear regression can be computed by using the recent ws1 $R_o$ data. Similarly, at 4408 and 4410, the remaining useful life can be predicted based upon $C_o$ and A, respectively data for computing the estimated RUL from the $C_o$ and A data. At 4412, the predicted end of lubricant life is computed from the intersection between the regression line and the $R_o$ failure threshold when coming from 4406 (and similarly $C_o$ and A data when coming from 4408 and 4410, respectively). The estimated RUL from $R_o$ data ($RUL_{Ro}$) is then the time period between the current time and the predicted end of the lubricant life (and similarly $C_o$ and A data when coming from 4408 and 4410, respectively).

At 4414, the predicted RUL at the current time is the minimum of $RUL_{Ro}$, $RUL_{Co}$, and $RUL_A$. At 4416-4420, the next time step, $RUL_{Ro}$, $RUL_{Co}$, $RUL_A$, respectively can be computed using the ws1 data window size. At 4422-4426, the $RUL_{Ro}$, $RUL_{Co}$, $RUL_A$, respectively can be evaluated to see if it is reasonably compatible with the most recent data points (e.g., $R_o C_o$ and A, respectively). For example, if the trend of the $R_o$ data decreases significantly in the last three $R_o$ data points, then the current $RUL_{Ro}$ should be less than the $RUL_{Ro}$ computed from the previous time step. If the current $RUL_{Ro}$ is still not compatible with the current $R_o$ data, then the size of the regression window ws1 is reduced and act 4416 is repeated (or acts 4418 and 4420 for $C_o$ and A data). This reduction of the regression windows continues until it yields a small enough window that is compatible with the most recent data points. As a result, this method can detect if the most recent data points indicate a change from the long-term regression. At 4428, the predicted RUL at the next time step is the minimum of $RUL_{Ro}$, $RUL_{Co}$, $RUL_A$.

In accordance therewith, the RUL can be predicted by using all the lubricant health indicators (e.g., 3410 from FIG. 34). In the experiment with the laboratory gearbox with load, it is clear that $R_o$ can be used to predict the remaining useful life of the lubricant because the rest of the lubricant health indicators changed only slightly after the break-in period. However, the $R_o$ failure threshold must be selected appropriately because there is an inflection point in the $R_o$ trend. By considering the decreasing rate of $R_o$ it is evident that the RUL of the lubricant in the gearbox experiment (Table 6) without load will be longer than the RUL of lubricant in the gearbox experiment with load at the end of the experiment. The study of this simple lubricant prognostic system can provides an example of how the lubricant health indicators can be used to predict the RUL of the lubricant.

Figure 45:
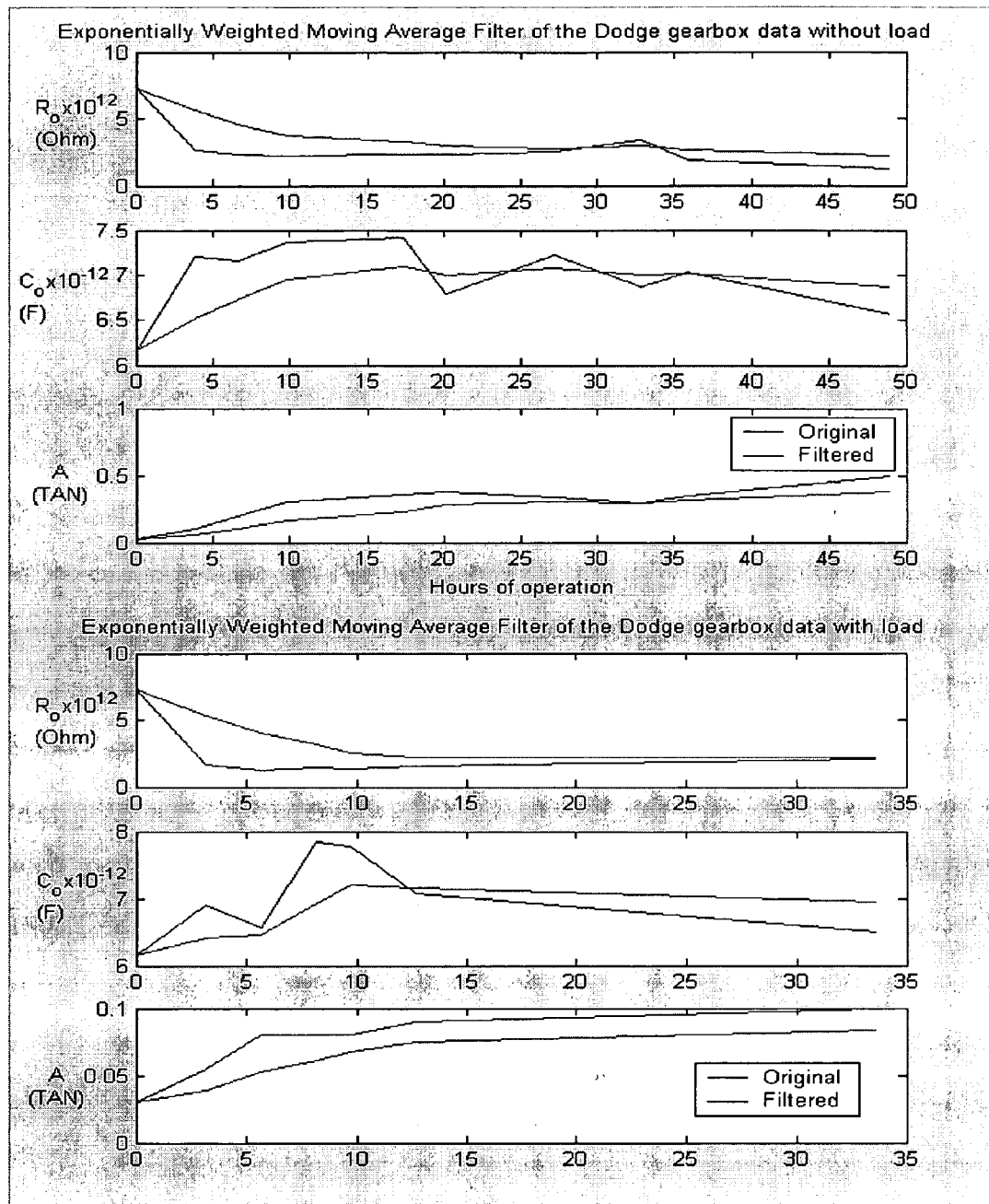
FIG. 45 is a plot of gearbox data signal conditioning employing a weighted moving average filter with no load (top) and with load (bottom).

Demonstration of the Lubricant Health Prognostic System with Laboratory Gearbox Data Referring now to FIG. 45, a phase in the development of a lubricant health prognostic system using the gearbox data is depicted. FIG. 45. This plot illustrates the lubricant health indicators after signal conditioning using an exponentially weighted moving average filter (with load and no load). The acidity data shown in the diagrams are the TAN values from Table 6. The missing TAN data at specific time k in Table 6 can be approximated by the interpolation between two known TAN values at times k−1 and k+1. The filtered lubricant health indicators are then used to predict the remaining useful life of the lubricant. By setting the failure thresholds of $R_o$, $C_o$ and A, the predicted end of lubricant life can be calculated by the intersection between the regression line and the failure threshold.

Figure 46:
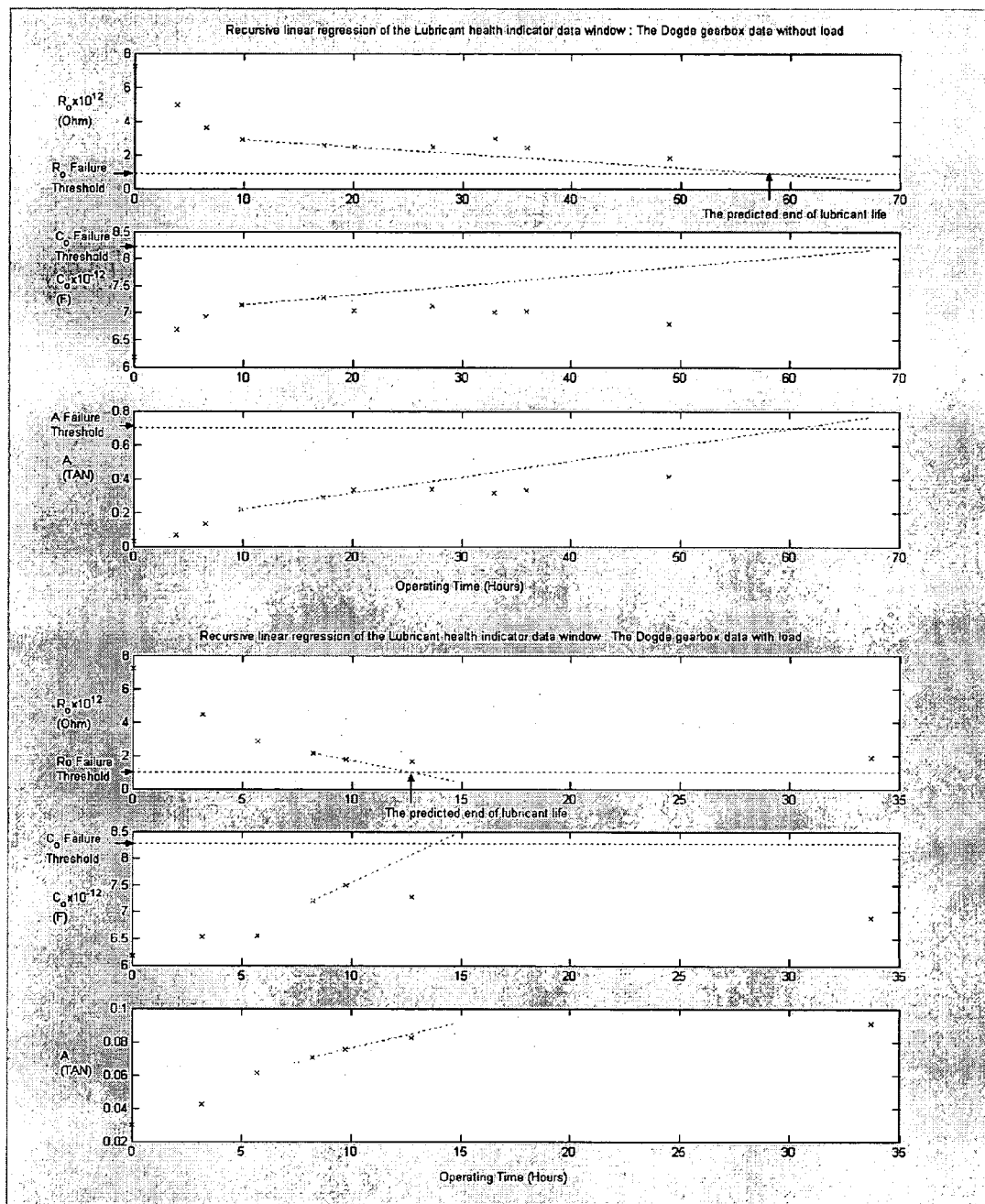
FIG. 46 is a plot of predicted end of lubricant life from gearbox data at (top) 17.3 hours and no load and (bottom) at 9.7 hours with load.

FIG. 46 (top three graphics) shows the predicted end of the lubricant life of the gearbox without the load at time 17.3 hours. The recursive liner regression method was used to compute the regression line with the window data size equal to two. The predicted end of lubricant life is computed from the intersection between the regression line and the $R_o$ failure threshold. It is shown in the diagram that the remaining useful life of the lubricant is approximately 58−17.3=40.7 hours. By using the same failure thresholds, the predicted end of the lubricant life from the gearbox with load is computed to be 9.7 hours as shown in FIG. 46 (bottom three graphs). It was again computed from the intersection between the regression line and the $R_o$ failure threshold. The result shows that the remaining useful life of the lubricant is approximately 12.5−9.7=2.8 hours. The health of the lubricant using the gearbox test with the load was evaluated by an external laboratory as being severe at time 33.4 hours, and the health of the lubricant using the gearbox test without load was evaluated as being moderate at 40.3 hours. These demonstrations show that this first phase development of a prognostic system is capable of an accurate and useful RUL prediction for a lubricating fluid.

Sensor Packaging

The sensor chip with electrical interface circuitry can be integrated into a compact package that permits embedding the sensor into operating machinery. The package design is intended to be close to a conventional design yet can provide for easily accessing and swapping sensor elements and electrical components. The package design can incorporate features that accommodate the unique sensor, electronics, and signal requirements for the fluid sensor.

Some of the aspects for the sensor package can include aspects such as low cost and easy fabrication, easy to disassemble and re-assemble, water tight, resistant to exposure to the fluids, sensor chip element readily replaceable, electronics board readily replaceable, isolation from stray fields, rugged, modular, and easy to embed into machinery. Accordingly, a ceramic "carrier" for the sensor chip element that can plug into the circuit board can be employed to provide these aspects.

Figure 47:
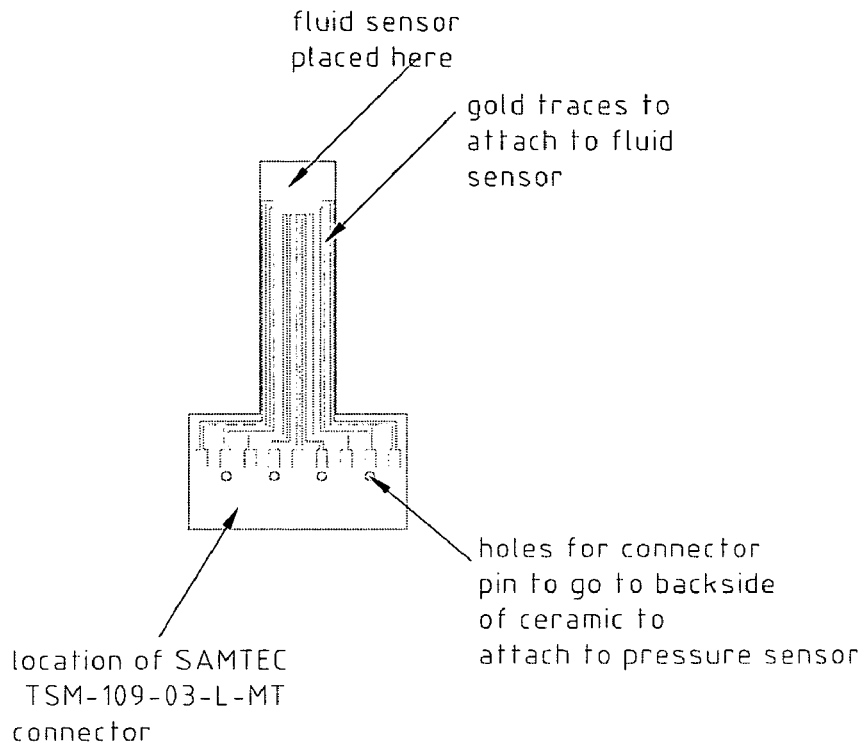
FIG. 47 is an exemplary illustration of a ceramic mounting plate for a sensor.
Figure 48:
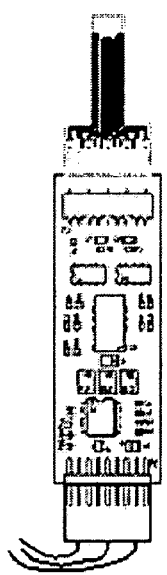
FIG. 48 is an exemplary illustration of a wired sensor assembly.
Figure 49:
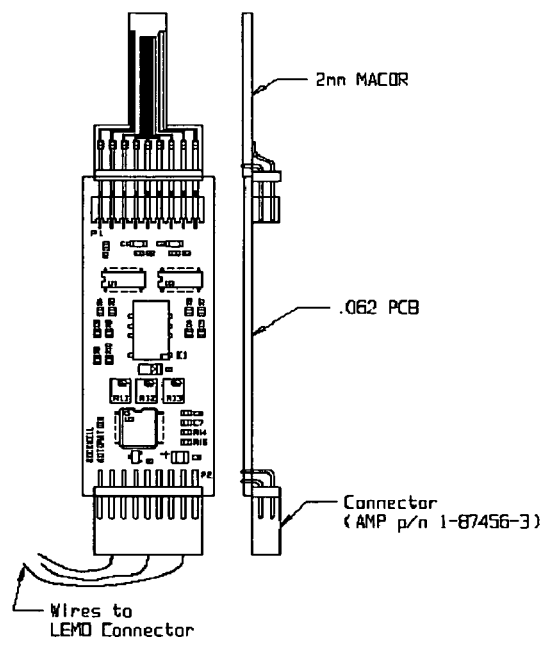
FIG. 49 is an exemplary illustration of a sensor carrier and PCB assembly.

With reference now to FIGS. 47-49, a ceramic carrier for the sensor, a wired sensor assembly and a sensor carrier and PCB assembly are depicted, respectively. The sensor chip can be mounted at the tip of the mounting plate and can be wire bonded to the parallel traces patterned on the ceramic substrate. The back side of the ceramic mounting plate (not shown) can have a small pressure transducer secured and the lead wires brought to the wide end of the T-shaped ceramic plate. Alternatively, additional electrical or electro-chemical sensor elements may be attached to the back side of the ceramic mounting plate and/or MEMs sensors (e.g., MEMS viscosity sensor) may be attached to either or both sides of the mounting plats. A connector (e.g., Samtec connector) can be soldered to the wide end of the ceramic plate to permit secure electrical connections to a replaceable sensor element.

As shown, there are eight connections on the side with the sensor chip and four through-pins to connect to the pressure transducer wires on the back side of the mounting plate. A mating connector on the printed circuit board can permit the sensor chip mounted on the ceramic carrier to be easily plugged in or un-plugged to test different sensors or to accommodate new sensor designs. A small connector (e.g., AMP connector) is shown on the circuit board with representative wires shown. This connector can facilitate disconnecting the circuit board from the sensor housing connector as illustrated in FIG. 48. FIG. 49 shows a top view and side view dimension drawing of the circuit board and sensor mounting plate assembly.

The circuit board and ceramic mounting plate shown can be assembled into a cylindrical metal case, as illustrated in FIGS. 50-52. At one end of the metal cylinder is the exposed end of the sensor chip. This end can also have a threaded based for rigidly installing the sensor in operating machinery. The devices can use a standard ½" NPT thread. This is a readily available, standard thread size that permits sealing the fluid at the sensor connections. The other end of the metal cylinder is a water tight connector. The prototype device uses a Mil-spec LEMO connector with 19 contacts. These connections provide power to the sensor and electronics and permit reading individual signals from the fluid sensor elements, pressure transducer, and embedded accelerometer. FIG. 50 shows a cutaway drawing of the sensor assembly with the watertight connector. The cylindrical tube can be made of stainless steel and the end fittings can be constructed of brass. A set of small screws is used to attach the top fitting to the cylinder. A rubber plug with a small slot can be sectioned in half and used to seal the ceramic sensor mounting plate inside the fixture and prevent the sampled fluid from entering the interior of the cylinder. Commercially available RTV can be used for sealing the edges and threaded fitting of the sensor package. FIG. 51 show the sensor fully assembled, while FIG. 52 displays the sensor disassembled.

Sensor Integration with a Data Network

There is growing interest in low-cost, high-performance sensor networks. Effective wired networks for distributed sensors include DeviceNet and IntelliBus networks. These networks can provide services such as high throughput, reliability, determinism, node-level intelligence, routing, distributed power, and compact-efficient packaging. These characteristics can be important for effective and adaptable industrial, commercial, marine, and vehicle sensor networks. Other benefits such as reduction in wiring, weight, power consumption, and capabilities for distributed intelligent sensor nodes with centralized storage and control are particularly appealing for the fluid sensor suite.

According to one aspect of the claimed subject matter, an integration of the multi-element fluid sensor with DeviceNet or IntelliBus can be employed. One solution is to integrate the sensor drive and analysis logic with the network interface logic on a single chip or circuit (e.g., controller area network chip—CAN device. This can provide a compact efficient sensor interface. Another technique to interface the sensor to a network can employ a Serial Peripheral Interface (SPI) peripheral interface. This may be implemented efficiently with proper coordination of signal interfaces, communications protocols, and timing. Hardware and software may be readily integrated with the fluid sensor to provide an efficient fluid sensor interface for distributed fluid sensing. Multiple fluid parameters as well as other parameters such as e.g., vibration and/or noise data can be provided through the network for routing, data analysis, trending, remote storage, operations and maintenance scheduling, and remote display.

Figure 54:
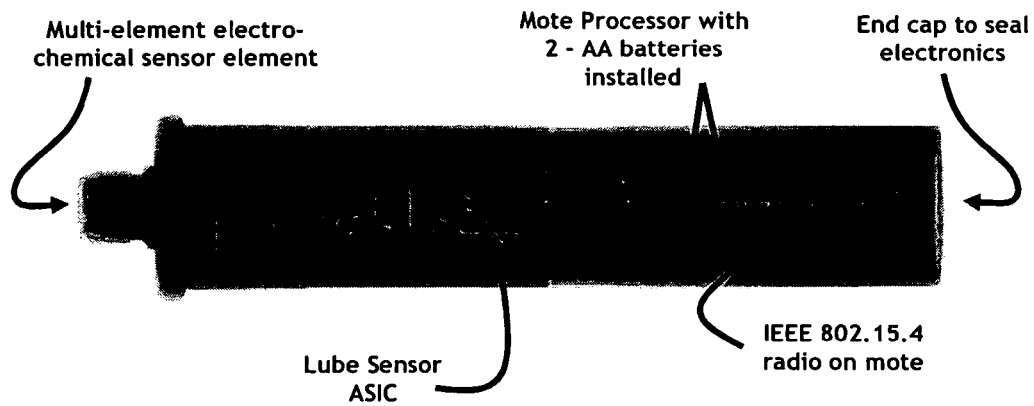
FIG. 54 depicts an X-ray image of a wireless fluid sensor.
Figure 55:
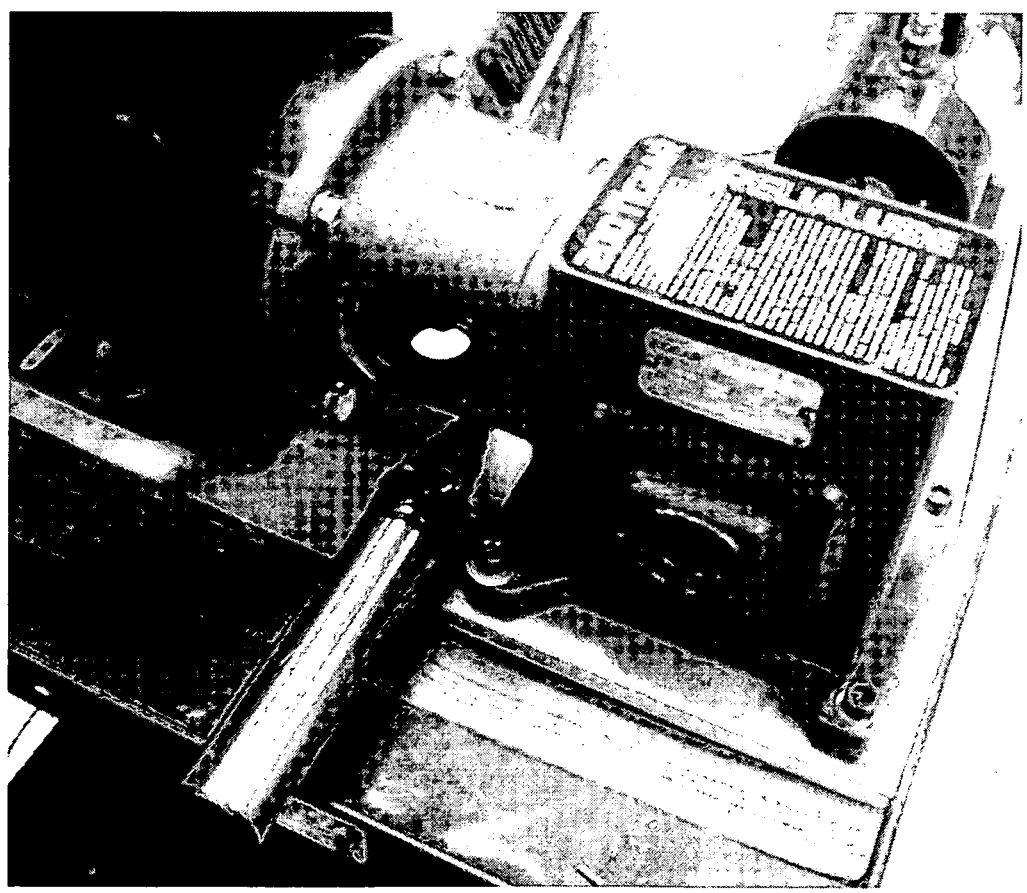
FIG. 55 illustrates a motor-gearbox test stand with a sensor mounted under the gearbox flange.
Figure 56:
FIG. 56 depicts a handheld computer that wirelessly receives fluid sensor data.

An implementation of a direct network interface with the fluid health sensor can provide a basis for a low-cost, high performance distributed sensing network. Distributed processing of multi-sensor machinery data minimizes bandwidth requirements of the network while providing for area sensing and analysis that incorporates the inherent coupling of many high-performance systems (e.g., aircraft systems). A suite of different sensors may be networked together to provide local, component-specific sensing and analysis and summary real-time information aggregated to provide a more accurate, comprehensive picture of the state of the dynamic system. Additionally, the fluid sensor may be networked using existing wireless networks such as IEEE 802.15.4, Bluetooth, or wireless Ethernet (e.g., IEEE 802.11b). An example of a wireless integrated fluid sensor is shown in FIGS. 54-56. FIG. 54 depicts an X-ray image of a wireless fluid sensor. FIG. 55 illustrates a motor-gearbox test stand with a sensor mounted under the gearbox flange. FIG. 56 depicts a handheld computer that wirelessly receives fluid sensor data. For example, the sensor, amplifier electronics, control processor, programs, memory, and radio are contained in a sealed tube. Every 30 seconds, e.g., the fluid health is wirelessly transmitted to a radio interface connected to a personal digital assistant (PDA). The PDA can provide a local wireless data display and logs the data to memory for future analysis, trending, and archiving.

Control Integration—Integrated Circuit Implementation of Sensor Electronics

An Intelligent Fluid Condition Sensor can be a vitally important part of many systems such as aircraft engines, gearboxes, etc. Providing important fluid information is an important objective, e.g., to support machinery maintenance activities, operations, scheduling, machine control and environment control while avoiding machine failure. The sensor is capable of making logical decisions regarding the fluid chemistry and machinery health in a distributed manner at the source of the information. The intelligent sensor system can be adapted to automatically act on that information itself (e.g., turn on an oil cooler), or it can pass on a high-priority message, not just raw data for higher level control and decision support. The intelligent sensor may also send and receive data; perform self-testing and adaptive calibration; and offer dynamic setup and adjustment while rejecting spurious inputs.

The development of Integrated Circuit System Sensor enables physical sensors to be integrated with the control and signal processing electronics in a single, compact package. Application-Specific Integrated Circuits (ASICs) are becoming increasingly pervasive in sensor-related systems. Portability and robustness are two main advantages of ASICs compared to discrete implementations. Current submicron CMOS technologies offer provide high-performance, rugged circuits with low-power dissipation, small size, light weight, and low-cost compared to discrete component implementations.

Design Options for Developing a Low-Cost Integrated Intelligent Fluid Sensor System The critical sensor interface elements of the multi-element sensor such as amplifiers and filters have been developed in an ASIC using standard commercial fabrication design rules and facilities. This has resulted in a low-cost sensor module integrated with the sensor elements. Together these elements form a SoC (System-on-a-chip) The analog ASIC developed for the multi-element sensor may be readily expanded to include a microprocessor core and associate memory and I/O elements using establish mixed-signal design and fabrication techniques.

System Integration

The architecture of the multi-element fluid sensor is consistent with the trend toward distributed intelligent sensing and analysis. The multi-element sensor and embedded logic provides a high degree of reliability and "ride through" capability in the event of partial failure. Analytic results or raw data may be optionally provided to a central-level or higher-level system for subsystem or system-level health assessment. An open architecture is employed to permit other systems to readily interact with the multi-element intelligent sensor. A leading open diagnostic interface architecture is the Open Systems Architecture for Condition-Based Maintenance (OSA-CBM). OSA-CBM has transitioned to a standards group (MIMOSA) for enhancement and support. It is now the basis for an international standard for machinery monitoring and diagnostics, ISO 13374. This international standards effort will promote the deployment of low-cost intelligent sensors such as the fluid sensor.

The sensor design provides flexibility in networking. The bandwidth requirements may be adjusted dynamically based on network capacity and other data communications requirements. Rather than sending raw sensor data, only the results of the embedded analysis may be provided or only summary information provided for an exception or fault detection. The sensor is readily networked using open, standard networks as described in the demonstration section. The sensor architecture provides a very efficient interface to a wired network (e.g., DeviceNet) or a wireless network (e.g. IEEE 802.15.4 or wireless Ethernet).

There is a transition from an architecture characterized by central control and coordination to one employing highly distributed, autonomous and cooperating devices. This architecture can be deployed on commercial, industrial, marine, and other systems. Among the benefits of these systems are the dynamic highly adaptive nature of cooperating agent (e.g., "emergent" behavior) and the lack of a central control and coordination function thereby eliminating any single point of failure. In accordance therewith, multi-agent systems (MAS) and/or collective intelligence (COIN) can provide the framework for these systems. International standards efforts (e.g., FIPA) are focused on insuring the interoperability of agents across vendors and across platforms. The intelligent fluid sensor is compatible with this architecture due to the low-cost, small size, distributed intelligence, and generation of control recommendations. This architecture permits sensor to sensor communication and collaboration. Multi-sensor collaboration can support enhanced fluid and system diagnostics, improved maintenance and operations decision-making, and superior compensating control. Sensor elements may be embedded in critical machines and insure continued component protection and operation in an efficient manner, even without central control or communications. For example, multi-element sensor/controller modules could be embedded into hydraulic pump, filter, valves, and actuator components. Faults detected such as degraded fluid, water contamination or loss of fluid could prescribe the automatic redirection of fluid flow and isolation of a broken hydraulic line or faulty filter element. Similar capabilities employing autonomous agents for pumps and valves have been demonstrated to provide a highly survivable chilled water system for a Navy application.

Sensor Enhancement

The core sensor previously described can be selectively and incrementally enhanced to effectively meet unique and challenging application requirements. Examples of enhancements to the core fluid sensor are identified below in Table 10.

TABLE 10

Sensor Enhancement - (Enable New Sensor Capabilities)

| No. | Activity | Comments |
| --- | --- | --- |
| 1 | Integrate additional sensing modalities | Integrate additional sensor technologies with the multi-element sensor. The following sensor elements are recommended:<br>a. MEMS viscosity sensing - viscosity is a critical fluid parameter that provides enhanced diagnostic capabilities. Virtually every outside lab oil analysis includes a viscosity measurement. A unique MEMS viscosity sensor has been demonstrated in gear oil in a separate program at Rockwell Automation. This important sensing capability can be readily integrated with the existing sensor elements.<br>b. Corrosion sensing - corrosion sensing based on established micro-electrode and MEMS structures may readily integrate with the fluid sensor. Corrosion continues to be a prevalent and costly maintenance burden across many commercial (e.g. bridges) and military systems (e.g. ships, vehicles, and aircraft). |

TABLE 10-continued

Sensor Enhancement - (Enable New Sensor Capabilities)

| No. | Activity | Comments |
|---|---|---|
| | c. | Micro-spectrometry - low cost source-detector and VCELs can provide extremely valuable spectroscopic information regarding fluid chemistry, additive levels, and contaminants. These may be readily integrated with the existing multi-element fluid sensor. |
| | d. | Lubricity sensing - lubricity is recognized as an important fluid parameter particularly for high performance engines. A MEMS fluid shear structure coupled with the existing sensor elements may efficiently estimate this important fluid parameter. |

Additional sensor capabilities may be readily incorporated into the core sensor as the new capabilities become mature enough for deployment. Information on fluid health and machinery diagnostic and prognostic is extremely valuable for maintenance and operations decisions. Additional benefits may be obtained by integrating the fluid sensor with other system components.

Sensor System Integration

Real-time fluid condition and machinery health is uniquely available in real-time by employing the multi-element fluid sensor as described above. Integrating the sensor with other system components, computer systems, and controllers can provide unique and powerful capabilities. These areas are summarized in Table 11 below.

TABLE 11

Sensor System Integration - (Unique Machinery Protection)

| No. | Activity | Comments |
|---|---|---|
| 1 | Embedded Sensor in System Components | The prototype fluid sensor is implemented in a threaded cylinder that may be screwed into a tapped hole in machinery. Several concept packages have been fabricated that integrate an oil filters and a fuel filter. Integrating the sensor into existing components such as a pump, valve, actuator, or filter, additional capabilities are readily available including the ability to diagnose the condition of the integrated system component. For example, the sensor embedded in the fuel filter enables the sensor to be readily deployed in aircraft without any modifications to the basic component (e.g. valve, pump, or manifold). The "intelligent" filter can efficiently diagnose the fuel, fuel additives, and detect contaminants as well as continuously monitor the integrity and performance of the filter element. |
| 2 | Micro-computer Integration | Signal processing including filtering, sensor fusion, and diagnostic is performed on the raw sensor signals from the multi-element sensor. Integrating the processor with analog circuitry into a self-contained module provides a very effective sensor testing and data acquisition system. Computer-electronics-sensor integration provides for a self-contained unit that may be provided to outside laboratories for extensive fluid testing and may be deployed on vehicles or other field test systems to acquire actual field data. Near- |

TABLE 11-continued

Sensor System Integration - (Unique Machinery Protection)

| No. | Activity | Comments |
|---|---|---|
| | | term benefits such as reduced cost for fluid testing, in-field application testing, and large-scale data acquisition are possible by providing a compact, functional sensor processing unit. |
| 3 | Dynamic Fluid Chemistry Control | In addition to or instead of logging, communicating, or annunciating a faulty fluid condition the multi-element fluid sensor may dynamically eliminate, defer, or reduce the faulty fluid condition - before damage or a shutdown occurs. For example, after sensing a depletion of antioxidant, the sensor logic may direct the injection of a prescribed amount of pure additive into the fluid stream. Subsequent sensing and analysis will confirm that the correct amount of fluid was added and the fluid is now in the safe operating range. Fluid alteration done in a closed-loop manner will extend the life of the fluid and mechanical components and prevent machinery failure or the inadvertent shutdown of critical machinery. |

Sensor integration can extend the capabilities and operational impact of the fluid sensor in several novel and important areas. The full effectiveness of the intelligent fluid sensor may be realized when implemented in an integrated manner as part of the complete control and information system of a manufacturing system, commercial system, vehicle, ship, or aircraft for example.

Sensor Communications and Architecture

The fluid health sensor capabilities and potential impact are enhanced through network communications and through appropriate architectural implementation that support data integration, process analysis, control, and system integration. The communications and architecture concepts presented below in Table 12 expand the capabilities and benefits of the multi-element sensor previously described.

TABLE 12

Sensor Communications and Architecture - (Distributed Intelligence)

| No. | Facility/Functionality | Comments |
|---|---|---|
| 1 | Remote Database Access | Localized sensing, processing, and diagnostic occur within the integrated sensor unit as described previously. Permitting the intelligent sensor to remotely access other sensors or a database of fluid characteristics will significantly extend the capabilities of the sensor. This will provide a basis for adaptive sensing and the collective learning across the population of all sensors. For example, the embedded logic may establish the existence of an unknown fluid, contaminant, or degradation profile. The sensor may poll other sensors or a centralized database to determine similar markers or characteristics from other fluids or operating domains. A simple case-based reasoning scheme may be readily deployed for this function. Adaptive sensing and collective learning is a very unique and powerful capability. |

TABLE 12-continued

Sensor Communications and Architecture - (Distributed Intelligence)

| No. | Facility/<br>Functionality | Comments |
|---|---|---|
| 2 | Wired Network Interface | There is growing interest in low-cost, highly-efficient sensor networks. Existing networks such as, DeviceNet, Fieldbus, or IntelliBus provides efficient access to sensor data and may control sensor operation. An efficient network interface may be readily incorporated into the FPGA or ASIC sensor interface as described above. |
| 3 | Self-powered Wireless Sensor | Many fluids to be monitored do not have power or communications readily available. While wireless communications has important advantages, these are often outweighed by the need to run power wires or periodically replace batteries. An important characteristic of the fluid health sensor is the ability to operate the sensor element with very low power requirements. Energy harvesting techniques previously demonstrated are capable of generating the required power by scavenging power from the environment and using this to periodically operate the fluid health sensor. Such a sensor requiring no maintenance or human access may be embedded into machinery and put in inaccessible locations. The self-powered sensor will continuously generate energy from the environment and periodically report by way of a radio link the condition of the fluid and of the remotely monitored machinery. A self-powered fluid sensor is a unique and powerful device that opens up many new monitoring, operations, surveillance, safety, security, and control opportunities. |
| 4 | Autonomous Agent Implementation | Additional capabilities are possible by augmenting the fluid sensor with integrated local processing, control, and communications capabilities. Combining these capabilities in an agent-based framework enables a new operating paradigm. A collection of autonomous, cooperating "intelligent" agents can leverage existing agent communications standards (e.g. FIPA) and provide very unique and unprecedented capabilities. The range of capabilities includes dynamic re-configuration and control (e.g. emergent behavior) to achieve mission requirements or protect critical system components or personnel. Other capabilities such as cooperative behavior may utilize the coupled, dynamically linked characteristic of system components and operating capabilities. These capabilities can significantly extend the impact and opportunities of an intelligent multi-element sensor system. |

What has been described above includes examples of the claimed subject matter. It is, of course, not possible to describe every conceivable combination of components or methodologies for purposes of describing the present invention, but one of ordinary skill in the art may recognize that many further combinations and permutations of the present invention are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates machinery diagnostics, prognostics and control by way of condition sensing, comprising:
a device with a fluid and a mode of operation;
a fluid sensor in contact with the fluid that measures a parameter of the fluid and transmits data associated with the parameter, the fluid sensor is powered by an attribute of the fluid; and
a control component that receives the data, determines a current state of the fluid, and infers a future state of the fluid in real-time.

2. The system of claim 1, the parameter is at least one of oxidation level, temperature, viscosity, oxidation/reduction potential, pH, dielectric, TAN, $H_2O$, conductivity, ferrous contamination, additive state, and chemical contaminants.

3. The system of claim 1, the control component determines the current state based at least in part upon a comparison of the data with pre-existing state data associated with the fluid.

4. The system of claim 1, the control component infers the future state based upon at least one the current state, pre-existing state data associated with the fluid and a prognostics algorithm.

5. The system of claim 1, the control component is embedded in the fluid sensor.

6. The system of claim 1, the control component is remote from the fluid sensor.

7. The system of claim 6, the control component communicates with the fluid sensor by way of wireless communication.

8. The system of claim 1, further comprising a sensor network that is at least one of a DeviceNet network and an IntelliBus network.

9. The system of claim 1, the current state is an evaluation of a health of the fluid.

10. The system of claim 1, the future state is an estimate of a useful life of the fluid.

11. The system of claim 1, the control component determines a remedial action and provides control information in connection with the remedial action.

12. The system of claim 11, the remedial action is at least one of a change of the mode of operation of the device and a release of an additive into the fluid.

13. The system of claim 12, the control component implements the remedial action by transmitting the control information to the device.

14. The system of claim 11, the control component transmits the control information as an alert.

15. The system of claim 1, the fluid sensor is at least one of an RTD sensor, an acidity sensor, an impedance sensor, an electrochemical sensor and a moisture sensor.

16. The system of claim 1, the fluid sensor is a smart sensor that includes at least one data specification and operates in accordance with IEEE 1451 open standards.

17. The system of claim 1, further comprising at least one of a MEMS structure and a NANO structure that moves in the fluid and supplies energy to the fluid sensor.

18. The system of claim 17, the at least one of a MEMS structure and a NANO structure moves in the fluid based upon at least one of a fluid flow, a pressure fluctuation, a vibration from the device, and a thermal gradient.

19. The system of claim 17, the at least one of a MEMS structure and a NANO structure is at least one of a paddle wheel, a flapping plate, a rotating disk, a pressure diaphragm, a piezoelectric material, and a thermo-electric material.

20. The system of claim 1, the fluid is a dielectric fluid and the fluid sensor harvests energy based upon a charge extant in the dielectric fluid.

21. The system of claim 20, the charge is created from at least one of particle detachment, tribocharging, scuffing on a surface of the device, and work activity on a surface.

22. The system of claim 20, further comprising an electrode with a sacrificial element that supplies energy to the fluid sensor based upon an electrochemical reaction between the fluid and the element.

23. The system of claim 1, the fluid sensor is powered by a fuel cell that harvests energy from the fluid.

24. The system of claim 1, the device further comprising a microgenerator that supplies power to the fluid sensor.

25. The system of claim 1, the fluid sensor employs Electrical Impedance Spectroscopy (EIS) to determine a conductivity of the fluid.

26. The system of claim 25, the fluid sensor detects a metal ion signature of a metal by way of electrochemical analysis.

27. The system of claim 26, the control component employs the signature to determine the current state, the current state relates to at least one of metal wear in the device and an amount metal in the fluid.

28. The system of claim 27, the control component requests additional data from the fluid sensor, the additional data relates to probing and/or tracking.

29. The system of claim 28, the control component employs the additional data to infer and/or update the future state.

30. The system of claim 1, the fluid sensor includes an element that is coated with a material that enhances at least one of detection, identification and quantity determination of a biological agent in the fluid.

31. The system of claim 1, the fluid sensor includes an element that is coated with an ion selective coating or a coating that promotes selective ion transfer to enhance at least one of detection, identification and quantity determination of a material.

32. The system of claim 1, the fluid sensor is packaged in a ceramic carrier.

33. The system of claim 32, the ceramic carrier is at least one of inexpensive to fabricate, suitable for mass fabrication, easy to disassemble and re-assemble, water tight, resistant to exposure to the fluids, suitable for multiple sensors, easy to embed into the device, and capable of shielding the fluid sensor from a stray field.

34. The system of claim 1, further comprising a second sensor that measures a second parameter of the device in situ and transmits data associated with the second parameter to the control component.

35. The system of claim 34, the second parameter is at least one of a fluid parameter and a device parameter.

36. The system of claim 35, the device parameter relates to at least one of vibration data and a decibel level.

37. The system of claim 36, the control component receives data from the fluid sensor and the second sensor and employs sensor fusion to infer the future state.

* * * * *

UNITED STATES PATENT AND TRADEMARK OFFICE
CERTIFICATE OF CORRECTION

PATENT NO. : 7,581,434 B1  
APPLICATION NO. : 11/395790  
DATED : September 1, 2009  
INVENTOR(S) : Discenzo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this

Fourteenth Day of December, 2010

David J. Kappos  
*Director of the United States Patent and Trademark Office*